US007786285B2

(12) United States Patent
Smith et al.

(10) Patent No.: US 7,786,285 B2
(45) Date of Patent: Aug. 31, 2010

(54) RECOMBINANT VACCINE AGAINST BOTULINUM NEUROTOXIN

(75) Inventors: Leonard A. Smith, Clarksburg, MD (US); Michael P. Byrne, New Market, MD (US); John L. Middlebrook, Middletown, MD (US); Hugh Lapenotiere, Charlestown, WV (US); Michael A. Clayton, Mt. Airy, MD (US); Douglas R. Brown, Gaithersburg, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/437,212

(22) Filed: May 19, 2006

(65) Prior Publication Data

US 2007/0037257 A1 Feb. 15, 2007

Related U.S. Application Data

(60) Division of application No. 09/910,186, filed on Jul. 20, 2001, now Pat. No. 7,081,529, which is a continuation of application No. 09/611,419, filed on Jul. 6, 2000, now Pat. No. 7,214,787, which is a continuation-in-part of application No. 08/123,975, filed on Sep. 21, 1993, now abandoned, and a continuation of application No. PCT/US00/12890, filed on May 12, 2000.

(60) Provisional application No. 60/133,866, filed on May 12, 1999, provisional application No. 60/133,868, filed on May 12, 1999, provisional application No. 60/133,869, filed on May 12, 1999, provisional application No. 60/133,865, filed on May 12, 1999, provisional application No. 60/133,873, filed on May 12, 1999, provisional application No. 60/133,867, filed on May 12, 1999, provisional application No. 60/146,192, filed on Jul. 29, 1999.

(51) Int. Cl.
*C07H 21/02* (2006.01)
*C12N 15/09* (2006.01)

(52) U.S. Cl. .................... 536/23.7; 536/24.1; 435/69.1; 435/69.3; 435/69.7; 435/252.1; 435/252.3; 435/252.33; 435/320.1

(58) Field of Classification Search ....................... None
See application file for complete search history.

(56) References Cited

U.S. PATENT DOCUMENTS 5,389,540 A * 2/1995 Makoff et al. .............. 435/69.3

(Continued)

FOREIGN PATENT DOCUMENTS

| WO | 96/41881 | * | 12/1996 |
| WO | 98/08540 | * | 3/1998 |
| WO | 00/02524 | * | 1/2000 |

OTHER PUBLICATIONS

Accession No. X74162 *Clostridium botulinum* toxin serotype G gene, 1993.*

(Continued)

*Primary Examiner*—Robert B Mondesi
*Assistant Examiner*—Ginny Portner
(74) *Attorney, Agent, or Firm*—Elizabeth Arwine

(57) ABSTRACT

This invention is directed to preparation and expression of synthetic genes encoding polypeptides containing protective epitopes of botulinum neurotoxin (BoNT). The invention is also directed to production of immunogenic peptides encoded by the synthetic genes, as well as recovery and purification of the immunogenic peptides from recombinant organisms. The invention is also directed to methods of vaccination against botulism using the expressed peptides.

20 Claims, 22 Drawing Sheets

U.S. PATENT DOCUMENTS

| | | | | |
|---|---|---|---|---|
| 5,571,694 | A * | 11/1996 | Makoff et al. | 435/69.3 |
| 5,807,741 | A * | 9/1998 | Brown et al. | 435/340 |
| 5,919,665 | A * | 7/1999 | Williams | 435/71.1 |
| 6,203,794 | B1 * | 3/2001 | Dolly et al. | 424/184.1 |
| 6,488,926 | B1 * | 12/2002 | Khan et al. | 424/93.1 |
| 6,495,143 | B2 * | 12/2002 | Lee et al. | 424/199.1 |
| 6,730,499 | B1 * | 5/2004 | Cregg | 435/69.1 |
| 6,776,990 | B2 * | 8/2004 | Sachs et al. | 424/192.1 |
| 6,967,088 | B1 * | 11/2005 | Williams et al. | 435/69.1 |
| 7,037,680 | B2 * | 5/2006 | Smith et al. | 435/69.1 |
| 7,041,792 | B2 * | 5/2006 | Elmore et al. | 530/350 |
| 7,081,529 | B2 * | 7/2006 | Smith et al. | 536/23.7 |
| 7,214,787 | B1 * | 5/2007 | Smith et al. | 536/23.7 |
| 7,227,010 | B2 * | 6/2007 | Smith | 536/23.7 |
| 2002/0012658 | A1 * | 1/2002 | Williams et al. | 424/93.2 |
| 2002/0168727 | A1 * | 11/2002 | Smith et al. | 435/69.3 |
| 2003/0009025 | A1 * | 1/2003 | Smith et al. | 536/23.7 |
| 2007/0104737 | A1 * | 5/2007 | Smith | 424/239.1 |

OTHER PUBLICATIONS

Accession No. M92906 *Clostridum botulinum* toxin gene serotype F, 1992.*

Potter, KJ et al, Protein Expression and Purification, Aug. 1998, vol. 13, pp. 357-365.*

Campbell, KD et al, Journal of Clinical Microbiology, Sep. 1993, pp. 2255-2262, vol. 31(9).*

* cited by examiner

FIGURE 1

A: BoNTA(H<sub>C</sub>) synthetic gene (Version #1) SEQ ID NO: 1

GAATTCGAAACGatgCGTCTGCTGTCTACCTTCACTGAATACATCAAGAACATCAT
CAATACCTCCATCCTGAACCTGCGCTACGAATCCAATCACCTGATCGACCTGTCT
CGCTACGCTTCCAAAATCAACATCGGTTCTAAAGTTAACTTCGATCCGATCGAC
AAGAATCAGATCCAGCTGTTCAATCTGGAATCTTCCAAAATCGAAGTTATCCTG
AAGAATGCTATCGTATACAACTCTATGTACGAAAACTTCTCCACCTCCTTCTGGA
TCCGTATCCCGAAATACTTCAACTCCATCTCTCTGAACAATGAATACACCATCAT
CAACTGCATGGAAAACAATTCTGGTTGGAAAGTATCTCTGAACTACGGTGAAAT
CATCTGGACTCTGCAGGACACTCAGGAAATCAAACAGCGTGTTGTATTCAAATA
CTCTCAGATGATCAACATCTCTGACTACATCAATCGCTGGATCTTCGTTACCATC
ACCAACAATCGTCTGAATAACTCCAAAATCTACATCAACGGCCGTCTGATCGAC
CAGAAACCGATCTCCAATCTGGGTAACATCCACGCTTCTAATAACATCATGTTC
AAACTGGACGGTTGTCGTGACACTCACCGCTACATCTGGATCAAATACTTCAAT
CTGTTCGACAAAGAACTGAACGAAAAGAAATCAAAGACCTGTACGACAACCA
GTCCAATTCTGGTATCCTGAAAGACTTCTGGGGTGACTACCTGCAGTACGACAA
ACCGTACTACATGCTGAATCTGTACGATCCGAACAAATACGTTGACGTCAACAA
TGTAGGTATCCGCGGTTACATGTACCTGAAAGGTCCGCGTGGTTCTGTTATGACT
ACCAACATCTACCTGAACTCTTCCCTGTACCGTGGTACCAAATTCATCATCAAGA
AATACGCGTCTGGTAACAAGGACAATATCGTTCGCAACAATGATCGTGTATACA
TCAATGTTGTAGTTAAGAACAAAGAATACCGTCTGGCTACCAATGCTTCTCAGG
CTGGTGTAGAAAAGATCTTGTCTGCTCTGGAAATCCCGGACGTTGGTAATCTGT
CTCAGGTAGTTGTAATGAAATCCAAGAACGACCAGGGTATCACTAACAAATGCA
AAATGAATCTGCAGGACAACAATGGTAACGATATCGGTTTCATCGGTTTCCACC
AGTTCAACAATATCGCTAAACTGGTTGCTTCCAACTGGTACAATCGTCAGATCG
AACGTTCCTCTCGCACTCTGGGTTGCTCTTGGGAGTTCATCCCGGTTGATGACGG
TTGGGGTGAACGTCCGCTGtaaGAATTC

B: BoNTA(H<sub>C</sub>) encoded protein (Version #1) SEQ ID NO: 2

MRLLSTFTEYIKNIINTSILNLRYESNHLIDLSRYASKINIGSKVNFDPIDKNQIQLFNL
ESSKIEVILKNAIVYNSMYENFSTSFWIRIPKYFNSISLNNEYTIINCMENNSGWKVSL
NYGEIIWTLQDTQEIKQRVVFKYSQMINISDYINRWIFVTITNNRLNNSKIYINGRLID
QKPISNLGNIHASNNIMFKLDGCRDTHRYIWIKYFNLFDKELNEKEIKDLYDNQSNS
GILKDFWGDYLQYDKPYYMLNLYDPNKYVDVNNVGIRGYMYLKGPRGSVMTTNI
YLNSSLYRGTKFIIKKYASGNKDNIVRNNDRVYINVVVKNKEYRLATNASQAGVEK
ILSALEIPDVGNLSQVVVMKSKNDQGITNKCKMNLQDNNGNDIGFIGFHQFNNIAKL
VASNWYNRQIERSSRTLGCSWEFIPVDDGWGERPL*

FIGURE 2

A: BoNTA(H$_C$) synthetic gene (version #2) SEQ ID NO: 3

GAATTCGAAACGatgTCTACCTTCACTGAATACATCAAGAACATCATCAATACCT
CCATCCTGAACCTGCGCTACGAATCCAATCACCTGATCGACCTGTCTCGCTACGC
TTCCAAAATCAACATCGGTTCTAAAGTTAACTTCGATCCGATCGACAAGAATCA
GATCCAGCTGTTCAATCTGGAATCTTCCAAAATCGAAGTTATCCTGAAGAATGC
TATCGTATACAACTCTATGTACGAAAACTTCTCCACCTCCTTCTGGATCCGTATC
CCGAAATACTTCAACTCCATCTCTCTGAACAATGAATACACCATCATCAACTGC
ATGGAAAACAATTCTGGTTGGAAAGTATCTCTGAACTACGGTGAAATCATCTGG
ACTCTGCAGGACACTCAGGAAATCAAACAGCGTGTTGTATTCAAATACTCTCAG
ATGATCAACATCTCTGACTACATCAATCGCTGGATCTTCGTTACCATCACCAACA
ATCGTCTGAATAACTCCAAAATCTACATCAACGGCCGTCTGATCGACCAGAAAC
CGATCTCCAATCTGGGTAACATCCACGCTTCTAATAACATCATGTTCAAACTGG
ACGGTTGTCGTGACACTCACCGCTACATCTGGATCAAATACTTCAATCTGTTCGA
CAAAGAACTGAACGAAAAGAAATCAAAGACCTGTACGACAACCAGTCCAATT
CTGGTATCCTGAAAGACTTCTGGGGTGACTACCTGCAGTACGACAAACCGTACT
ACATGCTGAATCTGTACGATCCGAACAAATACGTTGACGTCAACAATGTAGGTA
TCCGCGGTTACATGTACCTGAAAGGTCCGCGTGGTTCTGTTATGACTACCAACAT
CTACCTGAACTCTTCCCTGTACCGTGGTACCAAATTCATCATCAAGAAATACGC
GTCTGGTAACAAGGACAATATCGTTCGCAACAATGATCGTGTATACATCAATGT
TGTAGTTAAGAACAAAGAATACCGTCTGGCTACCAATGCTTCTCAGGCTGGTGT
AGAAAAGATCTTGTCTGCTCTGGAAATCCCGGACGTTGGTAATCTGTCTCAGGT
AGTTGTAATGAAATCCAAGAACGACCAGGGTATCACTAACAAATGCAAAATGA
ATCTGCAGGACAACAATGGTAACGATATCGGTTTCATCGGTTTCCACCAGTTCA
ACAATATCGCTAAACTGGTTGCTTCCAACTGGTACAATCGTCAGATCGAACGTT
CCTCTCGCACTCTGGGTTGCTCTTGGGAGTTCATCCCGGTTGATGACGGTTGGGG
TGAACGTCCGCTGtaaGAATTC

B: BoNTA(H$_C$) encoded protein (Version #2) SEQ ID NO: 4

MSTFTEYIKNIINTSILNLRYESNHLIDLSRYASKINIGSKVNFDPIDKNQIQLFNLESS
KIEVILKNAIVYNSMYENFSTSFWIRIPKYFNSISLNNEYTIINCMENNSGWKVSLNY
GEIIWTLQDTQEIKQRVVFKYSQMINISDYINRWIFVTITNNRLNNSKIYINGRLIDQK
PISNLGNIHASNNIMFKLDGCRDTHRYIWIKYFNLFDKELNEKEIKDLYDNQSNSGIL
KDFWGDYLQYDKPYYMLNLYDPNKYVDVNNVGIRGYMYLKGPRGSVMTTNIYL
NSSLYRGTKFIIKKYASGNKDNIVRNNDRVYINVVVKNKEYRLATNASQAGVEKIL
SALEIPDVGNLSQVVVMKSKNDQGITNKCKMNLQDNNGNDIGFIGFHQFNNIAKLV
ASNWYNRQIERSSRTLGCSWEFIPVDDGWGERPL*

FIGURE 3

A: BoNTA(H$_C$) synthetic gene (Version #3) SEQ ID NO: 5

GAATTCGAAACGatgGCCTCTACCTTCACTGAATACATCAAGAACATCATCAATA
CCTCCATCCTGAACCTGCGCTACGAATCCAATCACCTGATCGACCTGTCTCGCTA
CGCTTCCAAAATCAACATCGGTTCTAAAGTTAACTTCGATCCGATCGACAAGAA
TCAGATCCAGCTGTTCAATCTGGAATCTTCCAAAATCGAAGTTATCCTGAAGAA
TGCTATCGTATACAACTCTATGTACGAAAACTTCTCCACCTCCTTCTGGATCCGT
ATCCCGAAATACTTCAACTCCATCTCTCTGAACAATGAATACACCATCATCAACT
GCATGGAAAACAATTCTGGTTGGAAAGTATCTCTGAACTACGGTGAAATCATCT
GGACTCTGCAGGACACTCAGGAAATCAAACAGCGTGTTGTATTCAAATACTCTC
AGATGATCAACATCTCTGACTACATCAATCGCTGGATCTTCGTTACCATCACCAA
CAATCGTCTGAATAACTCCAAAATCTACATCAACGGCCGTCTGATCGACCAGAA
ACCGATCTCCAATCTGGGTAACATCCACGCTTCTAATAACATCATGTTCAAACTG
GACGGTTGTCGTGACACTCACCGCTACATCTGGATCAAATACTTCAATCTGTTCG
ACAAAGAACTGAACGAAAAGAAATCAAAGACCTGTACGACAACCAGTCCAAT
TCTGGTATCCTGAAAGACTTCTGGGGTGACTACCTGCAGTACGACAAACCGTAC
TACATGCTGAATCTGTACGATCCGAACAAATACGTTGACGTCAACAATGTAGGT
ATCCGCGGTTACATGTACCTGAAAGGTCCGCGTGGTTCTGTTATGACTACCAAC
ATCTACCTGAACTCTTCCCTGTACCGTGGTACCAAATTCATCATCAAGAAATACG
CGTCTGGTAACAAGGACAATATCGTTCGCAACAATGATCGTGTATACATCAATG
TTGTAGTTAAGAACAAAGAATACCGTCTGGCTACCAATGCTTCTCAGGCTGGTG
TAGAAAAGATCTTGTCTGCTCTGGAAATCCCGGACGTTGGTAATCTGTCTCAGG
TAGTTGTAATGAAATCCAAGAACGACCAGGGTATCACTAACAAATGCAAAATG
AATCTGCAGGACAACAATGGTAACGATATCGGTTTCATCGGTTTCCACCAGTTC
AACAATATCGCTAAACTGGTTGCTTCCAACTGGTACAATCGTCAGATCGAACGT
TCCTCTCGCACTCTGGGTTGCTCTTGGGAGTTCATCCCGGTTGATGACGGTTGGG
GTGAACGTCCGCTGtaaGAATTC

B: BoNTA(H$_C$) encoded protein (Version #3) SEQ ID NO: 6

MASTFTEYIKNIINTSILNLRYESNHLIDLSRYASKINIGSKVNFDPIDKNQIQLFNLES
SKIEVILKNAIVYNSMYENFSTSFWIRIPKYFNSISLNNEYTIINCMENNSGWKVSLNY
GEIIWTLQDTQEIKQRVVFKYSQMINISDYINRWIFVTITNNRLNNSKIYINGRLIDQK
PISNLGNIHASNNIMFKLDGCRDTHRYIWIKYFNLFDKELNEKEIKDLYDNQSNSGIL
KDFWGDYLQYDKPYYMLNLYDPNKYVDVNNVGIRGYMYLKGPRGSVMTTNIYL
NSSLYRGTKFIIKKYASGNKDNIVRNNDRVYINVVVKNKEYRLATNASQAGVEKIL
SALEIPDVGNLSQVVVMKSKNDQGITNKCKMNLQDNNGNDIGFIGFHQFNNIAKLV
ASNWYNRQIERSSRTLGCSWEFIPVDDGWGERPL*

FIGURE 4

A: BoNTB(H_C) synthetic gene SEQ ID NO: 7

GAATTCACGatgGCCAACAAATACAATTCCGAAATCCTGAACAATATCATCCTGA
ACCTGCGTTACAAAGACAACAATCTGATCGATCTGTCTGGTTACGGTGCTAAAG
TTGAAGTATACGACGGTGTTGAACTGAATGACAAGAACCAGTTCAAACTGACCT
CTTCCGCTAACTCTAAGATCCGTGTTACTCAGAATCAGAACATCATCTTCAACTC
CGTATTCCTGGACTTCTCTGTTTCCTTCTGGATTCGTATCCCGAAATACAAGAAC
GACGGTATCCAGAATTACATCCACAATGAATACACCATCATCAACTGCATGAAG
AATAACTCTGGTTGGAAGATCTCCATCCGCGGTAACCGTATCATCTGGACTCTG
ATCGATATCAACGGTAAGACCAAATCTGTATTCTTCGAATACAACATCCGTGAA
GACATCTCTGAATACATCAATCGCTGGTTCTTCGTTACCATCACCAATAACCTGA
ACAATGCTAAAATCTACATCAACGGTAAACTGGAATCTAATACCGACATCAAAG
ACATCCGTGAAGTTATCGCTAACGGTGAAATCATCTTCAAACTGGACGGTGACA
TCGATCGTACCCAGTTCATCTGGATGAAATACTTCTCCATCTTCAACACCGAACT
GTCTCAGTCCAATATCGAAGAACGGTACAAGATCCAGTCTTACTCCGAATACCT
GAAAGACTTCTGGGGTAATCCGCTGATGTACAACAAAGAATACTATATGTTCAA
TGCTGGTAACAAGAACTCTTACATCAAACTGAAGAAAGACTCTCCGGTTGGTGA
AATCCTGACTCGTTCCAAATACAACCAGAACTCTAAATACATCAACTACCGCGA
CCTGTACATCGGTGAAAAGTTCATCATCCGTCGCAAATCTAACTCTCAGTCCATC
AATGATGACATCGTACGTAAAGAAGACTACATCTACCTGGACTTCTTCAACCTG
AATCAGGAATGGCGTGTATACACCTACAAGTACTTCAAGAAAGAAGAAGAAAAA
GCTTTTCCTGGCTCCGATCTCTGATTCCGACGAACTCTACAACACCATCCAGATC
AAAGAATACGACGAACAGCCGACCTACTCTTGCCAGCTGCTGTTCAAGAAAGAT
GAAGAATCTACTGACGAAATCGGTCTGATCGGTATCCACCGTTTCTACGAATCT
GGTATCGTATTCGAAGAATACAAAGACTACTTCTGCATCTCCAAATGGTACCTG
AAGGAAGTTAAACGCAAACCGTACAACCTGAAACTGGGTTGCAATTGGCAGTTC
ATCCCGAAAGACGAAGGTTGGACCGAAtagtaaGAATTC

B: BoNTB(H_C) encoded protein SEQ ID NO: 8

MANKYNSEILNNIILNLRYKDNNLIDLSGYGAKVEVYDGVELNDKNQFKLTSSANS
KIRVTQNQNIIFNSVFLDFSVSFWIRIPKYKNDGIQNYIHNEYTIINCMKNNSGWKISI
RGNRIIWTLIDINGKTKSVFFEYNIREDISEYINRWFFVTITNNLNNAKIYINGKLESNT
DIKDIREVIANGEIIFKLDGDIDRTQFIWMKYFSIFNTELSQSNIEERYKIQSYSEYLKD
FWGNPLMYNKEYYMFNAGNKNSYIKLKKDSPVGEILTRSKYNQNSKYINYRDLYI
GEKFIIRRKSNSQSINDDIVRKEDYIYLDFFNLNQEWRVYTYKYFKKEEEKLFLAPIS
DSDELYNTIQIKEYDEQPTYSCQLLFKKDEESTDEIGLIGIHRFYESGIVFEEYKDYFCI
SKWYLKEVKRKPYNLKLGCNWQFIPKDEGWTE**

FIGURE 5

A: BoNTC₁(H_C) synthetic gene SEQ ID NO: 9

GAATTCACGatgACCATCCCATTCAACATCTTCTCCTACACCAACAACTCCCTGTT
GAAGGACATCATCAACGAGTACTTCAACAACATCAACGACTCCAAGATCCTGTC
CCTGCAGAACCGTAAGAACACCTTGGTCGACACCTCCGGTTACAACGCCGAGGT
CTCCGAGGAGGGTGACGTCCAGCTGAACCCAATCTTCCCATTCGACTTCAAGCT
GGGTTCCTCCGGTGAGGACAGAGGTAAGGTCATCGTCACCCAGAACGAGAACA
TCGTCTACAACTCCATGTACGAGTCCTTCTCCATCTCCTTCTGGATCAGAATCAA
CAAGTGGGTCTCCAACTTGCCAGGTTACACCATCATCGACTCCGTCAAGAACAA
CTCCGGTTGGTCCATCGGTATCATCTCCAACTTCCTGGTCTTCACCCTGAAGCAG
AACGAGGACTCCGAGCAGTCCATCAACTTCTCCTACGACATCTCCAACAACGCT
CCTGGTTACAACAAGTGGTTCTTCGTCACCGTCACCAACAACATGATGGGTAAC
ATGAAGATCTACATCAACGGTAAGCTGATCGACACCATCAAGGTCAAGGAGTTG
ACCGGTATCAACTTCTCCAAGACCATCACCTTCGAGATCAACAAGATCCCAGAC
ACCGGTCTGATCACCTCCGACTCCGACAACATCAACATGTGGATCCGTGACTTC
TACATCTTCGCCAAGGAGTTGGACGGTAAGGACATCAACATCCTGTTCAACTCC
TTGCAGTACACCAACGTCGTCAAGGACTACTGGGGTAACGACCTGAGATACAAC
AAGGAGTACTACATGGTCAACATCGACTACTTGAACAGATACATGTACGCCAAC
TCCAGACAGATCGTCTTCAACACCAGACGTAACAACAACGACTTCAACGAGGGT
TACAAGATCATCATCAAGCGTATCAGAGGTAACACCAACGACACCAGAGTCAG
AGGTGGTGACATCCTGTACTTCGACATGACTATCAACAACAAGGCCTACAACCT
GTTCATGAAGAACGAGACCATGTACGCCGACAACCACTCCACCGAGGACATCTA
CGCCATCGGTCTGCGTGAGCAGACCAAGGACATCAACGACAACATCATCTTCCA
GATCCAGCCAATGAACAACACTTACTACTACGCTTCCCAGATCTTCAAGTCCAA
CTTCAACGGTGAGAACATCTCCGGTATCTGTTCCATCGGTACCTACAGATTCCGT
CTGGGTGGTGACTGGTACAGACACAACTACTTGGTTCCAACTGTCAAGCAGGGT
AACTACGCCTCCTTGCTGGAGTCCACTTCCACCCACTGGGGATTCGTCCCAGTCT
CCGAGtaatagGAATTC B: BoNTC₁(H_C) encoded protein SEQ ID NO: 10

MTIPFNIFSYTNNSLLKDIINEYFNNINDSKILSLQNRKNTLVDTSGYNAEVSEEGDV
QLNPIFPFDFKLGSSGEDRGKVIVTQNENIVYNSMYESFSISFWIRINKWVSNLPGYTI
IDSVKNNSGWSIGIISNFLVFTLKQNEDSEQSINFSYDISNNAPGYNKWFFVTVTNNM
MGNMKIYINGKLIDTIKVKELTGINFSKTITFEINKIPDTGLITSDSDNINMWIRDFYIF
AKELDGKDINILFNSLQYTNVVKDYWGNDLRYNKEYYMVNIDYLNRYMYANSRQI
VFNTRRNNNDFNEGYKIIIKRIRGNTNDTRVRGGDILYFDMTINNKAYNLFMKNET
MYADNHSTEDIYAIGLREQTKDINDNIIFQIQPMNNTYYYASQIFKSNFNGENISGICS
IGTYRFRLGGDWYRHNYLVPTVKQGNYASLLESTSTHWGFVPVSE**

FIGURE 6

A: BoNTD(H<sub>C</sub>) synthetic gene SEQ ID NO: 11

GAATTCACGatgCGTTTGAAGGCTAAGGTCAACGAGTCCTTCGAGAACACCATGC
CATTCAACATCTTCTCCTACACCAACAACTCCTTGTTGAAGGACATCATCAACGA
GTACTTCAACTCCATCAACGACTCCAAGATCTTGTCCTTGCAGAACAAGAAGAA
CGCCTTGGTCGACACCTCCGGTTACAACGCCGAGGTCAGAGTCGGTGACAACGT
CCAGTTGAACACCATCTACACCAACGACTTCAAGTTGTCCTCTTCCGGTGACAA
GATCATCGTCAACTTGAACAACAACATCTTGTACTCCGCCATCTACGAGAACTC
CTCTGTCTCCTTCTGGATCAAGATCTCCAAGGACTTGACCAACTCCCACAACGA
GTACACCATCATCAACTCCATCGAGCAGAACTCCGGTTGGAAGTTGTGTATCCG
TAACGGTAACATCGAGTGGATCTTGCAGGACGTCAACCGTAAGTACAAGTCCTT
GATCTTCGACTACTCCGAGTCCTTGTCCCACACCGGTTACACCAACAAGTGGTTC
TTCGTCACCATCACCAACAACATCATGGGTTACATGAAGTTGTACATCAACGGT
GAGTTGAAGCAGTCCCAGAAGATCGAGGACCTGGACGAGGTCAAGCTGGACAA
GACCATCGTCTTCGGTATCGACGAGAACATCGACGAGAACCAGATGTTGTGGAT
CCGTGACTTCAACATCTTCTCCAAGGAGCTGTCCAACGAGGACATCAACATCGT
CTACGAGGGTCAGATCCTGAGGAACGTCATCAAGGACTACTGGGGTAACCCACT
GAAGTTCGACACCGAGTACTACATCATCAACGACAACTACATCGACCGTTACAT
CGCCCCAGAGTCCAACGTCCTGGTCCTGGTCCAGTACCCTGACCGTTCCAAGCT
GTACACCGGTAACCCTATCACCATCAAGTCCGTCTCCGACAAGAACCCTTACTC
CCGTATCCTGAACGGTGACAACATCATCCTGCACATGCTGTACAACTCCCGTAA
GTACATGATCATCCGTGACACCGACACCATCTACGCCACCCAGGGTGGTGACTG
TTCCCAGAACTGTGTCTACGCCCTGAAGCTGCAGTCCAACCTGGGTAACTACGG
TATCGGTATCTTCTCCATCAAGAACATCGTCTCCAAGAACAAGTACTGCTCCCA
GATCTTCTCCTCCTTCCGTGAGAACACCATGCTGCTGGCCGACATCTACAAGCCT
TGGCGTTTCTCCTTCAAGAACGCCTACACTCCTGTCGCCGTCACCAACTACGAGA
CCAAGCTGCTGTCCACCTCCTCCTTCTGGAAGTTCATCTCCCGTGACCCAGGTTG
GGTCGAGtaatagGAATTC B: BoNTD(H<sub>C</sub>) encoded protein SEQ ID NO: 12

MRLKAKVNESFENTMPFNIFSYTNNSLLKDIINEYFNSINDSKILSLQNKKNALVDTS
GYNAEVRVGDNVQLNTIYTNDFKLSSSGDKIIVNLNNNILYSAIYENSSVSFWIKISK
DLTNSHNEYTIINSIEQNSGWKLCIRNGNIEWILQDVNRKYKSLIFDYSESLSHTGYT
NKWFFVTITNNIMGYMKLYINGELKQSQKIEDLDEVKLDKTIVFGIDENIDENQML
WIRDFNIFSKELSNEDINIVYEGQILRNVIKDYWGNPLKFDTEYYIINDNYIDRYIAPE
SNVLVLVQYPDRSKLYTGNPITIKSVSDKNPYSRILNGDNIILHMLYNSRKYMIIRDT
DTIYATQGGDCSQNCVYALKLQSNLGNYGIGIFSIKNIVSKNKYCSQIFSSFRENTML
LADIYKPWRFSFKNAYTPVAVTNYETKLLSTSSFWKFISRDPGWVE**

FIGURE 7

A: BoNTE(H$_C$) synthetic gene SEQ ID NO: 13

GAATTCACCatgGGAGAGAGTCAGCAAGAACTAAATTCTATGGTAACTGATACCC
TAAATAATAGTATTCCTTTTAAGCTTTCTTCTTATACAGATGATAAAATTTTAAT
TTCCTACTTCAACAAGTTCTTCAAGAGAATTAAGTCTTCTTCCGTTTTAAACATG
AGATACAAGAATGATAAATACGTCGACACTTCCGGTTACGACTCCAATATCAAC
ATTAACGGTGACGTGTACAAGTACCCAACTAACAAAACCAATTCGGTATCTAC
AACGACAAGCTTACTGAGCTGAACATCTCTCAAAACGACTACATTATCTACGAC
AACAAGTACAAGAACTTCTCTATTTCTTTCTGGGTCAGGATTCCTAACTACGACA
ACAAGATCGTCAACGTTAACAACGAGTACACTATCATCAACTGTATGAGAGACA
ACAACTCCGGTTGGAAGGTCTCTCTTAACCACAACGAGATCATTTGGACCTTGC
AAGACAACGCAGGTATTAACCAAAAGTTAGCATTCAACTACGGTAACGCAAAC
GGTATTTCTGACTACATCAACAAGTGGATTTTCGTCACTATCACTAACGACAGAT
TAGGTGACTCTAAGCTTTACATTAACGGTAACTTAATCGACCAAAAGTCCATTTT
AAACTTAGGTAACATTCACGTTTCTGACAACATCTTATTCAAGATCGTTAACTGC
AGTTACACCAGATACATTGGCATTAGATACTTCAACATTTTCGACAAGGAGTTA
GACGAGACCGAGATTCAAACTTTATACAGCAACGAACCTAACACCAATATTTTG
AAGGACTTCTGGGGTAACTACTTGCTTTACGACAAGGAATACTACTTATTAAAC
GTGTTAAAGCCAAACAACTTCATTGATAGGAGAAAGGATTCTACTTTAAGCATT
AACAACATCAGAAGCACTATTCTTTTAGCTAACAGATTATACTCTGGTATCAAG
GTTAAGATCCAAAGAGTTAACAACTCTTCTACTAACGATAACCTTGTTAGAAAG
AACGATCAGGTCTATATTAACTTCGTCGCTAGCAAGACTCACTTATTCCCATTAT
ATGCTGATACCGCTACCACCAACAAGGAGAAGACCATCAAGATCTCCTCCTCTG
GCAACAGATTTAACCAAGTCGTCGTTATGAACTCCGTCGGTAACAACTGTACCA
TGAACTTTAAAAATAATAATGGAAATAATATTGGGTTGTTAGGTTTCAAGGCAG
ATACTGTAGTTGCTAGTACTTGGTATTATACCCACATGAGAGATCACACCAACA
GCAATGGATGTTTTGGAACTTTATTTCTGAAGAACATGGATGGCAAGAAAAta
a
TagGGATCC GCGGCCGC ACGCGT CCCGGG ACTAGT GAATTC

B: BoNTE(H$_C$) encoded protein SEQ ID NO: 14

MGESQQELNSMVTDTLNNSIPFKLSSYTDDKILISYFNKFFKRIKSSSVLNMRYKND
KYVDTSGYDSNININGDVYKYPTNKQFGIYNDKLTELNISQNDYIIYDNKYKNFSIS
FWVRIPNYDNKIVNVNNEYTIINCMRDNNSGWKVSLNHNEIIWTLQDNAGINQKLA
FNYGNANGISDYINKWIFVTITNDRLGDSKLYINGNLIDQKSILNLGNIHVSDNILFKI
VNCSYTRYIGIRYFNIFDKELDETEIQTLYSNEPNTNILKDFWGNYLLYDKEYYLLN
VLKPNNFIDRRKDSTLSINNIRSTILLANRLYSGIKVKIQRVNNSSTNDNLVRKNDQV
YINFVASKTHLFPLYADTATTNKEKTIKISSSGNRFNQVVVMNSVGNNCTMNFKNN
NGNNIGLLGFKADTVVASTWYYTHMRDHTNSNGCFWNFISEEHGWQEK**

FIGURE 8

AMINO ACID AND DESIGNED NUCLEOTIDE SEQUENCE OF BONTE(Hc)

FIGURE 9

A: BoNTF(H_C) synthetic gene SEQ ID NO: 15

GAATTCACGatgTCCTACACCAACGACAAGATCCTGATCTTGTACTTCAACAAGCTGT
ACAAGAAGATCAAGGACAACTCCATCTTGGACATGAGATACGAAAACAATAAGTTC
ATCGACATCTCCGGTTACGGTTCCAACATCTCCATCAACGGTGACGTCTACATCTAC
TCCACCAATAGAAACCAGTTCGGAATCTACTCCTCCAAGCCTTCCGAGGTCAACATC
GCTCAGAACAACGACATCATCTACAACGGAAGATACCAGAACTTCTCCATCTCCTTC
TGGGTCCGTATCCCAAAGTACTTCAACAAGGTCAACCTGAATAACGAGTACACCATC
ATCGACTGCATCCGTAACAATAACTCCGGATGGAAGATCTCCCTGAACTACAACAA
GATCATCTGGACCCTGCAGGACACCGCCGGTAACAATCAGAAGTTGGTCTTCAACTA
CACCCAGATGATCTCCATCTCCGACTACATCAACAAGTGGATCTTCGTCACCATCAC
CAATAACCGTTTGGGAAACTCCAGAATCTACATCAACGGTAACTTGATCGACGAGA
AGTCCATCTCCAACTTGGGTGACATCCACGTCTCCGACAACATTTTGTTCAAGATCG
TCGGTTGTAACGACACCCGTTACGTCGGGATCCGTTACTTCAAAGTCTTCGACACTG
AGTTGGGTAAGACCGAGATCGAGACCTTGTACTCCGACGAGCCTGACCCATCCATCC
TGAAGGACTTCTGGGGTAACTACCTGCTGTACAACAAACGTTACTACTTGCTGAACT
TGTTGCGTACCGACAAGTCCATCACCCAGAACTCCAACTTCTTGAACATCAACCAGC
AGAGAGGTGTCTACCAGAAGCCAAACATCTTCTCCAACACCAGATTGTACACCGGA
GTCGAGGTCATTATCAGAAAGAACGGATCTACTGATATTTCCAACACCGATAACTTC
GTCAGAAAGAACGATCTGGCTTACATCAACGTTGTCGACAGAGATGTCGAATACCG
TCTGTACGCCGATATCTCTATCGCCAAACCTGAAAAGATCATCAAGCTGATCCGTAC
CTCTAACTCTAACAACTCTCTGGGACAAATCATCGTCATGGACTCCATCGGTAATAA
CTGTACCATGAACTTCCAGAACAACAACGGTGGAAACATCGGTTTGTTGGGTTTCCA
CTCCAACAACTTGGTCGCTTCCTCCTGGTACTACAACAACATCCGTAAGAACACCTC
CTCCAACGGTTGCTTCTGGTCCTTCATCTCCAAGGAGCACGGTTGGCAGGAGAACtaat
agGAATTC

B: BoNTF(H_C) encoded protein SEQ ID NO: 16

MSYTNDKILILYFNKLYKKIKDNSILDMRYENNKFIDISGYGSNISINGDVYIYSTNRNQF
GIYSSKPSEVNIAQNNDIIYNGRYQNFSISFWVRIPKYFNKVNLNNEYTIIDCIRNNNSGW
KISLNYNKIIWTLQDTAGNNQKLVFNYTQMISISDYINKWIFVTITNNRLGNSRIYINGNLI
DEKSISNLGDIHVSDNILFKIVGCNDTRYVGIRYFKVFDTELGKTEIETLYSDEPDPSILKD
FWGNYLLYNKRYYLLNLLRTDKSITQNSNFLNINQQRGVYQKPNIFSNTRLYTGVEVIIR
KNGSTDISNTDNFVRKNDLAYINVVDRDVEYRLYADISIAKPEKIIKLIRTSNSNNSLGQII
VMDSIGNNCTMNFQNNNGGNIGLLGFHSNNLVASSWYYNNIRKNTSSNGCFWSFISKE
HGWQEN**

FIGURE 10

A: BoNTG(H_C) synthetic gene SEQ ID NO: 17

GAATTCACGatgAAGGACACCATCCTGATCCAGGTCTTCAACAACTACATCTCCAACA
TCTCCTCCAACGCCATCCTGTCCCTGTCCTACCGTGGTGGTCGTCTGATCGACTCCTC
CGGTTACGGAGCCACCATGAACGTCGGTTCCGACGTCATCTTCAACGACATCGGTAA
CGGTCAGTTCAAGCTGAACAACTCCGAGAACTCCAACATCACCGCCCACCAGTCCA
AGTTCGTCGTCTACGACTCCATGTTCGACAACTTCTCCATCAACTTCTGGGTCCGTAC
CCCAAAGTACAACAACAACGACATCCAGACCTACCTGCAGAACGAGTACACCATCA
TCTCCTGTATCAAGAACGACTCCGGTTGGAAGGTCTCCATCAAGGGAAACCGTATCA
TCTGGACCCTGATCGACGTCAACGCCAAGTCCAAGTCCATCTTCTTCGAGTACTCCA
TCAAGGACAACATCTCCGACTACATCAACAAGTGGTTCTCCATCACCATCACCAACG
ACCGTCTGGGTAACGCCAACATCTACATCAACGGTTCCCTGAAGAAGTCCGAGAAG
ATCCTGAACCTGGACCGTATCAACTCCTCCAACGACATCGACTTCAAGCTGATCAAC
TGTACCGACACCACCAAGTTCGTCTGGATCAAGGACTTCAACATCTTCGGTCGTGAG
CTGAACGCCACCGAGGTCTCCTCCCTGTACTGGATCCAGTCCTCCACCAACACCCTG
AAGGACTTCTGGGGAAACCCACTGCGTTACGACACCCAGTACTACCTGTTCAACCAG
GGTATGCAGAACATCTACATCAAGTACTTCTCCAAGGCCTCCATGGGTGAGACCGCC
CCTCGTACCAACTTCAACAACGCCGCCATCAACTACCAGAACCTGTACCTGGGTCTG
CGTTTCATCATCAAGAAGGCCTCCAACTCCCGTAACATCAACAACGACAACATCGTC
CGTGAGGGTGACTACATCTACCTGAACATCGACAACATCTCCGACGAGTCCTACCGT
GTCTACGTCCTGGTCAACTCCAAGGAGATCCAGACCCAGCTGTTCCTGGCCCCAATC
AACGACGACCCTACCTTCTACGACGTCCTGCAGATCAAGAAGTACTACGAGAAGAC
CACCTACAACTGTCAGATCCTGTGCGAGAAGGACACCAAGACCTTCGGACTGTTCG
GTATCGGTAAGTTCGTCAAGGACTACGGTTACGTCTGGGACACCTACGACAACTACT
TCTGTATCTCCCAGTGGTACCTGCGTCGTATCTCCGAGAACATCAACAAGCTGCGTC
TGGGATGTAACTGGCAGTTCATCCCAGTCGACGAGGGTTGGACCGAGtaatagGAATTC B: BoNTG(H_C) encoded protein SEQ ID NO: 18

MKDTILIQVFNNYISNISSNAILSLSYRGGRLIDSSGYGATMNVGSDVIFNDIGNGQFKLN
NSENSNITAHQSKFVVYDSMFDNFSINFWVRTPKYNNNDIQTYLQNEYTIISCIKNDSGW
KVSIKGNRIIWTLIDVNAKSKSIFFEYSIKDNISDYINKWFSITITNDRLGNANIYINGSLKK
SEKILNLDRINSSNDIDFKLINCTDTTKFVWIKDFNIFGRELNATEVSSLYWIQSSTNTLKD
FWGNPLRYDTQYYLFNQGMQNIYIKYFSKASMGETAPRTNFNNAAINYQNLYLGLRFII
KKASNSRNINNDNIVREGDYIYLNIDNISDESYRVYVLVNSKEIQTQLFLAPINDDPTFYD
VLQIKKYYEKTTYNCQILCEKDTKTFGLFGIGKFVKDYGYVWDTYDNYFCISQWYLRRI
SENINKLRLGCNWQFIPVDEGWTE**

FIGURE 11

A: BoNTA(H$_N$) synthetic gene SEQ ID NO: 19 atgGCTCTGAACGACCTGTGCATCAAAGTTAACAACTGGGACCTGTTCTTCTCCCCGTC
TGAAGACAACTTCACTAACGACCTGAACAAAGGCGAAGAAATCACCTCCGACACTA
ACATCGAAGCTGCTGAAGAAAACATCTCTCTGGACCTGATCCAGCAGTACTACCTGA
CTTTCAACTTCGACAACGAACCGGAAAACATCTCCATCGAAACCTGTCTTCCGACA
TCATCGGTCAGCTGGAACTGATGCCGAACATCGAACGCTTCCCGAACGGCAAGAAA
TACGAACTGGACAAATACACCATGTTCCACTACCTGCGTGCTCAGGAATTCGAACAC
GGTAAATCTCGTATCGCTCTGACTAACTCCGTTAACGAAGCTCTGCTGAACCCGTCT
CGCGTTTACACCTTCTTCTCTTCCGACTACGTTAAGAAAGTTAACAAAGCTACTGAA
GCTGCTATGTTCCTGGGTTGGGTTGAACAGCTGGTTTACGACTTCACCGACGAAACT
TCTGAAGTTTCCACCACTGACAAAATCGCTGACATCACTATCATCATCCCGTACATC
GGCCCGGCTCTGAACATCGGTAACATGCTGTACAAAGACGACTTCGTTGGTGCTCTG
ATCTTCTCTGGCGCTGTTATCCTGCTGGAATTCATCCCGGAAATCGCTATCCCGGTTC
TGGGTACCTTCGCTCTGGTTTCCTACATCGCTAACAAAGTTCTGACTGTTCAGACCAT
CGACAACGCTCTGTCTAAACGTAACGAAAAATGGGACGAAGTTTACAAATACATCG
TTACTAACTGGCTGGCTAAAGTTAACACTCAGATCGACCTGATCCGTAAGAAGATGA
AAGAAGCTCTGGAAAACCAGGCTGAAGCTACTAAAGCTATCATCAACTACCAGTAC
AACCAGTACACCGAAGAAGAAAAGAACAACATCAACTTCAACATCGATGACCTGTC
CTCTAAACTGAACGAATCCATCAACAAAGCTATGATCAACATCAACAAATTCCTGAA
CCAGTGCTCTGTTTCCTACCTGATGAACTCTATGATCCCGTACGGCGTTAAACGCCTG
GAAGACTTCGACGCTTCCCTGAAAGACGCTCTGCTGAAATACATCCGTGACAACTAC
GGTACTCTGATCGGCCAGGTTGACCGTCTGAAAGACAAGGTTAACAACACCCTGTCT
ACTGACATCCCGTTCCAGCTGTCCAAATACGTTGACAACCAGtaa

B: BoNTA(H$_N$) encoded protein SEQ ID NO: 20

MALNDLCIKVNNWDLFFSPSEDNFTNDLNKGEEITSDTNIEAAEENISLDLIQQYYLTFNF
DNEPENISIENLSSDIIGQLELMPNIERFPNGKKYELDKYTMFHYLRAQEFEHGKSRIALT
NSVNEALLNPSRVYTFFSSDYVKKVNKATEAAMFLGWVEQLVYDFTDETSEVSTTDKI
ADITIIIPYIGPALNIGNMLYKDDFVGALIFSGAVILLEFIPEIAIPVLGTFALVSYIANKVLT
VQTIDNALSKRNEKWDEVYKYIVTNWLAKVNTQIDLIRKKMKEALENQAEATKAIINY
QYNQYTEEEKNNINFNIDDLSSKLNESINKAMININKFLNQCSVSYLMNSMIPYGVKRLE
DFDASLKDALLKYIRDNYGTLIGQVDRLKDKVNNTLSTDIPFQLSKYVDNQ*

FIGURE 12

A: BoNTB(H$_N$) synthetic gene SEQ ID NO: 21 atgGCTCCAGGAATCTGTATCGACGTCGACAACGAGGACTTGTTCTTCATCGCTGACA
AGAACTCCTTCTCCGACGACTTGTCCAAGAACGAGAGAATCGAGTACAACACCCAG
TCCAACTACATCGAGAACGACTTCCCAATCAACGAGTTGATCTTGGACACCGACTTG
ATCTCCAAGATCGAGTTGCCATCCGAGAACACCGAGTCCTTGACTGACTTCAACGTC
GACGTCCCAGTCTACGAGAAGCAACCAGCTATCAAGAAGATTTTCACCGACGAGAA
CACCATCTTCCAATACCTGTACTCTCAGACCTTCCCTTTGGACATCAGAGACATCTCC
TTGACCTCTTCCTTCGACGACGCCCTGCTGTTCTCCAACAAGGTCTACTCCTTCTTCT
CCATGGACTACATCAAGACTGCTAACAAGGTCGTCGAGGCCGGTTTGTTCGCTGGTT
GGGTCAAGCAGATCGTCAACGATTTCGTCATCGAGGCTAACAAGTCCAACACCATG
GACAAGATTGCCGACATCTCCTTGATTGTCCCATACATCGGTTTGGCCTTGAACGTC
GGTAACGAGACCGCCAAGGGTAACTTCGAGAACGCTTTCGAGATCGCTGGTGCCTC
CATCTTGTTGGAGTTCATCCCAGAGTTGTTGATCCCAGTCGTCGGTGCCTTCTTGTTG
GAGTCCTACATCGACAACAAGAACAAGATCATCAAGACCATCGACAACGCTTTGAC
CAAGAGAAACGAGAAGTGGTCCGACATGTACGGTTTGATCGTCGCCCAATGGTTGT
CCACCGTCAACACCCAATTCTACACCATCAAGGAGGGTATGTACAAGGCCTTGAACT
ACCAGGCCCAAGCTTTGGAGGAGATCATCAAGTACAGATACAACATCTACTCCGAG
AAGGAGAAGTCCAACATTAACATCGACTTCAACGACATCAACTCCAAGCTGAACGA
GGGTATTAACCAGGCCATCGACAACATCAACAACTTCATCAACGGTTGTTCCGTCTC
CTACTTGATGAAGAAGATGATTCCATTGGCCGTCGAGAAGTTGTTGGACTTCGACAA
CACCCTGAAGAAGAACTTGTTGAACTACATCGACGAGAACAAGTTGTACTTGATCG
GTTCCGCTGAGTACGAGAAGTCCAAGGTCAACAAGTACTTGAAGACCATCATGCCA
TTCGACTTGTCCATCTACACCAACGACACCATCTTGATCGAGATGTTCtaa

B: BoNTB(H$_N$) encoded protein SEQ ID NO: 22

MAPGICIDVDNEDLFFIADKNSFSDDLSKNERIEYNTQSNYIENDFPINELILDTDLISKIEL
PSENTESLTDFNVDVPVYEKQPAIKKIFTDENTIFQYLYSQTFPLDIRDISLTSSFDDALLFS
NKVYSFFSMDYIKTANKVVEAGLFAGWVKQIVNDFVIEANKSNTMDKIADISLIVPYIGL
ALNVGNETAKGNFENAFEIAGASILLEFIPELLIPVVGAFLLESYIDNKNKIIKTIDNALTK
RNEKWSDMYGLIVAQWLSTVNTQFYTIKEGMYKALNYQAQALEEIIKYRYNIYSEKEK
SNINIDFNDINSKLNEGINQAIDNINNFINGCSVSYLMKKMIPLAVEKLLDFDNTLKKNLL
NYIDENKLYLIGSAEYEKSKVNKYLKTIMPFDLSIYTNDTILIEMF*

FIGURE 13

A: BoNTC$_1$(H$_N$) synthetic gene SEQ ID NO: 23 atgTCCCTGTACAACAAGACCCTTGACTGTAGAGAGCTGCTGGTGAAGAACACTGACC
TGCCATTCATCGGTGACATCAGTGACGTGAAGACTGACATCTTCCTGCGTAAGGACA
TCAACGAGGAGACTGAGGTGATCTACTACCCAGACAACGTGTCAGTAGACCAAGTG
ATCCTCAGTAAGAACACCTCCGAGCATGGACAACTAGACCTGCTCTACCCTAGTATC
GACAGTGAGAGTGAGATCCTGCCAGGGGAGAATCAAGTCTTCTACGACAACCGTAC
CCAGAACGTGGACTACCTGAACTCCTACTACTACCTAGAGTCTCAGAAGCTGAGTGA
CAACGTGGAGGACTTCACTTTCACGCGTTCAATCGAGGAGGCTCTGGACAACAGTGC
AAAGGTGTACACTTACTTCCCTACCCTGGCTAACAAGGTGAATGCCGGTGTGCAAGG
TGGTCTGTTCCTGATGTGGGCAAACGACGTGGTTGAGGACTTCACTACCAACATCCT
GCGTAAGGACACACTGGACAAGATCTCAGATGTGTCAGCTATCATCCCCTACATCGG
ACCCGCACTGAACATCTCCAACTCTGTGCGTCGTGGAAACTTCACTGAGGCATTCGC
AGTCACTGGTGTCACCATCCTGCTGGAGGCATTCCCTGAGTTCACAATCCCTGCTCT
GGGTGCATTCGTGATCTACAGTAAGGTCCAGGAGCGAAACGAGATCATCAAGACCA
TCGACAACTGTCTGGAGCAGAGGATCAAGAGATGGAAGGACTCCTACGAGTGGATG
ATGGGAACGTGGTTGTCCAGGATCATCACCCAGTTCAACAACATCTCCTACCAGATG
TACGACTCCCTGAACTACCAGGCAGGTGCAATCAAGGCTAAGATCGACCTGGAGTA
CAAGAAGTACTCCGGAAGCGACAAGGAGAACATCAAGAGCCAGGTTGAGAACCTG
AAGAACAGTCTGGACGTCAAGATCTCGGAGGCAATGAACAACATCAACAAGTTCAT
CCGAGAGTGCTCCGTCACCTACCTGTTCAAGAACATGCTGCCTAAGGTCATCGACGA
GCTGAACGAGTTCGACCGAAACACCAAGGCAAAGCTGATCAACCTGATCGACTCCC
ATAACATCATCCTGGTCGGTGAGGTCGACAAGCTGAAGGCAAAGGTAAACAACAGC
TTCCAGAACtaa

B: BoNTC$_1$(H$_N$) encoded protein SEQ ID NO: 24

MSLYNKTLDCRELLVKNTDLPFIGDISDVKTDIFLRKDINEETEVIYYPDNVSVDQVILSK
NTSEHGQLDLLYPSIDSESEILPGENQVFYDNRTQNVDYLNSYYYLESQKLSDNVEDFTF
TRSIEEALDNSAKVYTYFPTLANKVNAGVQGGLFLMWANDVVEDFTTNILRKDTLDKIS
DVSAIIPYIGPALNISNSVRRGNFTEAFAVTGVTILLEAFPEFTIPALGAFVIYSKVQERNEII
KTIDNCLEQRIKRWKDSYEWMMGTWLSRIITQFNNISYQMYDSLNYQAGAIKAKIDLEY
KKYSGSDKENIKSQVENLKNSLDVKISEAMNNINKFIRECSVTYLFKNMLPKVIDELNEF
DRNTKAKLINLIDSHNIILVGEVDKLKAKVNNSFQN*

FIGURE 14

A: BoNTD(H$_N$) synthetic gene SEQ ID NO: 25 atggccAACTCCCGTGACGACTCCACCTGCATCAAGGTCAAGAACAACAGACTGCCAT
ACGTTGCCGACAAGGACTCCATCTCCCAGGAGATCTTCGAGAACAAGATCATCACC
GACGAGACCAACGTTCAAAACTACTCCGACAAGTTCTCTTTGGACGAGTCCATCCTG
GACGGTCAGGTCCCAATCAACCCAGAGATCGTCGACCCACTGTTGCCAAACGTCAA
CATGGAGCCATTGAACTTGCCAGGTGAGGAGATCGTCTTCTACGACGACATCACCAA
GTACGTCGACTACTTGAACTCCTACTACTACTTGGAGTCTCAAAAGTTGTCTAACAA
CGTCGAGAACATCACCTTGACCACCTCCGTCGAGGAGGCCTTGGGTTACTCTAACAA
GATCTACACCTTCCTGCCATCCTTGGCTGAGAAGGTTAACAAGGGTGTTCAAGCTGG
TTTGTTCCTGAACTGGGCCAACGAGGTCGTCGAGGACTTCACCACCAACATCATGAA
GAAGGACACCCTGGACAAGATCTCCGACGTCTCCGTCATCATCCCATACATCGGTCC
AGCCTTGAACATCGGTAACTCCGCCCTGAGAGGTAACTTCAACCAGGCCTTCGCCAC
CGCCGGTGTCGCCTTCCTGCTGGAGGGTTTCCCAGAGTTCACCATCCCAGCCCTGGG
TGTCTTCACCTTCTACTCCTCCATCCAGGAGAGAGAGAAGATCATCAAGACCATCGA
GAACTGCTTGGAGCAGAGAGTCAAGAGATGGAAGGACTCCTACCAGTGGATGGTTT
CCAACTGGCTGTCCAGAATCACCACCCAATTCAACCACATCAACTACCAGATGTACG
ACTCCCTGTCCTACCAGGCCGACGCCATCAAGGCCAAGATCGACCTGGAGTACAAG
AAGTACTCCGGTTCCGACAAGGAGAACATCAAGTCCCAGGTCGAGAACCTGAAGAA
CTCCTTGGACGTCAAGATCTCCGAGGCCATGAACAACATCAACAAGTTCATCCGTGA
GTGTTCCGTCACCTACCTGTTCAAGAACATGCTGCCAAAGGTCATCGACGAGCTGAA
CAAGTTCGACCTGAGAACCAAGACCGAGCTGATCAACCTGATCGACTCCCACAACA
TCATCCTGGTTGGTGAGGTTGACtaa B: BoNTD(H$_N$) encoded protein SEQ ID NO: 26

MANSRDDSTCIKVKNNRLPYVADKDSISQEIFENKIITDETNVQNYSDKFSLDESILDGQV
PINPEIVDPLLPNVNMEPLNLPGEEIVFYDDITKYVDYLNSYYYLESQKLSNNVENITLTT
SVEEALGYSNKIYTFLPSLAEKVNKGVQAGLFLNWANEVVEDFTTNIMKKDTLDKISDV
SVIIPYIGPALNIGNSALRGNFNQAFATAGVAFLLEGFPEFTIPALGVFTFYSSIQEREKIIK
TIENCLEQRVKRWKDSYQWMVSNWLSRITTQFNHINYQMYDSLSYQADAIKAKIDLEY
KKYSGSDKENIKSQVENLKNSLDVKISEAMNNINKFIRECSVTYLFKNMLPKVIDELNKF
DLRTKTELINLIDSHNIILVGEVD*

FIGURE 15

A: BoNTE(H$_N$) synthetic gene SEQ ID NO: 27 atgTCCATCTGCATCGAGATCAACAACGGTGAGCTGTTCTTCGTGGCTTCCGAGAACA
GTTACAACGATGACAACATCAACACTCCTAAGGAGATTGACGACACCGTCACTTCTA
ACAACAACTACGAAAACGACCTGGACCAGGTCATCCTAAACTTCAACTCCGAGTCC
GCCCCTGGTCTGTCCGACGAGAAGCTGAACCTGACCATCCAGAACGACGCTTACATC
CCAAAGTACGACTCCAACGGTACATCCGATATCGAGCAGCATGACGTTAACGAGCT
TAACGTCTTCTTCTACTTAGACGCTCAGAAGGTGCCCGAGGGTGAGAACAACGTCAA
TCTCACCTCTTCAATTGACACAGCCTTGTTGGAGCAGCCTAAGATCTACACCTTCTTC
TCCTCCGAGTTCATCAACAACGTCAACAAGCCTGTGCAGGCCGCATTGTTCGTAAGC
TGGATTCAGCAGGTGTTAGTAGACTTCACTACTGAGGCTAACCAGAAGTCCACTGTT
GACAAGATCGCTGACATCTCCATCGTCGTCCCATACATCGGTCTGGCTCTGAACATC
GGCAACGAGGCACAGAAGGGCAACTTCAAGGATGCCCTTGAGTTGTTGGGTGCCGG
TATTTTGTTGGAGTTCGAACCCGAGCTGCTGATCCCTACCATCCTGGTCTTCACGATC
AAGTCCTTCCTGGGTTCCTCCGACAACAAGAACAAGGTCATTAAGGCCATCAACAA
CGCCCTGAAGGAGCGTGACGAGAAGTGGAAGGAAGTCTATTCCTTCATCGTCTCGA
ACTGGATGACCAAGATCAACACCCAGTTCAACAAGCGAAAGGAGCAGATGTACCAG
GCTCTGCAGAACCAGGTCAACGCCATCAAGACCATCATCGAGTCCAAGTACAACTC
CTACACCCTGGAGGAGAAGAACGAGCTTACCAACAAGTACGATATCAAGCAGATCG
AGAACGAGCTGAACCAGAAGGTCTCCATCGCCATGAACAACATCGACAGGTTCCTG
ACCGAGTCCTCCATCTCCTACCTGATGAAGCTCATCAACGAGGTCAAGATCAACAAG
CTGCGAGAGTACGACGAGAATGTCAAGACGTACCTGCTGAACTACATCATCCAGCA
CGGATCCATCCTGtaa

B: BoNTE(H$_N$) encoded protein SEQ ID NO: 28

MSICIEINNGELFFVASENSYNDDNINTPKEIDDTVTSNNNYENDLDQVILNFNSESAPGL
SDEKLNLTIQNDAYIPKYDSNGTSDIEQHDVNELNVFFYLDAQKVPEGENNVNLTSSIDT
ALLEQPKIYTFFSSEFINNVNKPVQAALFVSWIQQVLVDFTTEANQKSTVDKIADISIVVP
YIGLALNIGNEAQKGNFKDALELLGAGILLEFEPELLIPTILVFTIKSFLGSSDNKNKVIKAI
NNALKERDEKWKEVYSFIVSNWMTKINTQFNKRKEQMYQALQNQVNAIKTIIESKYNS
YTLEEKNELTNKYDIKQIENELNQKVSIAMNNIDRFLTESSISYLMKLINEVKINKLREYD
ENVKTYLLNYIIQHGSIL*

FIGURE 16

A: BoNTF(H$_N$) synthetic gene SEQ ID NO: 29 atgGCCCCACCACGTCTGTGTATTAGAGTCAACAACTCAGAATTATTCTTTGTCGCTTC
CGAGTCAAGCTACAACGAGAACGATATTAACACACCTAAAGAGATTGACGATACTA
CCAACCTAAACAACAACTACCGGAACAACTTGGATGAGGTTATTTTGGATTACAACT
CACAGACCATCCCTCAAATTTCCAACCGTACCTTAAACACTCTTGTCCAAGACAACT
CCTACGTTCCAAGATACGATTCTAACGGTACCTCAGAGATCGAGGAGTATGATGTTG
TTGACTTTAACGTCTTTTTCTATTTGCATGCCCAGAAGGTGCCAGAAGGTGAAACCA
ACATCTCATTGACTTCTTCCATTGATACCGCCTTGTTGGAAGAGTCCAAGGATATCTT
CTTTTCTTCGGAGTTTATCGATACTATCAACAAGCCTGTCAACGCCGCTCTGTTCATT
GATTGGATTAGCAAGGTCATCAGAGATTTTACCACTGAAGCTACTCAAAAGTCCACT
GTTGATAAGATTGCTGACATCTCTTTGATTGTCCCCTATGTCGGTCTTGCTTTGAACA
TCATTATTGAGGCAGAAAAGGGTAACTTTGAGGAGGCTTTTGAATTGTTGGGAGTTG
GTATTTTGTTGGAGTTTGTTCCAGAACTTACCATTCCTGTCATTTTAGTTTTTACGATC
AAGTCCTACATCGATTCATACGAGAACAAGAATAAAGCAATTAAAGCTATTAACAA
CTCCTTGATCGAAAGAGAGGCTAAGTGGAAGGAAATCTACTCATGGATTGTATCAA
ACTGGCTTACTAGAATTAACACTCAATTTAACAAGAGAAAGGAGCAAATGTACCAG
GCTCTGCAAAACCAAGTCGATGCTATCAAGACTGCAATTGAATACAAGTACAACAA
CTATACTTCCGATGAGAAGAACAGACTTGAATCTGAATACAATATCAACAACATTGA
AGAAGAGTTGAACAAGAAAGTTTCTTTGGCTATGAAGAATATCGAAAGATTTATGA
CCGAATCCTCTATCTCTTACTTGATGAAGTTGATCAATGAGGCCAAGGTTGGTAAGT
TGAAGAAGTACGATAACCACGTTAAGAGCGATCTGCTGAACTACATTCTCGACCAC
AGATCAATCCTGGGAGAGCAGACAAACGAGCTGAGTGATTTGGTTACTTCCACTTTG
AACTCCTCCATTCCATTTGAGCTTTCTtaa

B: BoNTF(H$_N$) encoded protein SEQ ID NO: 30

MAPPRLCIRVNNSELFFVASESSYNENDINTPKEIDDTTNLNNNYRNNLDEVILDYNSQTI
PQISNRTLNTLVQDNSYVPRYDSNGTSEIEEYDVVDFNVFFYLHAQKVPEGETNISLTSSI
DTALLEESKDIFFSSEFIDTINKPVNAALFIDWISKVIRDFTTEATQKSTVDKIADISLIVPY
VGLALNIIIEAEKGNFEEAFELLGVGILLEFVPELTIPVILVFTIKSYIDSYENKNKAIKAINN
SLIEREAKWKEIYSWIVSNWLTRINTQFNKRKEQMYQALQNQVDAIKTAIEYKYNNYTS
DEKNRLESEYNINNIEEELNKKVSLAMKNIERFMTESSISYLMKLINEAKVGKLKKYDNH
VKSDLLNYILDHRSILGEQTNELSDLVTSTLNSSIPFELS*

FIGURE 17

A: BoNTG(H$_N$) synthetic gene SEQ ID NO: 31 atggccAAAAATACCGGTAAATCTGAACAGTGTATTATTGTTAATAATGAGGATTTATT
TTTCATAGCTAATAAAGATAGTTTTTCAAAAGATTTAGCTAAAGCAGAAACTATAGC
ATATAATACACAAAATAATACTATAGAAAATAATTTTTCTATAGATCAGTTGATTTT
AGATAATGATTTAAGCAGTGGCATAGACTTACCAAATGAAAACACAGAACCATTTA
CAAATTTTGACGACATAGATATCCCTGTGTATATTAAACAATCTGCTTTAAAAAAAA
TTTTTGTGGATGGAGATAGCCTTTTTGAATATTTACATGCTCAAACATTTCCTTCTAA
TATAGAAAATCTACAACTAACGAATTCATTAAATGATGCTTTAAGAAATAATAATAA
AGTCTATACTTTTTTTTCTACAAACCTTGTTGAAAAAGCTAATACAGTTGTAGGTGCT
TCACTTTTTGTAAACTGGGTAAAAGGAGTAATAGATGATTTTACATCTGAATCCACA
CAAAAAAGTACTATAGATAAAGTTTCAGATGTATCCATAATTATTCCCTATATAGGA
CCTGCTTTGAATGTAGGAAATGAAACAGCTAAAGAAATTTTAAAAATGCTTTTGAA
ATAGGTGGAGCCGCTATCTTAATGGAGTTTATTCCAGAACTTATTGTACCTATAGTT
GGATTTTTTACATTAGAATCATATGTAGGAAATAAAGGGCATATTATTATGACGATA
TCCAATGCTTTAAAGAAAAGGGATCAAAAATGGACAGATATGTATGGTTTGATAGT
ATCGCAGTGGCTCTCAACGGTTAATACTCAATTTTATACAATAAAAGAAAGAATGTA
CAATGCTTTAAATAATCAATCACAAGCAATAGAAAAAATAATAGAAGATCAATATA
ATAGATATAGTGAAGAAGATAAAATGAATATTAACATTGATTTTAATGATATAGATT
TTAAACTTAATCAAAGTATAAATTTAGCAATAAACAATATAGATGATTTTATAAACC
AATGTTCTATATCATATCTAATGAATAGAATGATTCCATTAGCTGTAAAAAAGTTAA
AAGACTTTGATGATAATCTTAAGAGAGATTTATTGGAGTATATAGATACAAATGAAC
TATATTTACTTGATGAAGTAAATATTCTAAAATCAAAAGTAAATAGACACCTAAAAG
ACAGTATACCATTTGATCTTTCACTATATACCtaa

B: BoNTG(H$_N$) encoded protein SEQ ID NO: 32

MAKNTGKSEQCIIVNNEDLFFIANKDSFSKDLAKAETIAYNTQNNTIENNFSIDQLILDND
LSSGIDLPNENTEPFTNFDDIDIPVYIKQSALKKIFVDGDSLFEYLHAQTFPSNIENLQLTN
SLNDALRNNNKVYTFFSTNLVEKANTVVGASLFVNWVKGVIDDFTSESTQKSTIDKVSD
VSIIPYIGPALNVGNETAKENFKNAFEIGGAAILMEFIPELIVPIVGFFTLESYVGNKGHII
MTISNALKKRDQKWTDMYGLIVSQWLSTVNTQFYTIKERMYNALNNQSQAIEKIIEDQY
NRYSEEDKMNINIDFNDIDFKLNQSINLAINNIDDFINQCSISYLMNRMIPLAVKKLKDFD
DNLKRDLLEYIDTNELYLLDEVNILKSKVNRHLKDSIPFDLSLYT*

FIGURE 18

A: First BoNTF(Hc) gene: SEQ ID NO: 33

GAATTCACGatgTCTTACACTAACGACAAAATCCTGATCCTGTACTTCAACAAACTGT
ACAAAAAAATCAAAGACAACTCTATCCTGGACATGCGTTACGAAAACAACAAATTC
ATCGACATCTCTGGCTATGGTTCTAACATCTCTATCAACGGTGACGTCTACATCTACT
CTACTAACCGCAACCAGTTCGGTATCTACTCTTCTAAACCGTCTGAAGTAAACATCG
CTCAGAACAACGACATCATCTACAACGGTCGTTACCAGAACTTCTCTATCTCTTTCTG
GGTTCGTATCCCGAAATACTTCAACAAAGTTAACCTGAACAACGAATACACTATCAT
CGACTGCATCCGTAACAACAACTCTGGTTGGAAAATCTCTCTGAACTACAACAAAAT
CATCTGGACTCTGCAGGACACTGCTGGTAACAACCAGAAACTGGTTTTCAACTACAC
TCAGATGATCTCTATCTCTGACTACATTAATAAATGGATCTTCGTTACTATCACTAAC
AACCGTCTGGGTAACTCTCGTATCTACATCAACGGTAACCTGATCGATGAAAAATCT
ATCTCTAACCTGGGTGACATCCACGTTTCTGACAACATCCTGTTCAAAATCGTTGGTT
GCAACGACACGCGTTACGTTGGTATCCGTTACTTCAAAGTTTTCGACACTGAACTGG
GTAAAACTGAAATCGAAACTCTGTACTCTGACGAACCGGACCCGTCTATCCTGAAAG
ACTTCTGGGGTAACTACCTGCTGTACAACAAACGTTACTACCTGCTGAACCTGCTCC
GGACTGACAAATCTATCACTCAGAACTCTAACTTCCTGAACATCAACCAGCAGCGTG
GTGTTTATCAGAAACCTAATATCTTCTCTAACACTCGTCTGTACACTGGTGTTGAAGT
TATCATCCGTAAAAACGGTTCTACTGACATCTCTAACACTGACAACTTCGTACGTAA
AAACGACCTGGCTTACATCAACGTTGTTGACCGTGACGTTGAATACCGTCTGTACGC
TGACATCTCTATCGCTAAACCGGAAAAAATCATCAAACTGATCCGTACTTCTAACTC
TAACAACTCTCTGGGTCAGATCATCGTTATGGACTCGATCGGTAACAACTGCACTAT
GAACTTCCAGAACAACAACGGTGGTAACATCGGTCTGCTGGGTTTCCACTCTAACAA
CCTGGTTGCTTCTTCATGGTACTACAACAACATCCGTAAAAACACTTCTTCTAACGGT
TGCTTCTGGTCTTTCATCTCTAAAGAACACGGTTGGCAGGAAAACtaaGAATTC B: BoNTF(Hc) #1 encoded protein: SEQ ID NO: 34

MSYTNDKILILYFNKLYKKIKDNSILDMRYENNKFIDISGYGSNISINGDVYIYSTNRNQF
GIYSSKPSEVNIAQNNDIIYNGRYQNFSISFWVRIPKYFNKVNLNNEYTIIDCIRNNNSGW
KISLNYNKIIWTLQDTAGNNQKLVFNYTQMISISDYINKWIFVTITNNRLGNSRIYINGNLI
DEKSISNLGDIHVSDNILFKIVGCNDTRYVGIRYFKVFDTELGKTEIETLYSDEPDPSILKD
FWGNYLLYNKRYYLLNLLRTDKSITQNSNFLNINQQRGVYQKPNIFSNTRLYTGVEVIIR
KNGSTDISNTDNFVRKNDLAYINVVDRDVEYRLYADISIAKPEKIIKLIRTSNSNNSLGQII
VMDSIGNNCTMNFQNNNGGNIGLLGFHSNNLVASSWYYNNIRKNTSSNGCFWSFISKE
HGWQEN*

FIGURE 19

A: Natural BoNTF(Hc) Gene

B: First BoNTF(Hc) Synthetic Gene

C: Second BoNTF(Hc) Synthetic Gene

RECOMBINANT VACCINE AGAINST BOTULINUM NEUROTOXIN

This application is a divisional application of and claims the benefit of U.S. application Ser. No. 09/910,186 filed Jul. 20, 2001 now U.S. Pat. No. 7,081,529, which is a continuation of U.S. application Ser. No. 09/611,419 filed Jul. 6, 2000 now U.S. Pat. No. 7,214,787, which is a continuation-in-part of U.S. patent application Ser. No. 08/123,975 filed Sep. 21, 1993 (abandoned) and a continuation of International Application No. PCT/US00/12890, which claims the benefit of U.S. Provisional Application Nos. 60/133,866, 60/133,868, 60/133,869, 60/133,865, 60/133,873, 60/133,867, all filed May 12, 1999, and U.S. Provisional Application No. 60/146,192, filed Jul. 29, 1999, all of which are incorporated herein in their entirety.

BACKGROUND OF THE INVENTION

1. Field of the Invention

This invention is directed to preparation and expression of synthetic genes encoding polypeptides containing protective epitopes of botulinum neurotoxin (BoNT). The invention is also directed to methods of vaccination against botulism using the expressed peptides.

2. Related Art

The sporulating, obligate anaerobic, gram-positive bacillus *Clostridium* produces eight forms of antigenically distinct exotoxins. Tetanus neurotoxin (TeNT) is produced by *Clostridium tetani* while *Clostridium botulinum* produces seven different neurotoxins which are differentiated serologically by specific neutralization. The botulinum neurotoxins (BoNT) have been designated as serotypes A, B, $C_1$, D, E, F, and G. Botulinum neurotoxins (BoNT) are the most toxic substances known and are the causative agents of the disease botulism. BoNT exert their action by inhibiting the release of the neurotransmitter acetylcholine at the neuromuscular junction (Habermann, E., et al., (1986), "Clostridial Neurotoxins: Handling and Action at the Cellular and Molecular Level," *Cur. Top. Microbiol. Immunol.*, 129:93-179; Schiavo, G., et al., (1992a), "Tetanus and Botulinum-B Neurotoxins Block Neurotransmitter Release by Proteolytic Cleavage of Synaptobrevin," *Nature*, 359:832-835; Simpson, L. L., (1986), "Molecular Pharmacology of Botulinum Toxin and Tetanus Toxin," *Annu. Rev. Pharmacol. Toxicol.*, 26:427-453) which leads to a state of flaccid paralysis. Indeed, only a few molecules of toxin can abolish the action of a nerve cell. Polyclonal antibodies derived for a specific neurotoxin can neutralize the toxic effects of that toxin but will not cross-neutralize another toxin serotype. Thus, to protect against all seven toxins, one needs seven vaccines.

Botulinum neurotoxins are translated as a single 150 kDa polypeptide chain and then posttranslationally nicked, forming a dichain consisting of a 100 kDa heavy chain and a 50 kDa light chain which remain linked by a disulfide bond (DasGupta, B. R., et al., (1972), "A Common Subunit Structure in *Clostridium botulinum* Type A, B, and E Toxins," *Biophys. Res. Commun.*, 48:108-112; DasGupta, B. R., (1989), "The Structure of Botulinum Neurotoxins," *Botulinum Neurotoxin and Tetanus Toxin*, (Simpson, L. L., Ed.), pp. 53-67, Academic Press, New York). Most of the clostridial strains contain specific endogenous proteases which activate the toxins at a protease-sensitive loop located approximately one third of the way into the molecule from the amino-terminal end. Upon reduction and fractionation (electrophoretically or chromatographically), the two chains can be separated; one chain has a Mr of ~100 kDa and is referred to as the heavy chain while the other has a Mr ~50 kDa and is termed the light chain.

The mechanism of nerve intoxication is accomplished through the interplay of three key events, each of which is performed by a separate portion of the neurotoxin protein. First, the carboxy half of the heavy chain (fragment C or $H_C$ is required for receptor specific binding to cholinergic nerve cells (Black, J. D., et al., (1986), "Interaction of $^{125}$I-botulinum Neurotoxins with Nerve Terminals. I. Ultrastructural Autoradiographic Localization and Quantitation of Distinct Membrane Acceptors for Types A and B on Motor Nerves," *J. Cell Biol.*, 103:521-534; Nishiki, T.-I., et al., (1994), "Identification of Protein Receptor for *Clostridium botulinum* Type B Neurotoxin in Rat Brain Synaptosomes," *J. Biol. Chem.*, 269:10498-10503; Shone, C. C., et al., (1985), "Inactivation of *Clostridium botulinum* Type A Neurotoxin by Trypsin and Purification of Two Tryptic Fragments. Proteolytic Action Near the COOH-terminus of the Heavy Subunit Destroys Toxin-Binding Activity, *Eur. J. Biochem.*, 151:75-82). There is evidence suggesting that polysialogangliosides (van Heyningen, W. E., (1968), "Tetanus," *Sci. Am.*, 218:69-77) could act as receptors for the toxins but the data supporting a specific receptor remains equivocal (Middlebrook, J. L., (1989), "Cell Surface Receptors for Protein Toxins," *Botulinum Neurotoxins and Tetanus Toxin*, (Simpson, L. L., Ed.) pp. 95-119, Academic Press, New York). After binding, the toxin is internalized into an endosome through receptor-mediated endocyctosis (Shone, C. C., et al., (1987), "A 50-kDa Fragment from the $NH_2$-terminus of the Heavy Subunit of *Clostridium botulinum* Type A Neurotoxin Forms Channels in Lipid Vesicles, *Euro. J. Biochem.*, 167:175-180) The amino terminal half of the heavy chain is believed to participate in the translocation mechanism of the light chain across the endosomal membrane (Simpson, 1986; Poulain, B., et al., (1991), "Heterologous Combinations of Heavy and Light Chains from Botulinum Neurotoxin A and Tetanus Toxin Inhibit Neurotransmitter Release in *Aplysia*," *J. Biol. Chem.*, 266:9580-9585; Montal, M. S., et al., (1992), "Identification of an Ion Channel-Forming Motif in the Primary Structure of Tetanus and Botulinum Neurotoxins," *FEBS*, 313:12-18). The low pH environment of the endosome may trigger a conformational change in the translocation domain, thus forming a channel for the light chain. The final event of intoxication involves enzymatic activity of the light chain, a zinc-dependent endoprotease (Schiavo, 1992a; Schiavo, G., et al., (1992b), "Tetanus Toxin is a Zinc Protein and its Inhibition of Neurotransmitter Release and Protease Activity Depend on Zinc," *EMBO J.*, 11:3577-3583), on key synaptic vesicle proteins (Schiavo, 1992a; Oguma, K., et al., (1995), "Structure and Function of *Clostridium botulinum* Toxins," *Microbiol. Immunol.*, 39:161-168; Schiavo, G., et al., (1993), "Identification of the Nerve Terminal Targets of Botulinum Neurotoxin Serotypes A, D, and E," *J. Biol. Chem.*, 268: 23784-23787; Shone, C. C., et al., (1993), "Proteolytic Cleavage of Synthetic Fragments of Vesicle-Associated Membrane Protein, Isoform-2 by Botulinum Type B Neurotoxin," *Eur. J. Biochem.*, 217:965-971) necessary for neurotransmitter release. The light chains of BoNT serotypes A, $C_1$, and E cleave SNAP-25 (synaptosomal-associated protein of M25, 000), serotypes B, D, F, and G cleave VAMP/synaptobrevin (synaptic vesicle-associated membrane protein); and serotype $C_1$ cleaves syntaxin. Inactivation of SNAP-25, VAMP, or syntaxin by BoNT leads to an inability of the nerve cells to release acetylcholine resulting in neuromuscular paralysis and possible death, if the condition remains untreated.

Human botulism poisoning is generally caused by type A, B, E or rarely, by type F toxin. Type A and B are highly poisonous proteins which resist digestion by the enzymes of the gastrointestinal tract. Foodborne botulism poisoning is caused by the toxins present in contaminated food, but wound and infant botulism are caused by in vivo growth in closed wounds and the gastrointestinal tract respectively. The toxins primarily act by inhibiting the neurotransmitter acetylcholine at the neuromuscular junction, causing paralysis. Another means for botulism poisoning to occur is the deliberate introduction of the toxin(s) into the environment as might occur in biological warfare. When the cause of botulism is produced by toxin rather than by in vivo infection the onset of neurologic symptoms is usually abrupt and occurs within 18 to 36 hours after ingestion. The most common immediate cause of death in respiratory failure due to diaphragmatic paralysis. Home canned foods are the most common sources of toxins. The most frequently implicated toxin is toxin A, which is responsible for more than 50% of morbidity resulting from botulinum toxin.

Because even small amounts of botulinal toxin can cause serious illness, persons such as laboratory workers who are exposed to toxin must learn to handle all samples that may contain toxin with extreme care. It is also suggested that such workers be protected from illness by vaccination against the toxins. Furthermore, persons exposed to conditions in which botulism toxins might be in the environment which might be inhaled or ingested, such as military personnel, need to be protected from the toxin.

Agents that abolish the action of BoNT have been investigated since the 1940s. Early work at Fort Detrick in the 1940s lead to the development of a toxoid vaccine to protect against serotypes A, B, $C_1$, D, and E toxins. The toxoid vaccine was manufactured by growing five *Clostridium botulinum* strains, extracting and precipitating the toxin from the growth media after cell lysis. Formalin was added to the crude preparation to inactivate the neurotoxin. Residual formalin was left in the vaccine product to ensure the toxin remains non-toxic. The product was adsorbed to aluminum hydroxide and blended. Currently, a pentavalent toxoid vaccine against serotypes A through E (Anderson, J. H., et al., (1981), "Clinical Evaluation of Botulinum Toxoids," *Biomedical Aspects of Botulism*, (Lewis, G. E., Ed.), pp. 233-246, Academic Press, New York; Ellis, R. J., (1982), "Immunobiologic Agents and Drugs Available from the Centers for Disease Control. Descriptions, Recommendations, Adverse Reactions and Serologic Response," 3rd ed., Centers for Disease Control. Atlanta, Ga.; Fiock, M. A., et al., (1963), "Studies of Immunities to Toxins of *Clostridium Botulinum*. IX. Immunologic Response of Man to Purified Pentavalent ABCDE Botulinum Toxoid," *J. Immunol.*, 90:697-702; Siegel, L. S., (1988), "Human Immune Response to Botulinum Pentavalent (ABCDE) Toxoid Determined by a Neutralization Test and by an Enzyme-Linked Immunosorbent Assay," *J. Clin. Microbiol.*, 26:2351-2356), available under Investigational New Drug (IND) status, is used to immunize specific populations of at-risk individuals, i.e., scientists and health care providers who handle BoNT and our armed forces who may be subjected to weaponized forms of the toxin. Though serotypes A, B, and E are most associated with botulism outbreaks in humans, type F has also been diagnosed (Midura, T. F., et al., (1972), "*Clostridium botulinum* Type F: Isolation from Venison Jerky," *Appl. Microbiol.*, 24:165-167; Green, J., et al., (1983), "Human Botulism (Type F)—A Rare Type," *Am. J. Med.*, 75:893-895; Sonnabend, W. F., et al., (1987), "Intestinal Toxicoinfection by *Clostridium botulinum* Type F in an Adult. Case Associated with Guillian-Barre Syndrome," *Lancet*, 1:357-361; Hatheway, C. L., (1976), "Toxoid of *Clostridium botulinum* Type F: Purification and Immunogenicity Studies," *Appl. Environ. Microbiol.*, 31:234-242). A separate monovalent toxoid vaccine against BoNTF is available under IND status. Hatheway demonstrated that the BoNTF toxoid could protect guinea pigs against a homologous challenge (Wadsworth, J. D. F., et al., (1990), "Botulinum Type F Neurotoxin," *Biochem. J.*, 268:123-128).

Even though toxoid vaccines are available, there are numerous shortcomings with their current use and ease of production. First, because *C. botulinum* is a spore-former, a dedicated facility is required to manufacture a toxin-based product. The requirement for a dedicated manufacturing facility is not trivial. It is extremely costly to renovate and upgrade an existing facility or to build a new one and then to maintain the facility in accordance with current Good Manufacturing Practices (cGMP) to manufacture one vaccine. Second, the yields of toxin production from *C. botulinum* are relatively low. Third, the toxoiding process involves handling large quantities of toxin and thus is dangerous, and the added safety precautions increase the cost of manufacturing. Fourth, the toxoid product for types A-E consists of a crude extract of clostridial proteins that may influence immunogenicity or reactivity of the vaccine, and the type F toxoid is only partially purified (IND 5077). Fifth, because the toxoiding process involves the use of formaldehyde, which inactivates the toxin, and residual levels of formaldehyde (not to exceed 0.02%) are part of the product formulation to prevent reactivation of the toxin, the vaccine is reactogenic. An additional component of the toxoid vaccines is the preservative thimerosal (0.01%), which also increases the reactogenicity of the product.

The development of a new-generation, recombinant vaccine could alleviate many of the problems associated with the toxoid. A recombinant vaccine would eliminate the need for a dedicated manufacturing facility. Presently, many cGMP facilities are in existence and available that could manufacture a recombinant product. There would be no need to culture large quantities of a hazardous toxin-producing bacterium. Production yields from a genetically engineered product is expected to be high. There would be no need to treat the vaccine with formalin because the product would be non-toxic from the outset. Recombinant products would be purer, less reactogenic, and more fully characterized. Thus, the cost of a recombinant product would be expected to be much lower than a toxoid because there would be no expenditures required to support a dedicated facility, and the higher production yields would reduce the cost of the vaccine product.

SUMMARY OF THE INVENTION

The instant invention provides immunogenic peptides capable of eliciting protective immunity against botulinum neurotoxin of serotypes A-G.

The instant invention also provides vaccines capable of eliciting protective immunity against botulinum neurotoxin, where the vaccines do not act as neurotoxins themselves.

The instant invention further provides methods for preparing non-toxic peptides for use in vaccines against botulinum neurotoxin by growing recombinant organisms which express the peptides.

The instant invention also provides methods for fast and efficient purification of the non-toxic peptides from cultures of recombinant organisms.

These and other aspects are illustrated by one or more of the following embodiments of the present invention.

In one embodiment, this invention provides a nucleic acid encoding the carboxy-terminal portion of the heavy chain ($H_C$) of botulinum neurotoxin (BoNT), the BoNT being selected from the group consisting of BoNT serotype A, BoNT serotype B, BoNT serotype C1, BoNT serotype D, BoNT serotype E, BoNT serotype F, and BoNT serotype G, wherein said nucleic acid is expressible in a recombinant organism selected from *Escherichia coli* and *Pichia pastoris*. Preferably, the nucleic acid comprises a nucleic acid sequence selected from SEQ ID No:1 (serotype A), SEQ ID No:7 (serotype B), SEQ ID No:9 (serotype C1), SEQ ID No:11 (serotype D), SEQ ID No:13 (serotype E), SEQ ID No:15 (serotype F), and SEQ ID No:17 (serotype G) In an alternative preferred embodiment, the nucleic acid encodes an HC amino acid sequence of BoNT selected from SEQ ID No:2 (serotype A), SEQ ID No:8 (serotype B), SEQ ID No:10 (serotype C1), SEQ ID No:12 (serotype D), SEQ ID No:14 (serotype E), SEQ ID No:16 (serotype F), and SEQ ID No:18 (serotype G).

In another embodiment, this invention provides a nucleic acid encoding the amino-terminal portion of the heavy chain ($H_N$) of botulinum neurotoxin (BoNT), the BoNT being selected from the group consisting of BoNT serotype B, BoNT serotype C1, BoNT serotype D, BoNT serotype E, BoNT serotype F, and BoNT serotype G, wherein said nucleic acid is expressible in a recombinant organism selected from *Escherichia coli* and *Pichia pastoris*. In a preferred embodiment, the nucleic acid comprises a nucleic acid sequence selected from SEQ ID No:21 (serotype B), SEQ ID No:23 (serotype C1), SEQ ID No:25 (serotype D), SEQ ID No:27 (serotype E), SEQ ID No:29 (serotype F), and SEQ ID No:31 (serotype G). Alternatively, the nucleic acid nucleic acid encodes an $H_N$ amino acid sequence of BoNT selected from SEQ ID No:22 (serotype B), SEQ ID No:24 (serotype C1), SEQ ID No:26 (serotype D), SEQ ID No:28 (serotype E), SEQ ID No:30 (serotype F), and SEQ ID No:32 (serotype G).

Preferably, the nucleic acid of this invention is a synthetic nucleic acid. In a preferred embodiment, the sequence of the nucleic acid is designed by selecting at least a portion of the codons encoding $H_C$ from codons preferred for expression in a host organism, which may be selected from gram negative bacteria, yeast, and mammalian cell lines; preferably, the host organism is *Escherichia coli* or *Pichia pastoris*. In another preferred embodiment, the nucleic acid sequence encoding $H_C$ is designed by selecting codons encoding $H_C$ which codons provide $H_C$ sequence enriched in guanosine and cytosine residues. More preferably, nucleic acid encoding $H_C$ or $H_N$ is expressed in a recombinant host organism with higher yield than a second nucleic acid fragment encoding the same $H_C$ sequence, said second nucleic acid fragment having the wild-type *Clostridium botulinum* sequence of $H_C$.

In yet another embodiment, this invention provides an expression vector comprising the nucleic acid of this invention, whereby $H_C$ and/or $H_N$ is expressed upon transfection of a host organism with the expression vector. Another embodiment of this invention provides a method of preparing a polypeptide comprising the carboxy-terminal portion of the heavy chain ($H_C$) of botulinum neurotoxin (BoNT) or the amino-terminal portion of the heavy chain ($H_N$) of botulinum neurotoxin (BoNT) selected from the group consisting of BoNT serotype A, BoNT serotype B, BoNT serotype C, BoNT serotype D, BoNT serotype E, BoNT serotype F, and BoNT serotype G, said method comprising culturing a recombinant host organism transfected with the expression vector of this invention under conditions wherein $H_C$ or $H_N$ is expressed. Preferably, the recombinant host organism is a eukaryote. In another preferred embodiment, the method of this invention further comprises recovering insoluble protein from the host organism, whereby a fraction enriched in $H_C$ or $H_N$ is obtained. Preferably, the host organism is *Pichia pastoris*.

In still another embodiment, this invention provides an immunogenic composition comprising the carboxy-terminal portion of the heavy chain ($H_C$) of botulinum neurotoxin (BoNT) selected from the group consisting of BoNT serotype A, BoNT serotype B, BoNT serotype C, BoNT serotype D, BoNT serotype E, BoNT serotype F, and BoNT serotype G. Preferably, the immunogenic composition is prepared by culturing a recombinant organism transfected with an expression vector encoding $H_C$. More preferably, the immunogenic composition is prepared by a method wherein an insoluble protein fraction enriched in $H_C$ is recovered from said recombinant organism.

In yet another embodiment, this invention provides an immunogenic composition comprising the amino-terminal portion of the heavy chain ($H_N$) of botulinum neurotoxin (BoNT) selected from the group consisting of BoNT serotype A, BoNT serotype B, BoNT serotype C, BoNT serotype D, BoNT serotype E, BoNT serotype F, and BoNT serotype G. Preferably, the immunogenic composition comprising $H_N$ is prepared by culturing a recombinant organism transfected with an expression vector encoding $H_N$. More preferably, the immunogenic composition is prepared from an insoluble protein fraction enriched in $H_N$ which is recovered from the recombinant organism.

In still another embodiment, this invention provides an immunogenic composition comprising a polypeptide comprising epitopes contained in the carboxy-terminal portion of the heavy chain ($H_C$) of botulinum neurotoxin (BoNT) and/or the amino-terminal portion of the heavy chain ($H_N$) of botulinum neurotoxin (BoNT) selected from the group consisting of BoNT serotype A, BoNT serotype B, BoNT serotype C, BoNT serotype D, BoNT serotype E, BoNT serotype F, and/or BoNT serotype G, said epitopes eliciting protective immunity toward the respective BoNT serotype. Preferably, the immunogenic composition elicits an ELISA response to the respective BoNT serotype(s) in an animal which is detectable in serum from the animal even when the serum is diluted 100-fold.

BRIEF DESCRIPTION OF THE DRAWINGS

FIGS. 1A and 1B respectively show the nucleotide sequence and the encoded amino acid sequence for a synthetic gene encoding the $H_C$ fragment of BoNT serotype A (SEQ ID NOs:1 and 2).

FIGS. 2A and 2B respectively show the nucleotide sequence and the encoded amino acid sequence for a synthetic gene encoding the $H_C$ fragment of BoNT serotype A (SEQ ID NOs: 3 and 4).

FIGS. 3A and 3B respectively show the nucleotide sequence and the encoded amino acid sequence for a synthetic gene encoding the $H_C$ fragment of BoNT serotype A (SEQ ID NOs:5 and 6).

FIGS. 4A and 4B respectively show the nucleotide sequence and the encoded amino acid sequence for a synthetic gene encoding the $H_C$ fragment of BoNT serotype B (SEQ ID NOs:7 and 8).

FIGS. 5A and 5B respectively show the nucleotide sequence and the encoded amino acid sequence for a synthetic gene encoding the $H_C$ fragment of BoNT serotype C (SEQ ID NOs:9 and 10).

FIGS. 6A and 6B respectively show the nucleotide sequence and the encoded amino acid sequence for a synthetic gene encoding the $H_C$ fragment of BoNT serotype D (SEQ ID NOs:11 and 12).

FIGS. 7A and 7B respectively show the nucleotide sequence and the encoded amino acid sequence for a synthetic gene encoding the $H_C$ fragment of BoNT serotype E (SEQ ID NOs:13 and 14).

FIG. 8 shows the nucleotide sequence for a synthetic gene encoding the $H_C$ fragment of BoNT serotype E and the encoded amino acid sequence (SEQ ID NOs:35 and 36).

FIGS. 9A and 9B respectively show the nucleotide sequence and the encoded amino acid sequence for a synthetic gene encoding the $H_C$ fragment of BoNT serotype F (SEQ ID NOs:15 and 16).

FIGS. 10A and 10B respectively show the nucleotide sequence and the encoded amino acid sequence for a synthetic gene encoding the $H_C$ fragment of BoNT serotype G (SEQ ID NOs:17 and 18).

FIGS. 11A and 11B respectively show the nucleotide sequence and the encoded amino acid sequence for a synthetic gene encoding the $H_N$ fragment of BoNT serotype A (SEQ ID NOs:19 and 20).

FIGS. 12A and 12B respectively show the nucleotide sequence and the encoded amino acid sequence for a synthetic gene encoding the $H_N$ fragment of BoNT serotype B (SEQ ID NOs:21 and 22).

FIGS. 13A and 13B respectively show the nucleotide sequence and the encoded amino acid sequence for a synthetic gene encoding the $H_N$ fragment of BoNT serotype C (SEQ ID NOs:23 and 24).

FIGS. 14A and 14B respectively show the nucleotide sequence and the encoded amino acid sequence for a synthetic gene encoding the $H_N$ fragment of BoNT serotype D (SEQ ID NOs:25 and 26).

FIGS. 15A and 15B respectively show the nucleotide sequence and the encoded amino acid sequence for a synthetic gene encoding the $H_N$ fragment of BoNT serotype E (SEQ ID NOs:27 and 28).

FIGS. 16A and 16B respectively show the nucleotide sequence and the encoded amino acid sequence for a synthetic gene encoding the $H_N$ fragment of BoNT serotype F (SEQ ID NOs:29 and 30).

FIGS. 17A and 17B respectively show the nucleotide sequence and the encoded amino acid sequence for a synthetic gene encoding the $H_N$ fragment of BoNT serotype G (SEQ ID NOs:31 and 32).

FIGS. 18A and 18B respectively show the nucleotide sequence and the encoded amino acid sequence for a synthetic gene encoding the $H_C$ fragment of BoNT serotype F (SEQ ID NOs:33 and 34).

FIGS. 19A, 19B, and 19C. FIG. 19A shows the AT base content of a putative fragment C region in native *C. botulinum* DNA. FIG. 19B shows the reduced AT content after the first design (rBoNTF(Hc)1) of the synthetic gene. FIG. 19C shows the AT content of the final gene design (rBoNTF(Hc)2) used to express recombinant rBoNTF(Hc) in *P. pastoris*.

FIG. 20A shows an SDS-PAGE gel and FIG. 20B shows a Western blot of samples at various steps along the rBoNTF(Hc) purification. Lanes from both figures are identical except lane 1, where SDS-PAGE shows Novex mark 12 wide-range molecular weight markers and Western blot shows Novex See Blue prestained molecular weight markers. Lane 2 is the cell lysate, lane 3 is the cell extract, lane 4 is the cell extract after dialysis, lane 5 is pool of rBoNTF(Hc) positive fractions after Mono S column chromatography, and lane 6 is pool of rBoNTF(Hc)-positive fractions after hydrophobic interaction chromatography.

FIG. 21A shows Mono S cation exchange chromatography of extract from *P. pastoris*. Proteins were eluted with increasing NaCl gradient. Fractions positive for rBoNTF(Hc) by Western analysis were pooled individually and subjected to hydrophobic interaction chromatography (the results of which are shown in FIG. 21B) and proteins were eluted with a decreasing ammonium sulfate gradient. In both panels, protein monitored by A280 nm is recorded on the left axis and elution conditions are recorded on the right axis, with the gradient trace laid over the chromatogram.

DETAILED DESCRIPTION OF THE EMBODIMENTS OF THIS INVENTION

Figure 20:
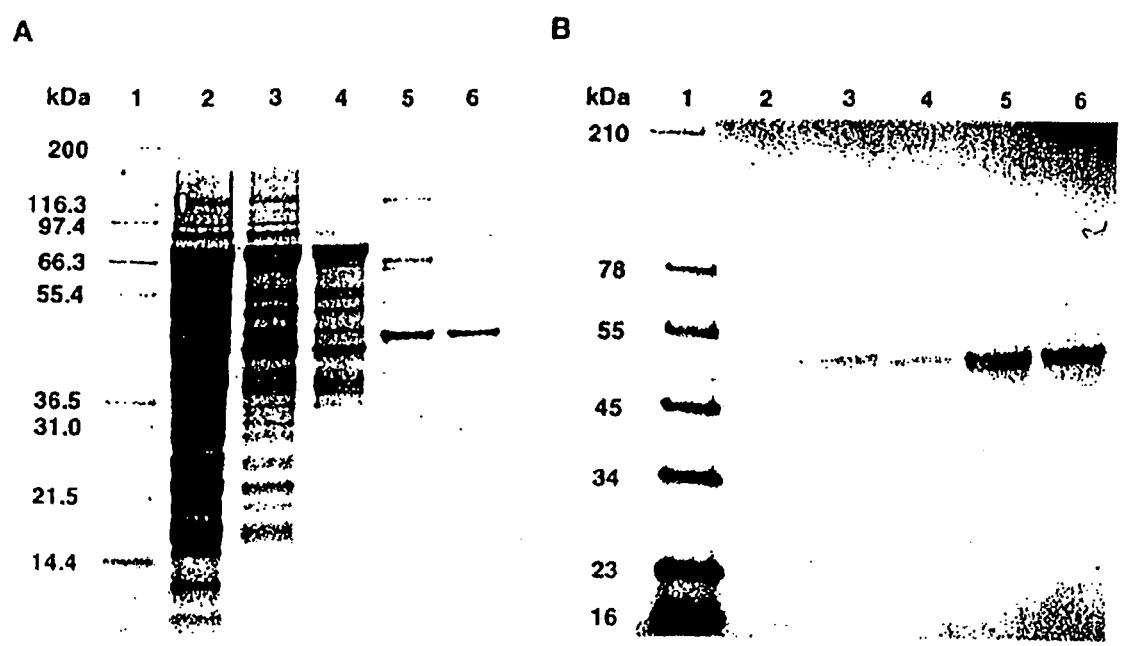
FIGS. 20A and 20B.

The present inventors have determined that animals, including primates, may be protected from the effects of botulinum neurotoxin (BoNT) by immunization with fragments of the botulinum neurotoxin protein expressed by recombinant organisms. Specifically, peptides comprising protective epitopes from the receptor binding domain and/or the translocation domain, found in the carboxy terminal and the amino terminal portions of the heavy chain of the BoNT protein, respectively, are expressed by recombinant organisms transfected with expression vectors encoding the peptides for each serotype of BoNT. Immunization with these recombinantly produced peptides will elicit antibodies capable of protecting animals against intoxication with the BoNT of the respective serotype.

This invention provides a genetically engineered vaccine for protection against botulism. The vaccine comprises fragments of the A and B toxins known as "C fragments" ($H_C$ domain). It is now possible to produce the $H_C$ fragments of the A and B toxins in *E. coli* using gene segment constructs of the $H_C$ fragment or an $H_C$ polypeptide fused to *E. coli* maltose binding protein. It has been found that the fusion product provides excellent protection against the native toxin challenge. The invention provides plasmids and recombinant proteins for use as vaccines to provide protection against toxins of *Clostridium botulinum*.

Kozaki et al. (in "Antibodies against Botulism Neurotoxin," L. L. Simpson, ed., 1989, Academic Press, New York) suggested that a protective epitope might be present in the 50 kDa carboxyl terminus (HC) region of the protein. Thompson et al. (1990, *Eur. J. Biochem.* 189:73-81 and Accession No. X52066, both of which are incorporated herein in their entirety by reference) deduced the amino acid sequence for the serotype A botulinum toxin. DasGupta et al. (1990, *Biochemie*, 72:661-664) identified the "nick" site for post-translational cleavage of the expressed toxin polypeptide, from which the sequence of the heavy chain can be deduced as SEQ ID NO:41 (amino acids 449 to 1296 of Accession No. X52066). See also Krieglstein, et al., 1994, *J. Protein Chem.*, 13:49-57.

Whelan et al. (*Appl. Environ. Microbiol.* 58:2345-2354, 1992 and Accession No. M81186, both of which are incorporated herein in their entirety by reference) have deduced the amino acid sequence for the serotype B botulinum toxin. Schmidt, et al. (1985, *Arch. Biochem. Biophys.*, 238:544-548) provided N-terminal sequence information for the heavy chain resulting from post-translational cleavage of the expressed toxin polypeptide, and the sequence of the heavy chain can be deduced from this information as SEQ ID NO:42 (amino acids 442 to 1291 of Accession No. M81186).

Analogous post-translational cleavage for all BoNT serotypes produces analogous heavy chain and light chain structures (see Krieglstein, et al., 1994, *J. Protein Chem.*, 13:49-57, and references cited therein).

Synthetic Gene Construction

Preliminary experiments indicated that the DNA sequence found in *C. botulinum* encoding the relevant BoNT fragments are not well expressed in typical recombinant hosts. Therefore, synthetic gene construction was undertaken, based on the amino acid sequence of the respective fragments.

Synthetic gene construction is a technique used to optimize for expression in heterologous host systems. The base composition (i.e., percent A+T or percent G+C) as well as the specific codons in a gene sequence play a role in determining whether a gene from one organism will be optimally expressed in a different organism. There is a reason why certain codons are used and why some are not. Organisms will use the codons in which corresponding tRNAs are present. If the organisms do not use certain codons, they most likely lack those specific tRNAs. As it turns out, codons found in clostridial DNA (i.e., genes found in the genus of bacterial called *Clostridium*) are very unique both in terms of base composition (i.e., very high A+T base composition) and in the use of codons not normally found in *E. coli* or yeast.

Table 1 is a chart depicting codon usage in *Pichia pastoris*. This table was generated by listing the codons found in a number of highly expressed genes in *P. pastoris*. The codon data was obtained by sequencing the genes and then listing which codons were found in the genes.

From Table 1, it is clear that the amino acid residues can be encoded for by multiple codons. When constructing synthetic genes using *P. pastoris* codon usage, it is preferred to use only those codons that are found in the naturally occurring genes in *P. pastoris*, and it should be attempted to keep them in the same ratio found in the genes of the natural organism. When the clostridial gene has an overall A+T richness of greater than 70% and A+T regions that have spikes of A+T of 95% or higher, they have to be lowered for expression in expression systems like yeast. (Preferably, the overall A+T richness is lowered below 60% and A+T in spikes is also lowered to 60% or below). It is of course necessary to balance keeping the same codon ratio (e.g., for glycine GGG was not found, GGA was found 22% of the time, GGT was found 74% of the time, GGC was found 3% of the time) with reducing the high A+T content. In the construction of the genes, it is preferred to keep the A+T spikes about 55%.

Considering codon usage for a number of organisms including *E. coli*, it turns out that a synthetic gene using *E. coli* codon usage also expresses fairly well in *P. pastoris*. Similarly, a synthetic gene using *P. pastoris* codon usage also appears to express very well in *E. coli*.

TABLE 1

CODON USAGE IN *PICHIA PASTORIS*

| Amino Acid | Codon | Number | Fraction |
|---|---|---|---|
| Gly | GGG | 0.00 | 0.00 |
| Gly | GGA | 59.00 | 0.22 |
| Gly | GGT | 197.00 | 0.74 |
| Gly | GGC | 9.00 | 0.03 |
| Glu | GAG | 112.00 | 0.58 |
| Glu | GAA | 80.00 | 0.42 |
| Asp | GAT | 56.00 | 0.32 |
| Asp | GAC | 118.00 | 0.88 |
| Val | GTG | 10.00 | 0.05 |
| Val | GTA | 8.00 | 0.04 |
| Val | GTT | 107.00 | 0.50 |
| Val | GTC | 87.00 | 0.41 |
| Ala | GCG | 1.00 | 0.00 |
| Ala | GCA | 25.00 | 0.10 |
| Ala | GCT | 147.00 | 0.80 |
| Ala | GCC | 71.00 | 0.29 |
| Arg | AGG | 2.00 | 0.01 |
| Arg | AGA | 111.00 | 0.79 |
| Ser | AGT | 8.00 | 0.04 |
| Ser | AGC | 3.00 | 0.02 |
| Lys | AAG | 145.00 | 0.79 |
| Lys | AAA | 38.00 | 0.21 |
| Asn | AAT | 18.00 | 0.13 |
| Asn | AAC | 119.00 | 0.87 |
| Met | ATG | 80.00 | 1.00 |
| Ile | ATA | 0.00 | 0.00 |
| Ile | ATT | 83.00 | 0.58 |
| Ile | ATC | 72.00 | 0.44 |
| Thr | ACG | 5.00 | 0.03 |
| Thr | ACA | 8.00 | 0.05 |
| Thr | ACT | 88.00 | 0.50 |
| Thr | ACC | 74.00 | 0.43 |
| Trp | TGG | 38.00 | 1.00 |
| End | TGA | 0.00 | 0.00 |
| Cys | TGT | 35.00 | 0.83 |
| Cys | TGC | 7.00 | 0.17 |
| End | TAG | 1.00 | 0.20 |
| End | TAA | 4.00 | 0.80 |
| Tyr | TAT | 18.00 | 0.12 |
| Tyr | TAC | 128.00 | 0.88 |
| Leu | TTG | 120.00 | 0.52 |
| Leu | TTA | 21.00 | 0.08 |
| Phe | TTT | 24.00 | 0.19 |
| Phe | TTC | 104.00 | 0.81 |
| Ser | TCG | 8.00 | 0.03 |
| Ser | TCA | 14.00 | 0.07 |
| Ser | TCT | 89.00 | 0.47 |
| Ser | TCC | 71.00 | 0.37 |
| Arg | CGG | 2.00 | 0.01 |
| Arg | CGA | 0.00 | 0.00 |
| Arg | CGT | 26.00 | 0.18 |
| Arg | CGC | 0.00 | 0.00 |
| Gln | CAG | 31.00 | 0.34 |
| Gln | CAA | 59.00 | 0.66 |
| His | CAT | 11.00 | 0.13 |
| His | CAC | 77.00 | 0.88 |
| Leu | CTG | 35.00 | 0.15 |
| Leu | CTA | 7.00 | 0.03 |
| Leu | CTT | 43.00 | 0.18 |
| Leu | CTC | 7.00 | 0.03 |
| Pro | CCG | 0.00 | 0.00 |
| Pro | CCA | 97.00 | 0.57 |
| Pro | CCT | 66.00 | 0.39 |
| Pro | CCC | 7.00 | 0.04 |

Synthetic genes for the $H_C$ fragments of botulinum neurotoxin serotypes A-G are shown in FIGS. 1-10, along with the amino acid sequences encoded by the synthetic genes. Synthetic genes for the $H_N$ fragments of botulinum neurotoxin serotypes A-G are shown in FIGS. 11-17, along with the amino acid sequences encoded by the synthetic genes. Synthetic genes having alternative gene sequences may be prepared by following the guidance provided herein concerning codon selection. The amino acid sequence encoded by such synthetic genes will preferably be the sequence of one of the BoNT serotype proteins, or a fragment thereof which contains protective epitopes. Suitable fragments include the $H_C$ fragments of BoNT serotypes A, B $C_1$, D, E, F, and G, and the $H_N$ fragments of BoNT serotypes A, B, $C_1$, D, E, F, and G. Such alternative gene sequences are within the contemplation of this invention.

Also within the contemplation of this invention are proteins containing protective epitopes from both the N-terminal and the C-terminal domains of the respective serotype BoNT proteins. Such proteins may be prepared by fusing a sequence encoding the translocation domain ($H_N$) to the sequence of the $H_C$ region. This may be accomplished by removing the restriction enzyme site of the 3' end of the translocation domain gene as well as the termination codon, and also removing the initiation codon, restriction enzyme site and any other nucleotides on the 5' end of the gene that are not part of the botulinum toxin gene. Then a common restriction enzyme site not found in either synthetic gene may be inserted on the 3' end of the $H_N$ gene and the 5' end of the $H_C$ gene, and this common restriction site may be used to fuse the two genes together.

Recombinant Peptide Production

The nontoxin fragment is very safe, will not require formalin treatment, and has been shown to produce significant immunity against the fully toxic parent molecule. There are two major advantages of the invention over the presently employed vaccine. First, the recombinantly-produced botulinum neurotoxin (rBoNT) protein fragments are completely nontoxic and, is thus, very safe. The fermentation of the host cell harboring the rBoNT gene (e.g., *Escherichia coli* or *Pichia pastoris*) will not require the high biological containment facilities presently needed to ferment the spore-forming *Clostridium botulinum* required for the production of the toxoid vaccine. Second, the synthetic gene can be placed in high expression systems and used to make much larger quantities of the fragment than toxin produced by the parent organism, *Clostridium botulinum*. Thus, there will be immense cost savings because it will be easier and safer to produce much larger quantities of the vaccine than is now possible.

Synthetic genes as described herein may be transfected into suitable host organisms to create recombinant production organisms, and cultures of these recombinant organisms can then be used to produce immunogenic peptide fragments capable of conferring protective immunity against BoNT of the respective serotypes. Exemplary techniques for transfection and production of BoNT fragments are shown in the Examples. Alternative techniques are well documented in the literature (See, e.g., Maniatis, Fritsch & Sambrook, "Molecular Cloning: A Laboratory Manual" (1982); "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984), and Sambrook, et al., "Molecular Cloning: a Laboratory Manual" (1989)). Such techniques are explained fully in the literature, and modification of these techniques within the scope of this invention is within the skill in the art.

The synthetic gene for BoNT serotype B fragment $H_C$ (see FIG. 4A) has been inserted into the yeast expression vector pHIL-D4, and integrated into the chromosome of *Pichia pastoris* strain GS115. The expressed product (see amino acid sequence in FIG. 4B) had the expected molecular weight as shown by denaturing polyacrylamide gel electrophoresis (PAGE) and Western blot analysis using antibodies directed against botulinum neurotoxin serotype B. The expressed recombinant BoNTB ($H_C$) elicited high antibody titers as judged by the Enzyme Linked Immunosorbent Assay (ELISA) and, more importantly, these circulating serum titers protected mice, guinea pigs, and non-human primates from challenges with active toxin. Industrial scale manufacturing processes (fermentation and purification) have been completed and a pilot lot has been produced in compliance with cGMP.

The synthetic gene for BoNT serotype C fragment $H_C$ (see FIG. 5A) has been inserted into the yeast expression vector pHIL-D4, and integrated into the chromosome of *Pichia pastoris* strain GS115. The expressed product (see amino acid sequence in FIG. 5B) had the expected molecular weight as shown by denaturing polyacrylamide gel electrophoresis (PAGE) and Western blot analysis using antibodies directed against botulinum neurotoxin serotype C. The expressed recombinant BoNTC ($H_C$) elicited high antibody titers as judged by the Enzyme Linked Immunosorbent Assay (ELISA) and, more importantly, these circulating serum titers protected mice from challenges with active toxin.

The synthetic gene for BoNT serotype D fragment $H_C$ (see FIG. 6A) has been inserted into the yeast expression vector pHIL-D4, and integrated into the chromosome of *Pichia pastoris* strain GS115. The expressed product (see amino acid sequence in FIG. 6B) had the expected molecular weight as shown by denaturing polyacrylamide gel electrophoresis (PAGE) and Western blot analysis using antibodies directed against botulinum neurotoxin serotype D. The expressed recombinant BoNTD ($H_C$) elicited high antibody titers as judged by the Enzyme Linked Immunosorbent Assay (ELISA) and, more importantly, these circulating serum titers protected mice from challenges with active toxin.

The synthetic gene for BoNT serotype E fragment $H_C$ (see FIG. 7A) has been inserted into the yeast expression vectors pHILD2, pHILD3, and pPIC9K (see FIG. 7B). A modified form of the synthetic gene in which an internal EcoRI site was removed and the gene was enlarged (see FIG. 8) was inserted into the yeast vector pHIL-D4, and integrated into the chromosome of *Pichia pastoris* strain GS115. The expressed product (see amino acid sequence in FIG. 8) had the expected molecular weight as shown by denaturing polyacrylamide gel electrophoresis (PAGE) and Western blot analysis using antibodies directed against botulinum neurotoxin serotype E. The expressed recombinant BoNTE ($H_C$) elicited high antibody titers as judged by the Enzyme Linked Immunosorbent Assay (ELISA) and, more importantly, these circulating serum titers protected mice from challenges with active toxin.

The synthetic gene for BoNT serotype F fragment $H_C$ (see FIG. 9A) has been inserted into the yeast expression vector pHIL-D4, and integrated into the chromosome of *Pichia pastoris* strain GS115. The initial step in the development of the rBoNTF($H_C$) vaccine candidate was to design a gene which could satisfactorily be expressed in a *pichia* host. A synthetic gene encoding rBoNTF($H_C$) was constructed to lower the inherent AT richness of the native clostridial gene and to remove any potentially rare codons. Clostridial genes having an AT content in excess of 65% or having an average AT content but containing AT-rich tracts usually contain multiple terminators/polyadenylation signals, which can result in premature termination of transcripts when expression is attempted in yeast (Romanos, M. A., et al., (1995), "Expression of Cloned Genes in Yeast," *DNA Cloning 2: Expression Systems*," (Glover D., et al., Eds.), Oxford Univ. Press, London). The synthetic gene in this study required two successive rounds of alterations before the yeast could properly produce full-length antigen. The expressed product (see amino acid sequence in FIG. 9B) had the expected molecular weight as shown by denaturing polyacrylamide gel electrophoresis (PAGE) and Western blot analysis using antibodies directed against botulinum neurotoxin serotype F.

A previous study (Hatheway, 1976) demonstrated that the serotype F toxoid antigen needed to be at least partially purified to be efficacious. The same observation was noted with the rBoNTF($H_C$) antigen produced in *pichia* cells as the crude cell lysate did not protect mice against a BoNTF challenge. The putative receptor-binding domain of BoNTF was purified from yeast and shown to be efficacious in a mouse model. The expressed recombinant BoNTF ($H_C$) elicited high antibody titers as judged by the Enzyme Linked Immunosorbent Assay (ELISA) and, more importantly, these circulating serum titers protected mice from challenges with active toxin.

The synthetic gene for BoNT serotype G fragment $H_C$ (see FIG. 10A) has been inserted into the yeast expression vector pHIL-D4, and integrated into the chromosome of *Pichia pastoris* strain GS115. The expressed product (see amino acid sequence in FIG. 10B) had the expected molecular weight as shown by denaturing polyacrylamide gel electrophoresis (PAGE) and Western blot analysis using antibodies directed against botulinum neurotoxin serotype G. The expressed recombinant BoNTG ($H_C$) elicited high antibody titers as judged by the Enzyme Linked Immunosorbent Assay (ELISA) and, more importantly, these circulating serum titers protected mice from challenges with active toxin.

When purifying a protein for the first time, it is important to generate a viable means for identifying which fractions contain product. If the protein of interest is not an enzyme or does not absorb at a unique wavelength, there are still suitable assays (for example mass spectrometry) for identifying the product. The inventors chose to monitor the purification of rBoNT($H_C$) through immunological detection by Western blot analysis. However, with various polyclonal antibodies against whole toxin available but without an appropriate positive control, the Western blot results can only be interpreted as ambiguous until a purified sample is sequenced or shown to be protective.

There are two major issues of concern when extracting C-fragment, $H_N$, and/or heavy chain ($H_C$) antigens from *pichia* cells. The first concern is the solubility of these proteins (i.e., can enough product be extracted into the soluble fraction for further processing?). The second concern deals with the effective removal of polynucleic acids and/or other contaminating materials, which strongly interfere with the necessary chromatography.

The zwitterionic detergent, CHAPS, is most notably an effective agent for solubilizing membrane proteins. Membrane proteins exist in a hydrophobic environment, and if removed from that environment, possess strong tendencies to aggregate and ultimately precipitate. CHAPS prevents that aggregation from occurring with membrane bound proteins. The inventors extrapolated this premise to the clostridial proteins noted above. C-fragments, translocation domains ($H_N$), and entire heavy chains are missing their natural partner (the remaining segments of the neurotoxin) and thus, presumably bare exposed hydrophobic regions on their protein surface where the $H_C$, $H_N$, or heavy chain normally associates with rest of the neurotoxin. These exposed hydrophobic regions are potential nucleation sources for protein aggregation, because the natural tendency of a protein in an aqueous environment is to bury their hydrophobic surface. When *pichia* cells are disrupted with CHAPS (on the order of 0.3% W/V) present in the cracking buffer, the amount of fragment C protein isolated in the soluble fraction has been observed to increase from less than 5% to nearly 80% with serotype $C_1$. Dramatic increases in solubility have been noted with C-fragment serotypes A and F as well.

Once a soluble antigen has been produced, the subsequent task is to separate that antigen from the myriad of *pichia* host proteins, lipids, and other impurities that exist in the extracted medium. In order for the chemical separations to be feasible by liquid chromatography, it is critical that polynucleic acids be efficiently removed. Nucleotides will either bind to the C-fragment (serotypes A, E, and F due to their elevated pIs) or will bind to the anion-exchange chromatography resin (as is used in the first purification step of the $C_1$ process). With either case, the chromatography is rendered futile. The C-fragment product will either fail to bind to the chromatography media or it will elute over an unacceptably large sodium chloride concentration range. *Pichia* cells possess an abundant amount of DNA. Polyethyleneimine (PEI) is a polycationic agent that readily precipitates nucleotides. When *pichia* cell extracts are treated with PEI, the nucleic acids are efficiently precipitated and removed by centrifugation without significant loss of product. More importantly, the chromatographic separation of C-fragments from *pichia* proteins are dramatically improved.

The soluble portion of the cell lysate may typically be purified in two conventional chromatographic steps. The ultimate objective of this work is to obtain FDA licensure of rBoNT as a safe and effective vaccine. Even though separations can be accomplished at extremely high resolution with affinity chemistry, there remains an undesirable effect of hapten leaching from the resin. Thus, a preferred separation employs a cation-exchange step followed by hydrophobic interaction chromatography (HIC). These two steps complement each other as they provide separations based on electrostatic and hydrophobic interactions. The cation-exchange step was particularly efficient in increasing the purity of rBoNTF($H_C$), as the antigen was estimated to be purified greater than 52-fold. The efficiency of purification is primarily attributed to the significant difference in isoelectric points between most *pichia* proteins (pIs<7) and rBoNT($H_C$) (experimental pI=9.4 for rBoNTF($H_C$), data not shown) and thus, the *pichia* proteins were removed in the column flow through. Precipitate that results when the cation-exchange pool is treated with ammonium sulfate contains mostly *pichia* proteins and very little rBoNT product. The HIC step removes most or all of the remaining impurities. The yield of soluble rBoNTF($H_C$) from the total recombinant yeast cell lysate was estimated to be greater than 28% with a purity greater than 98%. Use of similar purification steps for rBoNTA($H_C$) produced greater than 95% pure material.

A significant amount of rBoNTF($H_C$) product (30-40%) was identified in the insoluble portion of the cell lysate. Also, the antigen was 35% of the total protein present in the pellet; in effect it was more pure than the soluble rBoNTF($H_C$) was after the ion-exchange step. This suggests an alternative process whereby insoluble rBoNT product produced in yeast may be resolubilized and purified to homogeneity. The resolubilization may be performed by resuspending the pellet in urea and subsequently removing the urea by dialyses in nondenaturing buffer. A single chromatographic step using cation-exchange chemistry may be sufficient to purify the resolubilized antigen, in some cases to greater than 98%. The yield of resolubilized rBoNTF($H_C$) product from the total cell lysate was estimated to be >19%. The overall bench scale yield of purified soluble and resolubilized rBoNTF($H_C$) was estimated to be greater than 47% or 240 mg/Kg of the cell paste. A similar procedure would be suitable for purification of rBoNTA($H_C$) and other rBoNT fragment peptides from yeast.

Analysis of CD spectra of both soluble and resolubilized product revealed the presence of significant β-sheet which is in agreement with that predicted for rBoNTF($H_C$) using an artificial neural network (Lebeda, F. J., et al., (1997), "Predicting Differential Antigen-Antibody Contact Regions Based on Solvent Accessibility," *J. Protein Chem.*, 16:607-618), and that determined by crystal structure of BoNT serotype A (Lacy, D. B., et al., (1998), "Crystal Structure of Botulinum Neurotoxin Type A and Implications for Toxicity," *Nat. Struct. Biol.*, 5:898-902). However, even though CD revealed that the two antigens possessed similar folds, there were subtle differences between the two spectra suggesting that the secondary structures, and hence, tertiary structures were not identical.

Immunization

The purified soluble and resolubilized antigens appear to be in a folded conformation. However, the bottom line with any potential vaccine is the demonstration of protection. Are the antigens in a conformation that will elicit the production of neutralizing antibody? To answer this question, mice were inoculated with rBoNTF($H_C$) and subsequently challenged with a high level of rBoNTF toxin. The purified soluble rBoNTF($H_C$) completely protected mice receiving three inoculations of 0.2 μg from challenge with 1000 mouse i.p. $LD_{50}$ of BoNT/F toxin. Analysis of the association of dose with survival indicated that dose was associated with the odds of surviving (odds ratio=2.0, meaning that the odds of survival increase twofold per unit increase in dose with a 95% confidence level from 1.3 to 3.1). The number of inoculations was also associated with survival. Both two inoculations and three inoculations were associated with increased odds of survival relative to a single inoculation (5.3-fold with a 95% confidence level of 1.2-23 for two inoculations and 22-fold with a 95% confidence level of 4.3-110 for three inoculations). It is apparent that a single shot at higher doses achieved protection comparable to multiple inoculations at lower doses. Also, three doses of 1 μg of purified resolubilized rBoNTF($H_C$) completely protected mice from a challenge of 5000 mouse i.p. $LD_{50}$ of BoNTF toxin, thus demonstrating that refolded rBoNTF($H_C$) from the insoluble fraction of lysate could also be a prosperous source of antigen.

Individual antibody ELISA titer appears to be an excellent predictor of mouse survival. If the antibody titer of a mouse was 100 or greater, that mouse was predicted to and did survive a challenge of 1000 mouse i.p. $LD_{50}$ of BoNTF toxin. Upon vaccination of mice with 2 or 3 doses of rBoNTA($H_C$) or rBoNTB($H_C$) vaccine delivered on a specific schedule (i.e., parental intramuscular injection at 0, 4, and 8 weeks), survival of animals challenged with 100,000 or 1,000,000 million LD50 of toxin is very high. Measurement of the antibody levels in these animals via an ELISA shows that the survival rate can be correlated with the measured antibody level. The ELISA is performed by coating a microtiter plate with toxin or fragment C itself, then sera from the vaccinated mice is added at various dilutions (i.e., sera diluted 1/100, 1/400, 1/1600, 1/6400, etc.). Since fragment C is sufficient to elicit protection in animals, preferably assays for neutralizing antibody titer in sera from animals vaccinated with fragment C are performed using microtiter plates coated with fragment C. Antibody in the sera will bind to the toxin or the fragment C, and the bound antibody may be detected by a secondary antibody (e.g., anti-mouse IgG) that is coupled to horseradish peroxidase or alkaline phosphatase. The secondary IgG will bind to the anti-BoNT antibody that was raised to the fragment C vaccine. After washing the microtiter wells, a substrate for the peroxidase or phosphatase enzymes is added to the wells. The substrate will give off a color once the enzyme has cleaved the substrate, and the intensity of the color measured (e.g., at 405 nm. Typically, a reading of 0.2 is used as the base. Thus, if dilution of the sera by 1/1600 gives a reading of 0.15 at 405 nm and a dilution of 1/400 gives a reading of 0.45 at 405 nm, the antibody titer in the sera in characterized as 1/400 dilution (i.e., titer of 400 fold). Obviously, if readings of 0.2 are obtained at higher dilutions, better protection is observed. With rBoNTA($H_C$) vaccination, for mice which had ELISA titers of less than 100, only 14.3% survival rate was observed under the conditions of vaccination and challenge. With rBoNTF(Hc), for mice which had ELISA titers of 100 fold, under the condition of vaccination and challenge, 100% of the mice were protected.

It also will be well known to one of ordinary skill in the art that a susceptible host may be immunized using the appropriate peptide vaccine formulated in adjuvant to increase the immune response. Such adjuvants include but are not limited to Freund's (complete and incomplete), mineral gels, such as aluminum hydroxide, surface active substances such as keyhole limpet hemocyanin, lysolecithin, pluronic polyols, polyanions, peptides, BCG (Bacille Calmette-Guerin), oil emulsions and dinotrophenols. Immunization can be carried out with additional various presentation and cross-linking permutations. By way of example and not of limitation, such permutations include rBoNT peptides cross-linked to KLH as a carrier, any rBoNT peptide cross-linked to any other rBoNT protein as carrier, rBoNT peptides cross-linked to themselves, and these combinations presented by the various adjuvants listed above. It will become evident that such permutations are available in regard to other peptides and self-assembled peptides disclosed throughout this specification.

It will also be known to one of ordinary skill in the art that use of the term "susceptible host" includes any such mammalian host susceptible to intoxication by BoNT. It will be further evident that any such susceptible host is a candidate for treatment to promote protection from BoNT utilizing the peptide vaccines and associated methods described in this specification.

EXAMPLES

In order to facilitate a more complete understanding of the invention, a number of Examples are provided below. However, the scope of the invention is not limited to specific embodiments disclosed in these Examples, which are for purposes of illustration only.

Example 1

Synthesis and Cloning of a Synthetic Gene Encoding rBoNTF($H_C$)

A synthetic gene encoding a putative fragment C region of botulinum neurotoxin serotype F was designed and constructed for expression in *Escherichia coli* (Holley et al., submitted to Vaccine). The recombinant BoNTF($H_C$)$_1$ gene was expressed in *E. coli* as a fusion protein with maltose-binding protein (MBP) with yields of 1 mg/L culture (See FIG. 18).

The same gene was used for expression studies in the yeast, *P. pastoris*. This particular host was chosen because it could produce high levels of recombinant proteins (Cregg, J. M., et al., (1993), "Recent Advances in the Expression of Foreign Genes in *Pichia pastoris*," *Bio/Technology*, 11:905-909; Romanos, M. A., et al., (1992), "Foreign Gene Expression in Yeast: A Review," *Yeast*, 8:423-488; Sreekrishna, K., et al., (1988), "High Level Expression of Heterologous Proteins in Methylotrophic Yeast *Pichia pastoris,*" *J. Bas. Microbiol.,* 28:265-278) and because it lacked endotoxins which would facilitate product development. Intracellular expression of the antigen was used to avoid potential glycosylation of the recombinant protein. The rBoNTF($H_C$)$_1$ gene was modified at its 3' end for insertion into the unique EcoR I site of the yeast vector, pHIL D4. The recombinant construct containing the rBoNTF($H_C$)$_1$ gene was subsequently linearized with SacI and the cassette integrated into the chromosomal alcohol oxidase (AOX 1) of *Pichia pastoris* strain GS115 (Clare, J. J., et al., (1991), "High-Level Expression of Tetanus Toxin Fragment C in *Pichia pastoris* Strains Containing Multiple Tandem Integrations of the Gene," *Bio/Technology,* 9:455-460). Yeast transformants expressing the selectable markers histidine dehydrogenase (Cregg, J. M., et al., (1985), "*Pichia pastoris* as a Host System for Transformations," *Mol. Cell. Biol.,* 5:3376-3385) and aminoglycoside phosphotransferase 3' (I) (Scorer, C. A., et al., (1994), "Rapid Selection Using G418 of High Copy Number Transformants of *Pichia pastoris* for High-Level Foreign Gene Expression," *Bio/Technology,* 12:181-184) were isolated. These isolates were further characterized for their ability to express rBoNTF($H_C$) after induction with methanol. Although the various transformants generated were able to express the selectable markers, no expression of rBoNTF($H_C$,) as judged by SDS/PAGE and blot analysis was observed in these isolates (data not shown).

SDS/PAGE, Western Blot, and Protein Assays

Total protein concentrations were determined by using the Pierce BCA™ (bicinchoninic acid) protein assay kit with BSA as a standard. The purity of the rBoNTF($H_C$) product was assessed by SDS/PAGE with Novex (San Diego, Calif., U.S.A.) gel electrophoresis supplies, reagents, protocols, and National Institutes of Health (NIH) imaging software as previously described (Byrne, M. P., et al., (1998), "Purification, Potency, and Efficacy of the Botulinum Neurotoxin Type A Binding Domain from *Pichia pastoris* as a Recombinant Vaccine Candidate," *Infect. Immun.,* 66:4817-4822). Western blot assays were used to identify FPLC fractions containing rBoNTF($H_C$) as previously described (Byrne, 1998) with the following changes. The primary antibody used was a polyclonal protein G sepharose-purified horse anti-BoNTF antibody incubated at 1 µg/ml for 3 h. The secondary antibody used was a horseradish peroxidase-labeled affinity-purified goat anti-horse IgG (Kirkegaard & Perry Laboratories, Gaithersburg, Md., U.S.A.) assayed at 1 µg/ml for 2 h.

Example 2

Synthesis and Cloning of a Synthetic Gene Encoding rBoNTF($H_C$)

A second synthetic gene, rBoNTF($H_C$)$_2$, was subsequently designed to facilitate expression in *P. pastoris*. Redesigning the gene was intended to lower specific regions of the rBoNTF($H_C$)$_1$ gene in which spikes of AT-rich tracts still remained. Previous work had shown that rare codons (Makoff, A. J., et al., (1989), "Expression of Tetanus Toxin Fragment C in *E. coli*: High Level Expression by Removing Rare Condons," *Nucleic Acids Res.,* 17:10191-10201) and/or highly enriched AT base compositions (Romanos, M. A., et al., (1991), "Expression of Tetanus Toxin Fragment C in Yeast: Gene Synthesis is Required to Eliminate Fortuitous Polyadenylation Sites in AT-rich DNA," *Nucleic Acids Res.,* 19:1461-1467) in clostridial DNA were incompatible with optimum expression of clostridial genes in *E. coli* and yeast. A second synthetic gene encoding the rBoNTF($H_C$) fragment was designed and constructed using *P. pastoris* codon usage (Sreekrishna, K., (1993), "Strategies for Optimizing Protein Expression and Secretion in the Methylotrophic Yeast *Pichia pastoris,*" *Industrial Micororganisms: Basic and Applied Molecular Genetics,* (Baltz, R. H., et al, Eds.), pp. 119-126, Am. Soc. Microbiol., Washington, D.C.) Briefly, complimentary oligonucleotides encoding the amino terminal region of the F($H_C$)(423 nucleotides flanked with EcoRI and PstI sites), the central region of the F($H_C$) (606 nucleotides flanked by PstI and SalI sites) and the carboxy-terminal region of F($H_C$) (336 nucleotides flanked by SalI and EcoRI sites) were annealed and cloned into pUC or PCR zero-blunt plasmid vectors. The AT base composition in the native clostridial F($H_C$) DNA averaged 76% while rBoNTF($H_C$)$_1$ averaged 58% and rBoNTF($H_C$)$_2$, 53% (FIG. 19) The synthetic gene sequence of rBoNTF($H_C$)$_2$ and the 432 amino acids it encoded for is shown in FIG. 9. After nucleotide sequencing, the cloned fragments were excised by the appropriate restriction endonucleases, separated by agarose gel electrophoresis, and purified. The isolated DNA fragments were ligated simultaneously into EcoR I digested and dephosphorylated plasmid pHIL D4. The vector harboring the rBoNTF($H_C$)$_2$ gene was integrated into the chromosomal AOX1 locus of *P. pastoris* as described above. Transformants expressing selectable markers (histidine dehydrogenase and aminoglycoside phosphotransferase 3' (I)) were isolated and tested for their ability to express rBoNTF($H_C$). Unlike the rBoNTF($H_C$)$_1$ gene, rBoNTF($H_C$)$_2$ was expressed after induction with methanol and yielded the expected molecular weight of approximately 50,000 daltons as judged by SDS/PAGE and Western blot analysis (FIG. 20). The deduced molecular mass of the encoded polypeptide was 50,250 daltons.

Example 3

Expression and Cell Disruption of rBoNTF($H_C$) in *P. pastoris*

Large-scale fermentation conditions and optimal intracellular expression of rBoNTF($H_C$) were determined for the yeast strain *P. pastoris*.

Protein Expression

A stock seed culture of *P. pastoris* was grown in shake-flasks containing 0.5 L of YNB medium (13.4 g/L yeast nitrogen base without amino acids, 20 g/L glycerol, 0.4 mg/L biotin, in 100 mM sodium phosphate, pH 6.0). Cultures were grown at 30° C. until an $A_{600}$ of 20 absorbance units was achieved, and then used to inoculate a 5-L BioFlo 3000 fermentor (New Brunswick Scientific, Edison, N.J., U.S.A.) containing 2.5 L basal-salt medium plus $PTM_4$ trace mineral salts and 4% glycerol. Dissolved oxygen was maintained at 40% and the pH was maintained at 5.0 with 30% ammonium hydroxide. After the initial glycerol was consumed, 50% (w/v) glycerol was added at a rate of 20 g/L/h for 1 h then decreased linearly to 0 g/L/h over 3 h. The medium was enriched with 1.5 g methanol/L of medium. Methanol feed was started at 4 g/L/h and linearly increased to 9 g/L/h over 10 h. The methanol feed rate was adjusted by using the dissolved oxygen-spike method (Chiruvolu, V., et al., (1997), "Recombinant Protein Expression in an Alcohol Oxidase-Defective Strain of *Pichia pastoris* in Feed-Batch Fermentations, *Enzyme Microbiol. Technol.,* 21:277-283). After 10 h of methanol induction, the cells were harvested by centrifugation at 6000 g for 10 min at 4° C. with a Beckman JA-10 rotor (Beckman Instruments, Palo Alto, Calif., U.S.A.) and then stored at −20° C.

Protein Expression

A stock seed culture of *P. pastoris* was grown in shake-flasks containing 0.5 L of YNB medium (13.4 g/L yeast nitrogen base without amino acids, 20 g/L glycerol, 0.4 mg/L biotin, in 100 mM sodium phosphate, pH 6.0). Cultures were grown at 30° C. until an $A_{600}$ of 20 absorbance units was achieved, and then used to inoculate a 5-L BioFlo 3000 fermentor (New Brunswick Scientific, Edison, N.J., U.S.A.) containing 2.5 L basal-salt medium plus $PTM_4$ trace mineral salts and 4% glycerol. Dissolved oxygen was maintained at 40% and the pH was maintained at 5.0 with 30% ammonium hydroxide. After the initial glycerol was consumed, 50% (w/v) glycerol was added at a rate of 20 g/L/h for 1 h then decreased linearly to 0 g/L/h over 3 h. The medium was enriched with 1.5 g methanol/L of medium. Methanol feed was started at 4 g/L/h and linearly increased to 9 g/L/h over 10 h. The methanol feed rate was adjusted by using the dissolved oxygen-spike method (Chiruvolu, 1997). After 10 h of methanol induction, the cells were harvested by centrifugation at 6000×g for 10 min at 4° C. with a Beckman JA-10 rotor (Beckman Instruments, Palo Alto, Calif., U.S.A.) and then stored at −20° C.

Cell Disruption and Sample Preparation

Eleven grams of frozen cell paste was resuspended in 100 ml of 50 mM $Na_2HPO_4$/2 mM $Na_2EDTA$/1 mM PMSF, pH 6.8 at 4° C. The suspended cells were disrupted by three successive passes through a microfluidizer device (model 110Y, Microfluidics Corp., Newton, Mass., U.S.A.) at 21000 psi. The temperature of the disruptate was kept below 10° C. throughout the process by cooling the exit line and collection flask with ice. The cells were judged to be greater than 95% disrupted as determined by microscopy. In comparison, 8-10 passes through a Gaulin homogenizer were required to efficiently disrupt the cells in past protocols. SDS-PAGE and Western blot analysis of cell lysate showed that expressed rBoNTF(HC) represented <0.5% of the total protein. The resulting cell lysate volume was 105 ml with a protein concentration of 11 mg/ml. Cellular debris and insoluble proteins were removed by centrifugation at 15000 g for 15 min at 4° C. with a Sorval SS-34 rotor (Sorval Instruments, Newtown, Conn., U.S.A.). The resulting extract was noticeably turbid due to the presence of lipids and significant quantities of nucleic acids. As rBoNTF(HC) possessed a calculated isoelectric point of 9.1 and presumably interacted strongly with DNA, DNase was added to the cell extract in order to digest the polynucleotides and facilitate purification. To remove the polynucleotides, the extract was treated with DNase (100 units/ml, Aldrich) and $ZnCl_2$ (2 mM, Aldrich) at room temperature for 30 min and then dialyzed extensively with 10 kDa molecular weight cut off (MWCO) Slide-A-Lyzer dialysis cassettes (Pierce) in 50 mM $Na_2HPO_4$/2 mM $Na_2EDTA$/1 mM PMSF, pH 6.8 at 4° C. A precipitate developed during dialysis that was separated by centrifugation at 15000 g for 15 min at 4° C. with a Sorval SS-34 rotor. The clarified extract contained 7.8 mg/ml of total protein and was used as starting material for the FPLC purification of soluble $rBoNTF(H_C)$ while the pellet was used as starting material for the resolubilized $rBoNTF(H_C)$ purification.

Example 4

Conventional Purification of $rBoNTF(H_C)$ from *P. pastoris*

Figure 21:
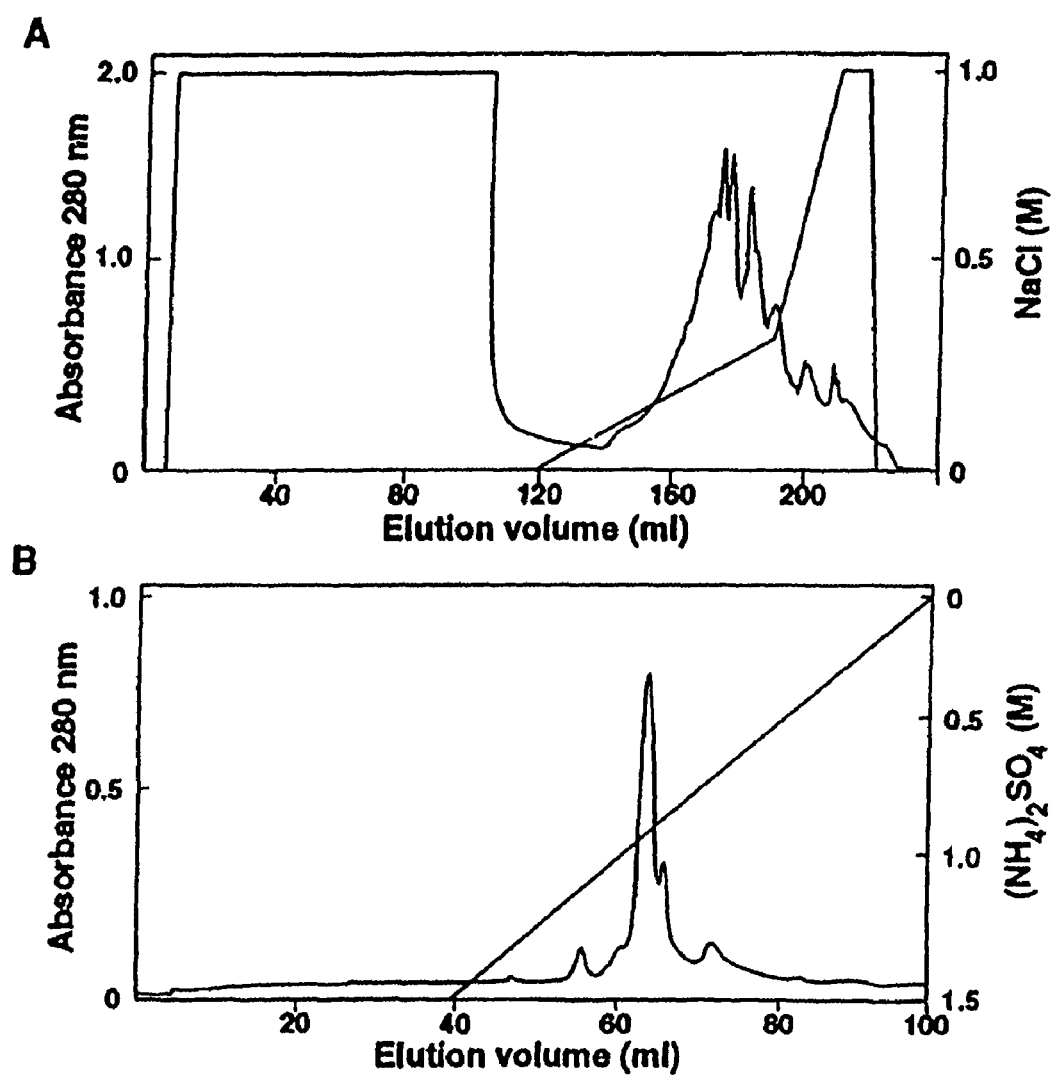
FIGS. 21A and 21B show purification of rBoNTF(Hc) by sequential chromatography.

The $rBoNTF(H_C)$ protein was purified to homogeneity using an FPLC system and two chromatographic steps. First, the material was subjected to cation exchange chromatography (FIG. 21A).

FPLC Purification of Soluble $rBoNTF(H_C)$

Soluble $rBoNTF(H_C)$ was purified by using a Pharmacia model 500 FPLC system (Pharmacia, Uppsala, Sweden) with programmed elution and $A_{280}$ monitoring. The starting material was loaded onto a Pharmacia HR 10/10 Mono S cation-exchange column equilibrated with 50 mM $Na_2HPO_4$/2 mM $Na_2EDTA$/1 mM PMSF, pH 6.8 (buffer A) at a flow rate of 2 ml/min (150 cm/h). The column was washed with 16 ml (2 bed volumes) of buffer A. Flow through and wash were collected separately and stored for subsequent analysis. Protein was eluted from the column with a linear gradient from 0 to 300 mM NaCl over 80 ml (10 bed volumes), then a linear gradient from 300 to 1000 mM NaCl over 20 ml (2.5 bed volumes), and then an isocratic gradient at 1000 mM over 10 ml (1.25 bed volumes). Four-ml fractions were collected throughout the linear and isocratic gradients. This step was highly efficient as most *pichia* proteins possess isoelectric points between pH 5 and 7 and, therefore, pass through the column without binding. Fractions eluting between 230 and 260 mM NaCl were positive for $rBoNTF(H_C)$ by Western blot analysis and were pooled. The pooled fractions were adjusted to 1.5 M ammonium sulfate by the slow addition of 2 M $(NH_4)_2SO_4$/50 mM $Na_2HPO_4$/2 mM $Na_2EDTA$/25 mM NaCl, pH 7.5 with stir bar agitation. A protein precipitate formed which consisted primarily of yeast proteins with a small amount of $rBoNTF(H_C)$ product (approximately 10%). The precipitate was removed by centrifugation at 6000 g for 10 min at 4° C. with a Sorval SS-34 rotor. Fortunately, when the pool of Mono S column fractions was diluted with ammonium sulfate, most of the $rBoNTF(H_C)$ product remained in solution (approximately 90%) while significant quantities of *pichia* proteins salted out. The first step enriched the desired product from <0.5 to 26% of the total protein (Table 2).

HIC was used as a second chromatographic step (FIG. 21B) and separated proteins based on their differences in surface hydrophobicity. It was determined that neopentyl chemistry provided the appropriate hydrophobic interaction with $rBoNTF(H_C)$. The supernatant was loaded onto a Pharmacia alkyl superose 10/10 hydrophobic interaction chromatography (HIC) column equilibrated with 1.5 M $(NH_4)_2SO_4$/50 mM $Na_2HPO_4$/2 mM $Na_2EDTA$/25 mM NaCl, pH 7.5 (buffer B) at a flow rate of 1 ml/min (75 cm/h). The column was washed with 8 ml (1 bed volume) of buffer B Protein was eluted from the column with a linear gradient of decreasing $(NH_4)_2SO_4$ from 1.5 to 0 M over 60 ml (7.5 bed volumes). The $rBoNTF(H_C)$ eluted from the HIC column at 0.92 M ammonium sulfate in a volume of 3 ml with a protein concentration of 0.52 mg/ml. Fractions positive by Western blot analysis and which only showed a single band by SDS/PAGE were pooled and dialyzed extensively in 50 mM $Na_2HPO_4$/2 mM $Na_2EDTA$, pH 6.8.

The recovery of purified product from cell extract was estimated to be greater than 42%, with a yield of 140 mg/kg of cell paste (Table 2). The resulting $rBoNTF(H_C)$ was judged to be greater than 98% pure as only a single band was detected by SDS-PAGE (FIG. 20) even when moderately (4 μg) overloaded. Capillary isoelectric focusing showed the antigen possessed an isoelectric point of 9.4 (data not shown), which is in reasonable agreement with the calculated pI of 9.1.

TABLE 2

Purification of soluble rBoNTF(Hc)
Total protein concentration was determined by Pierce BCA ™ assay.
rBoNTF(H$_c$) was identified by Western blot analysis and purity was
estimated by analysis of individual lanes of SDS/PAGE by pixel
densitometry using NIH imaging software.

| Step | Concentration (mg/ml) | Protein (mg) | rBoNTF(Hc) (mg) | Purity (%) | Fold Purification | Recovery (%) |
|---|---|---|---|---|---|---|
| Lysate | 11 | 1100 | 5.6 | <0.5 | — | 3.8 |
| Dialzed extract | 7.8 | 740 | 3.7 | <0.5 | — | 66 |
| Mono S | 1.2 | 9.6 | 2.5 | 26 | >52 | 45 |
| Alyl superose | 0.52 | 1.6 | 1.6 | 100 | 3.8 | 29 |

CD of Purified Soluble and Resolubilized rBoNTF(H$_C$)

Purified soluble and resolubilized rBoNTF(H$_C$) were subjected to CD spectroscopy in a Jasco 600 spectropolarimeter (Japan Spectroscopy company, Tokyo, Japan). Experiments were performed at a concentration of 30 µg/ml (0.62 µM) in a 1 cm path length cell in 10 mM Na$_2$HPO$_4$, pH 7.0. Spectra were obtained as an average of four accumulations, scanned from 260-200 nm, at a scan rate of 10 nm/min, with a 2 sec response, and a 1 nm band width. The temperature was maintained at 20° C. with a Peltier thermocontrol device.

Analysis of the far-UV circular dichroism spectrum (FIG. 22) of the purified antigen showed a positive peak at 233 nm and a minimum at 214 nm. This suggests the molecule is in a folded conformation and possesses considerable β-sheet.

Example 5

Purification of Resolubilized rBoNTF(H$_C$)

Western blot analysis revealed that approximately 30-40% of the total expressed rBoNTF(H$_C$) was present in the insoluble pellet after cell lysis. To investigate whether this insoluble protein could be recovered, the pellet was extracted in the denaturant urea and then dialyzed in nondenaturing buffer.

FPLC Purification of Resolubilized rBoNTF(H$_C$)

The cell lysate pellet was resuspended into 20 ml of 3 M urea/50 mM Na$_2$HPO$_4$, pH 7.0 and extracted 15 h at 4° C. on a Labquake rotator. The cellular components not solubilized by the denaturing buffer were removed by centrifugation with a Sorval SS-34 rotor at 15000 g for 10 min at 4° C. The supernatant was dialyzed extensively using 10 kDa MWCO Pierce Slide-A-Lyzer dialysis cassettes in buffer A. A slight precipitate formed during the dialysis which was removed by centrifugation as described above. Western blot analysis showed that rBoNTF(H$_C$) was present only in the supernatant, which was estimated to be about 35% pure by SDS/PAGE. The supernatant was loaded onto a Pharmacia HR 10/10 Mono S cation-exchange column and separated by the same conditions as above. Fractions containing only a single positive rBoNTF(H$_C$) band SDS/PAGE and Western blot analysis were pooled and dialyzed in 50 mM Na$_2$HPO$_4$/2 mM Na$_2$EDTA, pH 6.8 in 10 kDa MWCO dialysis cassettes. The final resolubilized rBoNTF(H$_C$) product was judged to be greater than 98% pure as determined by SDS/PAGE.

Figure 22:
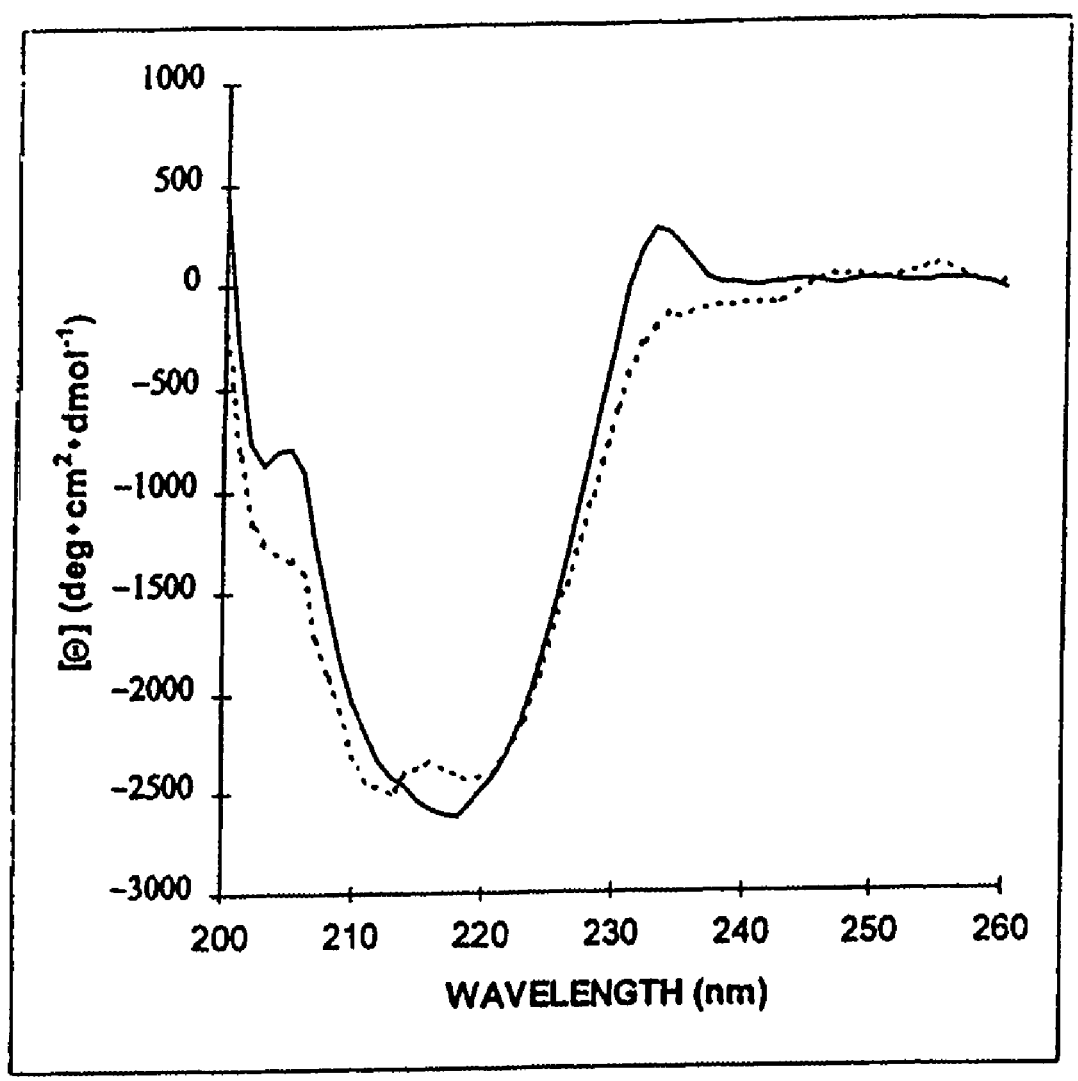
FIG. 22 shows CD spectra of purified soluble (—) and resolubilized (-) rBoNTF(Hc) at 30 µg/ml (0.62 µM) in 10 mM sodium phosphate, pH 7.0 in a 1-cm path length cell. Spectra were the average of four accumulations, scanned from 260 to 200 nm at a scan rate of 10 nm/min with a 2-s response and a 1-nm bandwidth. The temperature was maintained at 20° C. using a Peltier thermocontrol device.

After a single cation exchange chromatography separation step, the rBoNTF(H$_C$) was greater than 98% pure as judged by SDS-PAGE. The total yield of purified resolubilized rBoNTF(H$_C$) was 100 mg/kg of cell paste. The conformation of purified resolubilized antigen showed significant β-sheet as determined by CD spectral analysis (FIG. 22). However, the overall fold appeared slightly different than that shown by rBoNTF(H$_C$) purified from the cell lysate supernatant. The primary difference was the lack of a positive peak at 233 nm, indicating differences in β-sheet content.

Example 6

Mouse Immunogenicity and Efficacy Studies

To assess the immunogenicity of the recombinant rBoNTF (H$_C$), mice were inoculated with either one, two, or three doses of purified rBoNTF(H$_C$) from the soluble fraction of lysate at doses ranging from 0.008 to 5 µg per mouse.

Mouse Inoculations and BoNTF Toxin Challenge

Mice, Crl: CD-1, ICR mice (Charles River, N.C., U.S.A.) weighing 16-22 g on receipt, were injected intramuscularly (i.m.) with purified rBoNTF(H$_C$). Mice were challenged intraperitoneally (i.p.) 21 days after their last rBoNTF(H$_C$) injection with BoNTF toxin complex (Langeland strain) diluted in 0.2% (w/v) gelatin/0.4% (w/v) Na$_2$HPO$_4$, pH 6.2, in 100 µl total volume per mouse. Groups of five naive mice were also used as toxin controls. Mice were observed daily and deaths were recorded five days post challenge. All animal manipulations were in accordance with applicable regulations in AAALAC-accredited facilities.

The efficacy of the purified soluble rBoNTF(H$_C$) was determined by inoculating groups of five female mice with one, two, or three doses of 0.008, 0.04, 0.2, 1.0, or 5.0 µg rBoNTF(H$_C$) (diluted in 100 µl of 0.2% (v/v) Alhydrogel (Superfos Biosector, Kvistgaard, Denmark) in 0.9% (w/v) saline) per mouse at 14 day intervals. Two days before challenge, mice were bled retroorbitally and serum was collected for ELISA testing. Mice were challenged with 1000 mouse i.p. LD$_{50}$ of BoNTF toxin complex.

All of the mice, including five naïve controls, were challenged with 1000 mouse i.p. LD$_{50}$ of BoNTF toxin. The controls all died within 2-4 h. A dose response was observed from groups of mice receiving different numbers of inoculations (Table 3). A single inoculation of 5 µg protected four of five mice, while a dose of 0.2 µg or below protected one or no mice. Two and three inoculations protected four of five and five of five mice at doses of 0.2 and 0.04 µg, respectively. At all dose levels studied, the number of surviving mice increases with the number of inoculations.

Serum antibody titers for each individual mouse were determined by ELISA, followed by calculation of the geometric mean titers for each group in the study.

Mouse Serum ELISA

Individual mouse serum ELISAs were performed as previously described (Byrne, 1998) except for the following differences Botulinum neurotoxin serotype F (Langeland strain, Food Research Institute, University of Wisconsin, Madison, Wis., U.S.A.) was used as the coating antigen and the positive control for each assay was a mouse IgG monoclonal antibody, 7F8.G2.H3 (Brown, D. R., et al., (1997), "Identification and Characterization of a Neutralizing Monoclonal Antibody Against Botulinum Neurotoxin, Serotype F, Following Vaccination with Active Toxin," *Hybridoma*, 16:447-456).

TABLE 3

Survival, antibody group ELISA titers, and serum neutralization titers of mice after inoculation with purified soluble rBoNTF($H_c$)

Mice were chanllenged with 1000 i.p. $LD_{50}$ BoNTF toxin 21 days after last inoculation. Anitbody ELISA titers were measured as the reciprocal of the highest dilution having an $OD_{405}$ greater than 0.2 AU after correcting for background. Geometric mean ELISA titers were determined by taking the geometric mean of the logarithm of the individual titers. Standard deviations of the geometric means are also reported. If the ELISA titer was determined to be below the detection limit of the assay (<100), the ELISA titer was artibrarily assigned a value of 25. A geometric mean titer value of 1.4 means that all ELISA titers within that group were below the detection limit.

| Vaccination dose (µg) | Survival (alive/5 tested) | | | Geometric mean ELISA titers | | |
|---|---|---|---|---|---|---|
| | 1X | 2X | 3X | 1X | 2X | 3X |
| 0.008 | 0* | 0 | 2 | 1.4 | 1.4 | 1.6 ± 0.3 |
| 0.04 | 0 | 1 | 4 | 1.4 | 1.5 ± 0.3 | 2.4 ± 0.8 |
| 0.2 | 1 | 4 | 5 | 1.4 | 2.1 ± 0.9 | 2.9 ± 1.3 |
| 1.0 | 2 | 5 | 5 | 1.4 | 2.8 ± 0.3 | 4.3 ± 0.3 |
| 5.0 | 4 | 4 | 5 | 1.6 ± 0.3 | 2.8 ± 0.9 | 4.1 ± 0.5 |

*Only four mice were tested within this group

Mice were challenged with 1000 i.p. $LD_{50}$ BoNTF toxin 21 days after last inoculation. Antibody ELISA titers were measured as the reciprocal of the highest dilution having an $OD_{405}$ greater than 0.2 AU after correcting for background. Geometric mean ELISA titers were determined by taking the geometric mean of the logarithm of the individual titers. Standard deviations of the geometric means are also reported. If the ELISA titer was determined to be below the detection limit of the assay (<100), the ELISA titer was arbitrarily assigned a value of 25. A geometric mean titer value of 1.4 means that all ELISA titers within that group were below the detection limit.

Statistical Analysis

The logistic regression model was used to test associations of geometric mean ELISA titers and individual titers with survival by using SAS, version 6.10. Geometric mean titers correlated well with protection (Table 3). The three groups with no survivors had geometric means titers below the detection limit of the assay (1.4). Similarly, the four groups that showed complete protection had geometric means titers of 2.8 or greater. Individual mouse antibody titers correlated extremely well with protection (Table 4). Only 7 out of 38 mice survived whose titers were below 100. On the other hand, 34 out of 34 survived whose titers were 100 or greater. One mouse in the study could be classified as a "nonresponder." The mouse, receiving two injections at the highest dose level, had an antibody titer below the detection limit and did not survive the BoNTF challenge. The rest of the mice in that particular group had titers of 1600 or greater.

TABLE 4

Correlation of individual antibody ELISA titer with protection after inoculation with purified soluble rBoNTF($H_c$)

Serum was bled from each mouse individually. Titer is reciprocal of the highest dilution having an $Od_{405}$ greater than 0.2 AU after correcting from background. Mice were challenged with 1000 i.p. $LD_{50}$ BoNTF toxin 21 days after last inoculation.

| Individual ELISA titer | Survival (alive/total)* | % survival |
|---|---|---|
| <100 | 7/38 | 18.4 |
| 100 | 7/7 | 100 |
| 400 | 4/4 | 100 |
| 1600 | 11/11 | 100 |
| 6400 | 3/3 | 100 |
| 25600 | 9/9 | 100 |

*The individual antibody titers from three mice were not measured. Two mice did not offer enough serum and one mouse was not challenged.

Serum was bled from each mouse individually. Titer is reciprocal of the highest dilution having an $OD_{405}$ greater than 0.2 AU after correcting for background. Mice were challenged with 1000 i.p. $LD_{50}$ BoNTF toxin 21 days after last inoculation.

The resolubilized antigen was also evaluated for immunogencity and protective efficacy by its ability to protect mice from a BoNTF toxin challenge. Groups of 10 male mice each received three inoculations of either 1 µg or 5 µg of rBoNTF ($H_C$) (diluted in 100 µl 0.2% (v/v) Alhydrogel in 0.9% (w/v) saline) per mouse at 14 day intervals. Two days before challenge, mice were bled retroorbitally and serum was collected for ELISA testing. Mice inoculated with 1 µg doses were challenged with 5000 mouse i.p. $LD_{50}$ of BoNTF toxin. Ten of ten mice survived the challenge. Because 100% protection was observed with the group inoculated with 1 µg doses, the group that received three doses of 5 µg was subjected to a challenged level two orders of magnitude greater in order to test the limits of the antigen. Therefore, the 5 µg dose group was challenged with 500,000 mouse i.p. $LD_{50}$ of BoNTF toxin. None of the mice survived the challenge; however, a significant delay in time to death was observed (24-48 h). All the control mice succumbed within 2-4 h after challenge.

Example 7

Synthesis and Cloning of a Synthetic Gene Encoding rBoNTA ($H_C$)

The preparation of genetically engineered proteins to provide protection from the toxins produced by *Clostridium botulinum* was accomplished in *E. coli*.

Restriction endonucleases and DNA modifying enzymes were obtained from GIBCO BRL (Gaithersburg, Md.). Polymerase chain reaction (PCR) reagents were purchased from Perkin-Elmer Cetus (Norwalk, Conn.). SDS PAGE precast gels and running buffers were acquired from Amersham (Arlington Heights, Ill.). All oligonucleotides were synthesized by Macromolecular Resources (Ft. Collins, Colo.). ELISA reagents were obtained in house or from Sigma (St. Louis, Mo.) or Kirkegaard and Perry Laboratories (Gaithersburg, Md.).

The *Escherichia coli* host was K12DH5a, purchased as competent cells from GIBCO BRL. Expression vectors pMAL from New England Biolabs (Beverly, Mass.) and pKK233-2 from Pharmacia LKB (Piscataway, N.J.) were used according to the manufacturers' standard protocols. The DNA clone coding of the $H_C$ domain of C. botulinum toxin serotype A was pCBA3, kindly provided by Nigel Minton.

Oligonucleotide primers incorporating appropriate terminal restriction enzyme sites were used to PCR amplify the $H_C$ region of the C. botulinum clone pCBA3. Gel-purified insert DNA and vector DNA were cleaved with the appropriate restriction enzymes, purified on low melting point agarose, and ligated overnight at room temperature. Competent DH5a host cells were transformed according to suppliers' recommendations and plated on LB plates with 100 ug/ml ampicillin. Protein electrophoresis was run on precast 11-20% SDS PAGE at the manufacturer's recommended parameters. ELISA plates were incubated with capture antibody (horse anti-botulinum A polyclonal serum) overnight, then blocked with skim milk prior to application of various dilutions of test material, signal antibody (rabbit antibotulinum A polyclonal serum), signal HRP conjugated anti-(rabbit IgG) and ABTS substrate solution. Plates were read on an automated reader at 405 nm.

The sequence of the C fragment of the A chain was deduced as SEQ ID NO:38.

The C fragment protein sequence was reverse translated using E. coli optimal codon usage. The gene was then altered in many places to insert restriction sites, start codon, stop codon. Other changes were also effected to make the molecule more appropriate for use in the vector. Throughout, the fidelity of the protein sequence generated therefrom was maintained.

The sequence for the synthetic gene is SEQ ID NO:37.

This gene has been synthesized using a large number of oligomers of approximately 60-65 bases corresponding to the sequences of the + and − strands. The oligomers had overlaps of 7 bases. The oligomers were allowed to anneal and were ligated to form 5 subunits of 250-300 base pairs each. Each subunit had been designed to have restriction sites at their termini which allowed them to be assembled in the right order to form the complete gene. On confirmation there was shown that the correct gene had 7 deletion errors. These errors were repaired using in vitro mutagenesis and the repair sites sequenced to confirm.

Example 8

Synthesis and Cloning of a Synthetic Gene Encoding rBoNTB ($H_C$)

The C fragment for botulism toxin serotype B of Whelan was studied and the portion of the protein having the sequence of SEQ ID NO:40 (amino acids 853 to 1291 of Accession No. M81186) was defined as the C fragment.

The synthetic gene for expression in E. coli was produced in the manner described for synthesis of the gene for the C fragment of the A strand, namely, using a large number of oligomers of approximately 60-65 bases corresponding to the sequences of the + and − strands with overlaps of 7 bases. The oligomers were allowed to anneal and were ligated to form subunits of 250-300 base pairs each. Each subunit had been designed to have restriction sites at their termini which allowed them to be assembled in the right order to form the complete gene. The synthetic gene encoding the C fragment of the B toxin is SEQ ID NO:39.

Cloning:

Supernatants of sonicated, IPTG-induced recombinant pMAL fusion E. coli cultures were tested for the presence of the botulinum $H_C$ expression product by ELISA and SDS-PAGE gels stained with Coomassie brilliant blue were unsuccessful. Attempts to express $H_C$ fragment as a non-fusion product were unsuccessful. Initial characterization of plasmid DNA from putative clones in pKK233-2 demonstrated an insert of the expected size was present. In addition, SDS-PAGE indicated the presence of a protein of approximately 50 kDa after induction. However, the recombinants appeared unstable and further preparations of this and other cultures failed to reproduce these results. This approach was subsequently abandoned in favor of the fusion product expression.

Example 9

Immunization Trials

Although attempts to quantitate expressed $H_C$ fusion products were unsuccessful, limited immunization trials were performed on mice to evaluate the vaccine potential of the product. Initial vaccination employed concentrated, crude E. Coli lysate with complete Freund's adjuvant. Two weeks later, animals were boosted with amylose column-purified expression product with Freund's incomplete adjuvant. At this time, a second group of five animals received amylose purified product in Freund's incomplete adjuvant as a single vaccination. After two additional weeks, both groups were challenged intraperitoneally with a dose of 3 $LD_{50}$ of toxin. All eleven animals receiving two immunizations with $H_C$ survived while six of the twelve control animals receiving pMAL vector alone died. Likewise, all five animals receiving one $H_C$ vaccination survived while animals receiving the pMAL vector alone died.

Four weeks after the initial challenge with 3 $LD_{50}$ of toxin, nine of the eleven animals who had received two immunizations were exposed to 30, 300, or 1200 $LD_{50}$ doses of toxin. The animals succumbing to the toxin challenge of 30 and 300 $LD_{50}$ did not exhibit fatality typical of botulinum toxin poisoning in that they appeared healthy after 18 hours, but were dead a few hours thereafter. In contrast, the animal which died from the 1200 $LD_{50}$ dose appeared moribund when examined at 18 hours and remained so until death. This reaction is consistent with symptoms usually observed with botulinum toxin-induced paralysis. Additional data on second challenge is shown on Table 5. Hence, it was shown that immunization with the genetically engineered toxin protected against large doses of the toxin.

It is also possible to produce antibodies using the genetically engineered toxin. Because the toxin is not disease-producing in the animal, it is possible to produce large amounts of antitoxin more cheaply. It is also possible to produce antitoxin using hybridoma technology.

TABLE 5

PROTECTION OF MICE IMMUNIZED WITH $H_C$ OF A TOXIN DERIVED FROM SYNTHETIC GENE (# of deaths/total animals)

| Calculated challenge dose ($LD_{50}$) | Control (vector without insert) | Protected (Vector with insert) |
|---|---|---|
| 4 | 2/3 | 0/3 |
| 10 |  | 0/3 |
| 30 | 3/4 | 0/3 |
| 100 |  | 0/3 |
| 300 |  | 0/3 |
| 1000 |  | 0/3 |
| 3000 | 0/1 |  |

The animals received vaccinations of crude lysated cell material at 0, 2 and 4 weeks. Challenges were administered intraperitoneally with serotype A toxin at 5 weeks.

Example 10 rBoNTA(H$_C$) Purification and Protective Effect

Recombinant BoNTA(H$_C$) peptide was produced recombinantly in yeast. The first step in the purification process for BoNTA(H$_C$) was a Streamline expanded bed chromatography column. The product was eluted by a sodium chloride step gradient. Product eluted from the expanded bed chromatography column was estimated to be 10% pure with a total protein concentration of 0.92 mg/ml. After dialyzing the salt away, the material was loaded onto a mono S cation exchange column for further purification. Western blot and ELISA data indicated that BoNTA(H$_C$) eluted from the column at 110 mM sodium chloride. The Mono S pool was subjected to HIC as a final purification step and thus, the material was adjusted to 1.5 M ammonium sulfate. The Mono S product was loaded onto a HIC column and eluted with a gradient of decreasing ammonium sulfate. Product eluted at 1.04 M ammonium sulfate and BoNTA(H$_C$) immunologically positive fractions were combined and dialyzed to remove ammonium sulfate. Only a 50 kDa BoNTA(H$_C$) band was detected by SDS-PAGE and Western blot analysis and was judged to be greater than 95% pure after the final step. Protective effect of this purified material was measured by immunizing mice with 1 dose followed by challenge with 1000 LD50 of BoNTA(H$_C$). The results are shown in Table 6 below.

TABLE 6

Potency assay:
1 dose followed by challenge with 1000 LD50 of BoNTA(H$_C$)

| Dose (µg) | survival |
|---|---|
| 10 | 10/10 |
| 2.5 | 10/10 |
| 0.625 | 10/10 |
| 0.156 | 7/10 |
| 0.039 | 2/10 |
| 0.0098 | 0/10 |
| 0.0024 | 0/10 |

Example 11 rBoNTB(H$_C$) Purification and Protective Effect

Recombinant BoNTC(H$_C$) peptide was produced recombinantly in yeast. The first separation technique employed for the purification process for BoNTB(H$_C$) was Streamline chromatography (Pharmacia), which is a single pass expanded bed adsorption operation where proteins can be recovered from crude feed stock or cell lysate without prior clarification. Significant clean-up was accomplished in this step as the MES buffer system prohibited binding of a large percentage of unwanted proteins to the SP resin. Protein was loaded onto the column at a concentration of 123 mg/mL-resin, using 20 mM MES buffer, pH 5.7 with 10 mM NaCl. The product pool was eluted in a single step. Under the conditions investigated, on average 3.9% of the total protein loaded was recovered in the elution peak, and the product pool was approximately 70% BoNTB(H$_C$) fragment based on SDS-PAGE.

The second chromatography step in the process utilizes Poros HS, another strong cation exchange resin. The buffer system was similar to that used for Streamline SP, however enhanced selectivity of Poros HS enriched the product peak to about 85% purity. The product peak eluted during the gradient at approximately 130 mM NaCl. Strongly bound proteins were eluted with 1M NaCl.

The final chromatography step utilized a Poros PI column. Analysis of the PI fractions by SDS-PAGE and IEF revealed that the product band, a single band at 50 kD on SDS-PAGE, was present in the pH 8.0 fraction. Analysis of purified BoNTB(H$_C$) fragment by 2-D electrophoresis resulted in one major spot and two minor, faint spots from the PI-peak 1 fraction. Peak 2 contained several spots at two different molecular weights corresponding to 50 kD and 47 kD. Presumably these spots represent different isoforms. IEF banding patterns detected in the first dimension are in agreement with those seen in Phast IEF for the two peaks. The protective efficacy of this material was determined by potency assay of 1 dose followed by challenge with 1000 LD50 of BoNTB(H$_C$). The results are shown in the following Table 7.

TABLE 7

BoNTB(H$_C$)

| Dose (µg) | survival |
|---|---|
| 10 | 10/10 |
| 2.5 | 10/10 |
| 0.625 | 10/10 |
| 0.156 | 6/10 |
| 0.039 | 1/10 |
| 0.0098 | 0/10 |
| 0.0024 | 0/10 |

Example 12 rBoNTC(H$_C$) Purification and Protective Effect

Recombinant BoNTC(H$_C$) peptide was produced recombinantly in yeast. The initial chromatography step used for the purification process for BoNTC$_1$(H$_C$) was a Mono Q anion-exchange column. The column was equilibrated with 50 mM sodium phosphate, 0.2% (W/V) CHAPS, 2 mM EDTA, pH 7.0. The CHAPS was incorporated into the column buffers to allow product to elute from the column over a narrower sodium chloride concentration. Fractions positive for BoNTC$_1$(H$_C$) by Western analysis were pooled and adjusted to 1 M ammonium sulfate. A moderate precipitate formed which was removed by passing the material through a 0.2µ filtration unit. The clarified Mono Q product pool was subjected to hydrophobic interaction chromatography using a Pharmacia alkyl Superose column. This final step removed the remainder of the impurities liberating BoNTC$_1$(H$_C$) product which was estimated to be greater than 98% pure as judged by SDS/PAGE. Protective effect of this purified material was measured by immunizing mice with 1 dose followed by challenge with 1000 LD50 of BoNTC$_1$(H$_C$). The results are shown in Table 8 below.

TABLE 8

Potency Assay:
One dose followed by challenge with 1000 LD50 of BoNTC$_1$(H$_C$)

| Dose (µg) | Survival |
|---|---|
| 8.1 | 10/10 |
| 2.7 | 10/10 |
| 0.9 | 10/10 |
| 0.3 | 9/10 |
| 0.1 | 4/10 |

TABLE 8-continued

Potency Assay:
One dose followed by challenge with 1000 LD50 of BoNTC$_1$(H$_C$)

| Dose (μg) | Survival |
|---|---|
| 0.033 | 0/10 |
| 0.011 | 0/10 |

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, immunology, hybridoma technology, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

We claim:

1. The isolated and purified nucleic acid sequence identified as SEQ ID NO: 15.

2. The nucleic acid of claim 1, further comprising an expression control sequence operably linked to said nucleic acid sequence.

3. A method of preparing a polypeptide comprising the carboxy-terminal portion of the heavy chain of a botulinum neurotoxin serotype F, said method comprising transfecting an organism with the nucleic acid sequence of claim 1, culturing the transfected organism under conditions wherein the carboxy-terminal portion of the heavy chain of the botulinum neurotoxin is expressed, and the polypeptide is produced from the nucleic acid wherein the organism is selected from the group consisting of a gram negative bacterium, a yeast cell, and a cell of a mammalian cell line, and recovering said polypeptide from said transfected organism.

4. The method of claim 3 wherein said organism is *Escherichia coli*.

5. The method of claim 3 wherein said organism is *Pichia pastoris*.

6. The nucleic acid of claim 1, wherein the A+T content is less than about 70% of the total base composition.

7. The nucleic acid of claim 1, wherein the A+T content is less than about 60% of the total base composition.

8. A recombinant host cell comprising the nucleic acid of claim 1.

9. The recombinant host cell of claim 8, wherein expression of said nucleic acid in said host cell produces a protein comprising the heavy chain of a botulinum neurotoxin serotype F.

10. The recombinant host cell of claim 9, wherein said protein elicits an ELISA response to a botulinum neurotoxin serotype in an animal, said ELISA response being detectable upon about 100-fold dilution of serum from said animal.

11. The nucleic acid of claim 2 wherein said expression control sequence is a promoter.

12. The nucleic acid of claim 2 wherein said expression control sequence is an enhancer.

13. The nucleic acid of claim 1 wherein said nucleic acid is capable of being expressed in an organism selected from the group consisting of a gram negative bacterium, a yeast cell, and a cell of a mammalian cell line.

14. The nucleic acid of claim 13, wherein the gram negative bacteria is *Escherichia coli*.

15. The nucleic acid of claim 13, wherein the yeast is *Pichia pastoris*.

16. The recombinant host cell of claim 8 wherein said host cell is selected from the group consisting of a gram negative bacterium, a yeast cell, and a cell of a mammalian cell line.

17. The recombinant host cell of claim 16 wherein said gram negative bacteria is *Escherichia coli*.

18. The recombinant host cell of claim 16 wherein said yeast cell is *Pichia pastoris*.

19. The recombinant host cell of claim 10, wherein said protein is at least 0.75% (w/w) of the total cellular protein.

20. The recombinant host cell of claim 11, wherein said protein is at least 20% (w/w) of the total cellular protein.

* * * * *

SEQUENCE LISTING

<160> NUMBER OF SEQ ID NOS: 44

<210> SEQ ID NO 1
<211> LENGTH: 1332
<212> TYPE: DNA
<213> ORGANISM: Artificial Sequence
<220> FEATURE:
<223> OTHER INFORMATION: Synthetic construct based on BoNTA Hc

<400> SEQUENCE: 1

```
gaattcgaaa cgatgcgtct gctgtctacc ttcactgaat acatcaagaa catcatcaat      60
acctccatcc tgaacctgcg ctacgaatcc aatcacctga tcgacctgtc tcgctacgct     120
tccaaaatca acatcggttc taaagttaac ttcgatccga tcgacaagaa tcagatccag     180
ctgttcaatc tggaatcttc caaaatcgaa gttatcctga gaatgctat cgtatacaac     240 tctatgtacg aaaacttctc cacctccttc tggatccgta tcccgaaata cttcaactcc     300
atctctctga caatgaata caccatcatc aactgcatgg aaaacaattc tggttggaaa     360
gtatctctga actacggtga aatcatctgg actctgcagg acactcagga aatcaaacag     420
cgtgttgtat tcaaatactc tcagatgatc aacatctctg actacatcaa tgctggatc     480 ttcgttacca tcaccaacaa tcgtctgaat aactccaaaa tctacatcaa cggccgtctg     540
atcgaccaga aaccgatctc caatctgggt aacatccacg cttctaataa catcatgttc     600
aaactggacg gttgtcgtga cactcaccgc tacatctgga tcaaatactt caatctgttc     660
gacaaagaac tgaacgaaaa agaaatcaaa gacctgtacg acaaccagtc caattctggt     720
atcctgaaag acttctgggg tgactacctg cagtacgaca aaccgtacta catgctgaat     780
ctgtacgatc cgaacaaata cgttgacgtc aacaatgtag gtatccgcgg ttacatgtac     840
ctgaaaggtc cgcgtggttc tgttatgact accaacatct acctgaactc ttccctgtac     900
cgtggtacca aattcatcat caagaaatac gcgtctggta acaaggacaa tatcgttcgc     960
aacaatgatc gtgtatacat caatgttgta gttaagaaca aagaataccg tctggctacc    1020
aatgcttctc aggctggtgt agaaaagatc ttgtctgctc tggaaatccc ggacgttggt    1080
aatctgtctc aggtagttgt aatgaaatcc aagaacgacc agggtatcac taacaaatgc    1140
aaaatgaatc tgcaggacaa caatggtaac gatatcggtt tcatcggttt ccaccagttc    1200
aacaatatcg ctaaactggt tgcttccaac tggtacaatc gtcagatcga acgttcctct    1260
cgcactctgg gttgctcttg ggagttcatc ccggttgatg acgttgggg tgaacgtccg    1320 ctgtaagaat tc                                                        1332
```

-continued

<210> SEQ ID NO 2
<211> LENGTH: 437
<212> TYPE: PRT
<213> ORGANISM: Artificial Sequence
<220> FEATURE:
<223> OTHER INFORMATION: Encoded polypeptide of a synthetic construct
      based on BoNTA Hc

<400> SEQUENCE: 2

Met Arg Leu Leu Ser Thr Phe Thr Glu Tyr Ile Lys Asn Ile Ile Asn
 1               5                  10                  15

Thr Ser Ile Leu Asn Leu Arg Tyr Glu Ser Asn His Leu Ile Asp Leu
            20                  25                  30

Ser Arg Tyr Ala Ser Lys Ile Asn Ile Gly Ser Lys Val Asn Phe Asp
        35                  40                  45

Pro Ile Asp Lys Asn Gln Ile Gln Leu Phe Asn Leu Glu Ser Ser Lys
    50                  55                  60

Ile Glu Val Ile Leu Lys Asn Ala Ile Val Tyr Asn Ser Met Tyr Glu
65                  70                  75                  80

Asn Phe Ser Thr Ser Phe Trp Ile Arg Ile Pro Lys Tyr Phe Asn Ser
                85                  90                  95

Ile Ser Leu Asn Asn Glu Tyr Thr Ile Ile Asn Cys Met Glu Asn Asn
            100                 105                 110

Ser Gly Trp Lys Val Ser Leu Asn Tyr Gly Glu Ile Ile Trp Thr Leu
        115                 120                 125

Gln Asp Thr Gln Glu Ile Lys Gln Arg Val Val Phe Lys Tyr Ser Gln
    130                 135                 140

Met Ile Asn Ile Ser Asp Tyr Ile Asn Arg Trp Ile Phe Val Thr Ile
145                 150                 155                 160

Thr Asn Asn Arg Leu Asn Asn Ser Lys Ile Tyr Ile Asn Gly Arg Leu
                165                 170                 175

Ile Asp Gln Lys Pro Ile Ser Asn Leu Gly Asn Ile His Ala Ser Asn
            180                 185                 190

Asn Ile Met Phe Lys Leu Asp Gly Cys Arg Asp Thr His Arg Tyr Ile
        195                 200                 205

Trp Ile Lys Tyr Phe Asn Leu Phe Asp Lys Glu Leu Asn Glu Lys Glu
    210                 215                 220

Ile Lys Asp Leu Tyr Asp Asn Gln Ser Asn Ser Gly Ile Leu Lys Asp
225                 230                 235                 240

Phe Trp Gly Asp Tyr Leu Gln Tyr Asp Lys Pro Tyr Tyr Met Leu Asn
                245                 250                 255

Leu Tyr Asp Pro Asn Lys Tyr Val Asp Val Asn Asn Val Gly Ile Arg
            260                 265                 270

Gly Tyr Met Tyr Leu Lys Gly Pro Arg Gly Ser Val Met Thr Thr Asn
        275                 280                 285

Ile Tyr Leu Asn Ser Ser Leu Tyr Arg Gly Thr Lys Phe Ile Ile Lys
    290                 295                 300

Lys Tyr Ala Ser Gly Asn Lys Asp Asn Ile Val Arg Asn Asn Asp Arg
305                 310                 315                 320

Val Tyr Ile Asn Val Val Val Lys Asn Lys Glu Tyr Arg Leu Ala Thr
                325                 330                 335

Asn Ala Ser Gln Ala Gly Val Glu Lys Ile Leu Ser Ala Leu Glu Ile
            340                 345                 350

Pro Asp Val Gly Asn Leu Ser Gln Val Val Val Met Lys Ser Lys Asn

|     |     |     |     | 355 |     |     |     | 360 |     |     |     | 365 |     |     |
| --- | --- | --- | --- | --- | --- | --- | --- | --- | --- | --- | --- | --- | --- | --- |

Asp Gln Gly Ile Thr Asn Lys Cys Lys Met Asn Leu Gln Asp Asn Asn
            370                 375                 380

Gly Asn Asp Ile Gly Phe Ile Gly Phe His Gln Phe Asn Asn Ile Ala
385                 390                 395                 400

Lys Leu Val Ala Ser Asn Trp Tyr Asn Arg Gln Ile Glu Arg Ser Ser
                405                 410                 415

Arg Thr Leu Gly Cys Ser Trp Glu Phe Ile Pro Val Asp Asp Gly Trp
            420                 425                 430

Gly Glu Arg Pro Leu
            435

<210> SEQ ID NO 3
<211> LENGTH: 1323
<212> TYPE: DNA
<213> ORGANISM: Artificial Sequence
<220> FEATURE:
<223> OTHER INFORMATION: Synthetic construct based on BoNTA Hc

<400> SEQUENCE: 3

```
gaattcgaaa cgatgtctac cttcactgaa tacatcaaga acatcatcaa tacctccatc      60
ctgaacctgc gctacgaatc caatcacctg atcgacctgt ctcgctacgc ttccaaaatc     120
aacatcggtt ctaaagttaa cttcgatccg atcgacaaga atcagatcca gctgttcaat     180
ctggaatctt ccaaaatcga gttatcctg aagaatgcta tcgtatacaa ctctatgtac     240
gaaaacttct ccacctcctt ctggatccgt atcccgaaat acttcaactc catctctctg     300
aacaatgaat acaccatcat caactgcatg gaaaacaatt ctggttggaa agtatctctg     360
aactacggtg aaatcatctg gactctgcag gacactcagg aaatcaaaca gcgtgttgta     420
ttcaaatact ctcagatgat caacatctct gactacatca atcgctggat cttcgttacc     480
atcaccaaca atcgtctgaa taactccaaa atctacatca acggccgtct gatcgaccag     540
aaaccgatct ccaatctggg taacatccac gcttctaata acatcatgtt caaactggac     600
ggttgtcgtg acactcaccg ctacatctgg atcaaatact ccaatctgtt cgacaaagaa     660
ctgaacgaaa agaaatcaa agacctgtac gacaaccagt ccaattctgg tatcctgaaa     720
gacttctggg gtgactacct gcagtacgac aaaccgtact acatgctgaa tctgtacgat     780
ccgaacaaat acgttgacgt caacaatgta ggtatccgcg gttacatgta cctgaaaggt     840
ccgcgtggtt ctgttatgac taccaacatc tacctgaact cttccctgta ccgtggtacc     900
aaattcatca tcaagaaata cgcgtctggt aacaaggaca tatcgttcg caacaatgat     960
cgtgtataca tcaatgttgt agttaagaac aaagaatacc gtctggctac caatgcttct    1020
caggctggtg tagaaaagat cttgtctgct ctggaaatcc cggacgttgg taatctgtct    1080
caggtagttg taatgaaatc caagaacgac cagggtatca ctaacaaatg caaaatgaat    1140
ctgcaggaca caaatggtaa cgatatcggt ttcatcggtt tccaccagtt caacaatatc    1200
gctaaactgg ttgcttccaa ctggtacaat cgtcagatcg aacgttcctc tcgcactctg    1260
ggttgctctt gggagttcat cccggttgat gacggttggg gtgaacgtcc gctgtaagaa    1320
ttc                                                                  1323
```

<210> SEQ ID NO 4
<211> LENGTH: 434
<212> TYPE: PRT
<213> ORGANISM: Artificial Sequence
<220> FEATURE:

<223> OTHER INFORMATION: Encoded polypeptide of a synthetic construct based on BoNTA Hc

<400> SEQUENCE: 4

```
Met Ser Thr Phe Thr Glu Tyr Ile Lys Asn Ile Ile Asn Thr Ser Ile
1               5                   10                  15

Leu Asn Leu Arg Tyr Glu Ser Asn His Leu Ile Asp Leu Ser Arg Tyr
            20                  25                  30

Ala Ser Lys Ile Asn Ile Gly Ser Lys Val Asn Phe Asp Pro Ile Asp
        35                  40                  45

Lys Asn Gln Ile Gln Leu Phe Asn Leu Glu Ser Ser Lys Ile Glu Val
    50                  55                  60

Ile Leu Lys Asn Ala Ile Val Tyr Asn Ser Met Tyr Glu Asn Phe Ser
65                  70                  75                  80

Thr Ser Phe Trp Ile Arg Ile Pro Lys Tyr Phe Asn Ser Ile Ser Leu
                85                  90                  95

Asn Asn Glu Tyr Thr Ile Ile Asn Cys Met Glu Asn Asn Ser Gly Trp
            100                 105                 110

Lys Val Ser Leu Asn Tyr Gly Glu Ile Ile Trp Thr Leu Gln Asp Thr
        115                 120                 125

Gln Glu Ile Lys Gln Arg Val Val Phe Lys Tyr Ser Gln Met Ile Asn
    130                 135                 140

Ile Ser Asp Tyr Ile Asn Arg Trp Ile Phe Val Thr Ile Thr Asn Asn
145                 150                 155                 160

Arg Leu Asn Asn Ser Lys Ile Tyr Ile Asn Gly Arg Leu Ile Asp Gln
                165                 170                 175

Lys Pro Ile Ser Asn Leu Gly Asn Ile His Ala Ser Asn Asn Ile Met
            180                 185                 190

Phe Lys Leu Asp Gly Cys Arg Asp Thr His Arg Tyr Ile Trp Ile Lys
        195                 200                 205

Tyr Phe Asn Leu Phe Asp Lys Glu Leu Asn Glu Lys Glu Ile Lys Asp
    210                 215                 220

Leu Tyr Asp Asn Gln Ser Asn Ser Gly Ile Leu Lys Asp Phe Trp Gly
225                 230                 235                 240

Asp Tyr Leu Gln Tyr Asp Lys Pro Tyr Tyr Met Leu Asn Leu Tyr Asp
                245                 250                 255

Pro Asn Lys Tyr Val Asp Val Asn Asn Val Gly Ile Arg Gly Tyr Met
            260                 265                 270

Tyr Leu Lys Gly Pro Arg Gly Ser Val Met Thr Thr Asn Ile Tyr Leu
        275                 280                 285

Asn Ser Ser Leu Tyr Arg Gly Thr Lys Phe Ile Ile Lys Lys Tyr Ala
    290                 295                 300

Ser Gly Asn Lys Asp Asn Ile Val Arg Asn Asn Asp Arg Val Tyr Ile
305                 310                 315                 320

Asn Val Val Val Lys Asn Lys Glu Tyr Arg Leu Ala Thr Asn Ala Ser
                325                 330                 335

Gln Ala Gly Val Glu Lys Ile Leu Ser Ala Leu Glu Ile Pro Asp Val
            340                 345                 350

Gly Asn Leu Ser Gln Val Val Met Lys Ser Lys Asn Asp Gln Gly
        355                 360                 365

Ile Thr Asn Lys Cys Lys Met Asn Leu Gln Asp Asn Asn Gly Asn Asp
    370                 375                 380

Ile Gly Phe Ile Gly Phe His Gln Phe Asn Asn Ile Ala Lys Leu Val
385                 390                 395                 400
```

```
Ala Ser Asn Trp Tyr Asn Arg Gln Ile Glu Arg Ser Ser Arg Thr Leu
            405                 410                 415

Gly Cys Ser Trp Glu Phe Ile Pro Val Asp Asp Gly Trp Gly Glu Arg
            420                 425                 430

Pro Leu

<210> SEQ ID NO 5
<211> LENGTH: 1326
<212> TYPE: DNA
<213> ORGANISM: Artificial Sequence
<220> FEATURE:
<223> OTHER INFORMATION: Synthetic construct based on BoNTA Hc

<400> SEQUENCE: 5
gaattcgaaa cgatggcctc taccttcact gaatacatca gaacatcat caatacctcc        60 atcctgaacc tgcgctacga atccaatcac ctgatcgacc tgtctcgcta cgcttccaaa      120
atcaacatcg gttctaaagt taacttcgat ccgatcgaca agaatcagat ccagctgttc      180
aatctggaat cttccaaaat cgaagttatc ctgaagaatg ctatcgtata caactctatg      240
tacgaaaact tctccacctc cttctggatc cgtatcccga atacttcaa ctccatctct       300 ctgaacaatg aataccacca tcaactgc atggaaaaca attctggttg aaagtatct         360 ctgaactacg gtgaaatcat ctggactctg caggacactc aggaaatcaa acagcgtgtt      420
gtattcaaat actctcagat gatcaacatc tctgactaca tcaatcgctg gatcttcgtt      480
accatcacca caatcgtct gaataactcc aaaatctaca tcaacggccg tctgatcgac       540
cagaaaccga tctccaatct gggtaacatc cacgcttcta ataacatcat gttcaaactg      600
gacggttgtc gtgacactca ccgctacatc tggatcaaat acttcaatct gttcgacaaa     660
gaactgaacg aaaaagaaat caaagacctg tacgacaacc agtccaattc tggtatcctg      720
aaagacttct ggggtgacta cctgcagtac gacaaaccgt actacatgct gaatctgtac      780
gatccgaaca atacgttga cgtcaacaat gtaggtatcc gcggttacat gtacctgaaa      840
ggtccgcgtg gttctgttat gactaccaac atctacctga actcttccct gtaccgtggt      900
accaaattca tcatcaagaa atacgcgtct ggtaacaagg acaatatcgt tcgcaacaat      960
gatcgtgtat acatcaatgt tgtagttaag aacaaagaat accgtctggc taccaatgct     1020
tctcaggctg gtgtagaaaa gatcttgtct gctctggaaa tcccggacgt tggtaatctg     1080
tctcaggtag ttgtaatgaa atccaagaac gaccagggta tcactaacaa atgcaaaatg     1140
aatctgcagg acaacaatgg taacgatatc ggtttcatcg gtttccacca gttcaacaat     1200
atcgctaaac tggttgcttc caactggtac aatcgtcaga tcgaacgttc ctctcgcact     1260
ctgggttgct cttgggagtt catcccggtt gatgacggtt ggggtgaacg tccgctgtaa     1320
gaattc                                                               1326

<210> SEQ ID NO 6
<211> LENGTH: 435
<212> TYPE: PRT
<213> ORGANISM: Artificial Sequence
<220> FEATURE:
<223> OTHER INFORMATION: Encoded polypeptide of a synthetic construct
      based on BoNTA Hc

<400> SEQUENCE: 6

Met Ala Ser Thr Phe Thr Glu Tyr Ile Lys Asn Ile Ile Asn Thr Ser
1               5                   10                  15
```

```
Ile Leu Asn Leu Arg Tyr Glu Ser Asn His Leu Ile Asp Leu Ser Arg
        20                  25                  30

Tyr Ala Ser Lys Ile Asn Ile Gly Ser Lys Val Asn Phe Asp Pro Ile
        35                  40                  45

Asp Lys Asn Gln Ile Gln Leu Phe Asn Leu Glu Ser Ser Lys Ile Glu
50                  55                  60

Val Ile Leu Lys Asn Ala Ile Val Tyr Asn Ser Met Tyr Glu Asn Phe
65                  70                  75                  80

Ser Thr Ser Phe Trp Ile Arg Ile Pro Lys Tyr Phe Asn Ser Ile Ser
                85                  90                  95

Leu Asn Asn Glu Tyr Thr Ile Ile Asn Cys Met Glu Asn Asn Ser Gly
            100                 105                 110

Trp Lys Val Ser Leu Asn Tyr Gly Glu Ile Ile Trp Thr Leu Gln Asp
            115                 120                 125

Thr Gln Glu Ile Lys Gln Arg Val Val Phe Lys Tyr Ser Gln Met Ile
    130                 135                 140

Asn Ile Ser Asp Tyr Ile Asn Arg Trp Ile Phe Val Thr Ile Thr Asn
145                 150                 155                 160

Asn Arg Leu Asn Asn Ser Lys Ile Tyr Ile Asn Gly Arg Leu Ile Asp
            165                 170                 175

Gln Lys Pro Ile Ser Asn Leu Gly Asn Ile His Ala Ser Asn Asn Ile
            180                 185                 190

Met Phe Lys Leu Asp Gly Cys Arg Asp Thr His Arg Tyr Ile Trp Ile
        195                 200                 205

Lys Tyr Phe Asn Leu Phe Asp Lys Glu Leu Asn Glu Lys Glu Ile Lys
        210                 215                 220

Asp Leu Tyr Asp Asn Gln Ser Asn Ser Gly Ile Leu Lys Asp Phe Trp
225                 230                 235                 240

Gly Asp Tyr Leu Gln Tyr Asp Lys Pro Tyr Tyr Met Leu Asn Leu Tyr
            245                 250                 255

Asp Pro Asn Lys Tyr Val Asp Val Asn Asn Val Gly Ile Arg Gly Tyr
            260                 265                 270

Met Tyr Leu Lys Gly Pro Arg Gly Ser Val Met Thr Thr Asn Ile Tyr
        275                 280                 285

Leu Asn Ser Ser Leu Tyr Arg Gly Thr Lys Phe Ile Ile Lys Lys Tyr
        290                 295                 300

Ala Ser Gly Asn Lys Asp Asn Ile Val Arg Asn Asn Asp Arg Val Tyr
305                 310                 315                 320

Ile Asn Val Val Val Lys Asn Lys Glu Tyr Arg Leu Ala Thr Asn Ala
            325                 330                 335

Ser Gln Ala Gly Val Glu Lys Ile Leu Ser Ala Leu Glu Ile Pro Asp
            340                 345                 350

Val Gly Asn Leu Ser Gln Val Val Val Met Lys Ser Lys Asn Asp Gln
        355                 360                 365

Gly Ile Thr Asn Lys Cys Lys Met Asn Leu Gln Asp Asn Asn Gly Asn
    370                 375                 380

Asp Ile Gly Phe Ile Gly Phe His Gln Phe Asn Asn Ile Ala Lys Leu
385                 390                 395                 400

Val Ala Ser Asn Trp Tyr Asn Arg Gln Ile Glu Arg Ser Ser Arg Thr
            405                 410                 415

Leu Gly Cys Ser Trp Glu Phe Ile Pro Val Asp Asp Gly Trp Gly Glu
        420                 425                 430

Arg Pro Leu
```

-continued

435

<210> SEQ ID NO 7
<211> LENGTH: 1341
<212> TYPE: DNA
<213> ORGANISM: Artificial Sequence
<220> FEATURE:
<223> OTHER INFORMATION: Synthetic construct based on BoNTB Hc

<400> SEQUENCE: 7
gaattcacga tggccaacaa atacaattcc gaaatcctga acaatatcat cctgaacctg 60
cgttacaaag acaacaatct gatcgatctg tctggttacg gtgctaaagt tgaagtatac 120
gacggtgttg aactgaatga caagaaccag ttcaaactga cctcttccgc taactctaag 180
atccgtgtta ctcagaatca gaacatcatc ttcaactccg tattcctgga cttctctgtt 240
tccttctgga ttcgtatccc gaaatacaag aacgacggta tccagaatta catccacaat 300
gaatacacca tcatcaactg catgaagaat aactctggtt ggaagatctc catccgcggt 360
aaccgtatca tctggactct gatcgatatc aacggtaaga ccaaatctgt attcttcgaa 420
tacaacatcc gtgaagacat ctctgaatac atcaatcgct ggttcttcgt taccatcacc 480
aataacctga acaatgctaa aatctacatc aacggtaaac tggaatctaa taccgacatc 540
aaagacatcc gtgaagttat cgctaacggt gaaatcatct tcaaactgga cggtgacatc 600
gatcgtaccc agttcatctg gatgaaatac ttctccatct tcaacaccga actgtctcag 660
tccaatatcg aagaacggta caagatccag tcttactccg aatacctgaa agacttctgg 720
ggtaatccgc tgatgtacaa caaagaatac tatatgttca atgctggtaa caagaactct 780
tacatcaaac tgaagaaaga ctctccggtt ggtgaaatcc tgactcgttc caaatacaac 840
cagaactcta aatacatcaa ctaccgcgac ctgtacatcg gtgaaaagtt catcatccgt 900
cgcaaatcta actctcagtc catcaatgat gacatcgtac gtaaagaaga ctacatctac 960
ctggacttct tcaacctgaa tcaggaatgg cgtgtataca cctacaagta cttcaagaaa 1020
gaagaagaaa agcttttcct ggctccgatc tctgattccg acgaactcta caacaccatc 1080
cagatcaaag aatacgacga acagccgacc tactcttgcc agctgctgtt caagaaagat 1140
gaagaatcta ctgacgaaat cggtctgatc ggtatccacc gtttctacga atctggtatc 1200
gtattcgaag aatacaaaga ctacttctgc atctccaaat ggtacctgaa ggaagttaaa 1260
cgcaaaccgt acaacctgaa actgggttgc aattggcagt tcatcccgaa agacgaaggt 1320
tggaccgaat agtaagaatt c 1341

<210> SEQ ID NO 8
<211> LENGTH: 440
<212> TYPE: PRT
<213> ORGANISM: Artificial Sequence
<220> FEATURE:
<223> OTHER INFORMATION: Encoded polypeptide of a synthetic construct
      based on BoNTB Hc

<400> SEQUENCE: 8

Met Ala Asn Lys Tyr Asn Ser Glu Ile Leu Asn Asn Ile Ile Leu Asn
1               5                   10                  15

Leu Arg Tyr Lys Asp Asn Asn Leu Ile Asp Leu Ser Gly Tyr Gly Ala
            20                  25                  30

Lys Val Glu Val Tyr Asp Gly Val Glu Leu Asn Asp Lys Asn Gln Phe
        35                  40                  45

Lys Leu Thr Ser Ser Ala Asn Ser Lys Ile Arg Val Thr Gln Asn Gln

```
                50               55               60
Asn Ile Ile Phe Asn Ser Val Phe Leu Asp Phe Ser Val Ser Phe Trp
 65               70                  75                      80

Ile Arg Ile Pro Lys Tyr Lys Asn Asp Gly Ile Gln Asn Tyr Ile His
                 85                  90                  95

Asn Glu Tyr Thr Ile Ile Asn Cys Met Lys Asn Asn Ser Gly Trp Lys
                100                 105                 110

Ile Ser Ile Arg Gly Asn Arg Ile Ile Trp Thr Leu Ile Asp Ile Asn
                115                 120                 125

Gly Lys Thr Lys Ser Val Phe Phe Glu Tyr Asn Ile Arg Glu Asp Ile
    130                 135                 140

Ser Glu Tyr Ile Asn Arg Trp Phe Phe Val Thr Ile Thr Asn Asn Leu
145                 150                 155                 160

Asn Asn Ala Lys Ile Tyr Ile Asn Gly Lys Leu Glu Ser Asn Thr Asp
                165                 170                 175

Ile Lys Asp Ile Arg Glu Val Ile Ala Asn Gly Glu Ile Ile Phe Lys
                180                 185                 190

Leu Asp Gly Asp Ile Asp Arg Thr Gln Phe Ile Trp Met Lys Tyr Phe
                195                 200                 205

Ser Ile Phe Asn Thr Glu Leu Ser Gln Ser Asn Ile Glu Glu Arg Tyr
210                 215                 220

Lys Ile Gln Ser Tyr Ser Glu Tyr Leu Lys Asp Phe Trp Gly Asn Pro
225                 230                 235                 240

Leu Met Tyr Asn Lys Glu Tyr Tyr Met Phe Asn Ala Gly Asn Lys Asn
                245                 250                 255

Ser Tyr Ile Lys Leu Lys Lys Asp Ser Pro Val Gly Glu Ile Leu Thr
                260                 265                 270

Arg Ser Lys Tyr Asn Gln Asn Ser Lys Tyr Ile Asn Tyr Arg Asp Leu
                275                 280                 285

Tyr Ile Gly Glu Lys Phe Ile Ile Arg Arg Lys Ser Asn Ser Gln Ser
                290                 295                 300

Ile Asn Asp Asp Ile Val Arg Lys Glu Asp Tyr Ile Tyr Leu Asp Phe
305                 310                 315                 320

Phe Asn Leu Asn Gln Glu Trp Arg Val Tyr Thr Tyr Lys Tyr Phe Lys
                325                 330                 335

Lys Glu Glu Glu Lys Leu Phe Leu Ala Pro Ile Ser Asp Ser Asp Glu
                340                 345                 350

Leu Tyr Asn Thr Ile Gln Ile Lys Glu Tyr Asp Glu Gln Pro Thr Tyr
                355                 360                 365

Ser Cys Gln Leu Leu Phe Lys Lys Asp Glu Glu Ser Thr Asp Glu Ile
370                 375                 380

Gly Leu Ile Gly Ile His Arg Phe Tyr Glu Ser Gly Ile Val Phe Glu
385                 390                 395                 400

Glu Tyr Lys Asp Tyr Phe Cys Ile Ser Lys Trp Tyr Leu Lys Glu Val
                405                 410                 415

Lys Arg Lys Pro Tyr Asn Leu Lys Leu Gly Cys Asn Trp Gln Phe Ile
                420                 425                 430

Pro Lys Asp Glu Gly Trp Thr Glu
        435                 440

<210> SEQ ID NO 9
<211> LENGTH: 1371
<212> TYPE: DNA
<213> ORGANISM: Artificial Sequence
```

<220> FEATURE:
<223> OTHER INFORMATION: Synthetic construct based on BoNTC1 Hc

<400> SEQUENCE: 9

```
gaattcacga tgaccatccc attcaacatc ttctcctaca ccaacaactc cctgttgaag      60
gacatcatca acgagtactt caacaacatc aacgactcca agatcctgtc cctgcagaac     120
cgtaagaaca ccttggtcga cacctccggt tacaacgccg aggtctccga ggagggtgac     180
gtccagctga acccaatctt cccattcgac ttcaagctgg gttcctccgg tgaggacaga     240
ggtaaggtca tcgtcaccca gaacgagaac atcgtctaca actccatgta cgagtccttc     300
tccatctcct tctggatcag aatcaacaag tgggtctcca acttgccagg ttacaccatc     360
atcgactccg tcaagaacaa ctccggttgg tccatcggta tcatctccaa cttcctggtc     420
ttcaccctga agcagaacga ggactccgag cagtccatca acttctccta cgacatctcc     480
aacaacgctc tggttacaa caagtggttc ttcgtcaccg tcaccaacaa catgatgggt     540
aacatgaaga tctacatcaa cggtaagctg atcgacacca tcaaggtcaa ggagttgacc     600
ggtatcaact tctccaagac catcaccttc gagatcaaca agatcccaga caccggtctg     660
atcacctccg actccgacaa catcaacatg tggatccgtg acttctacat cttcgccaag     720
gagttggacg gtaaggacat caacatcctg ttcaactcct tgcagtacac caacgtcgtc     780
aaggactact ggggtaacga cctgagatac aacaaggagt actacatggt caacatcgac     840
tacttgaaca gatacatgta cgccaactcc agacagatcg tcttcaacac cagacgtaac     900
aacaacgact tcaacgaggg ttacaagatc atcatcaagc gtatcagagg taacaccaac     960
gacaccagag tcagaggtgg tgacatcctg tacttcgaca tgactatcaa caacaaggcc    1020
tacaacctgt tcatgaagaa cgagaccatg tacgccgaca ccactccac cgaggacatc    1080
tacgccatcg gtctgcgtga gcagaccaag gacatcaacg acaacatcat cttccagatc    1140
cagccaatga caacacttta ctactacgct tcccagatct tcaagtccaa cttcaacggt    1200
gagaacatct ccggtatctg ttccatcggt acctacagat tcgtctgggt tggtgactgg    1260
tacagacaca actacttggt tccaactgtc aagcagggta actacgcctc cttgctggag    1320
tccacttcca cccactgggg attcgtccca gtctccgagt aataggaatt c             1371
```

<210> SEQ ID NO 10
<211> LENGTH: 450
<212> TYPE: PRT
<213> ORGANISM: Artificial Sequence
<220> FEATURE:
<223> OTHER INFORMATION: Encoded polypeptide of a synthetic construct based on BoNTC1 Hc

<400> SEQUENCE: 10

```
Met Thr Ile Pro Phe Asn Ile Phe Ser Tyr Thr Asn Asn Ser Leu Leu
  1               5                  10                  15

Lys Asp Ile Ile Asn Glu Tyr Phe Asn Asn Ile Asn Asp Ser Lys Ile
             20                  25                  30

Leu Ser Leu Gln Asn Arg Lys Asn Thr Leu Val Asp Thr Ser Gly Tyr
         35                  40                  45

Asn Ala Glu Val Ser Glu Glu Gly Asp Val Gln Leu Asn Pro Ile Phe
     50                  55                  60

Pro Phe Asp Phe Lys Leu Gly Ser Ser Gly Glu Asp Arg Gly Lys Val
 65                  70                  75                  80

Ile Val Thr Gln Asn Glu Asn Ile Val Tyr Asn Ser Met Tyr Glu Ser
                 85                  90                  95
```

```
Phe Ser Ile Ser Phe Trp Ile Arg Ile Asn Lys Trp Val Ser Asn Leu
                100                 105                 110
Pro Gly Tyr Thr Ile Ile Asp Ser Val Lys Asn Asn Ser Gly Trp Ser
            115                 120                 125
Ile Gly Ile Ile Ser Asn Phe Leu Val Phe Thr Leu Lys Gln Asn Glu
        130                 135                 140
Asp Ser Glu Gln Ser Ile Asn Phe Ser Tyr Asp Ile Ser Asn Asn Ala
145                 150                 155                 160
Pro Gly Tyr Asn Lys Trp Phe Phe Val Thr Val Thr Asn Asn Met Met
                165                 170                 175
Gly Asn Met Lys Ile Tyr Ile Asn Gly Lys Leu Ile Asp Thr Ile Lys
                180                 185                 190
Val Lys Glu Leu Thr Gly Ile Asn Phe Ser Lys Thr Ile Thr Phe Glu
            195                 200                 205
Ile Asn Lys Ile Pro Asp Thr Gly Leu Ile Thr Ser Asp Ser Asp Asn
        210                 215                 220
Ile Asn Met Trp Ile Arg Asp Phe Tyr Ile Phe Ala Lys Glu Leu Asp
225                 230                 235                 240
Gly Lys Asp Ile Asn Ile Leu Phe Asn Ser Leu Gln Tyr Thr Asn Val
                245                 250                 255
Val Lys Asp Tyr Trp Gly Asn Asp Leu Arg Tyr Asn Lys Glu Tyr Tyr
            260                 265                 270
Met Val Asn Ile Asp Tyr Leu Asn Arg Tyr Met Tyr Ala Asn Ser Arg
        275                 280                 285
Gln Ile Val Phe Asn Thr Arg Arg Asn Asn Asn Asp Phe Asn Glu Gly
        290                 295                 300
Tyr Lys Ile Ile Ile Lys Arg Ile Arg Gly Asn Thr Asn Asp Thr Arg
305                 310                 315                 320
Val Arg Gly Gly Asp Ile Leu Tyr Phe Asp Met Thr Ile Asn Asn Lys
                325                 330                 335
Ala Tyr Asn Leu Phe Met Lys Asn Glu Thr Met Tyr Ala Asp Asn His
                340                 345                 350
Ser Thr Glu Asp Ile Tyr Ala Ile Gly Leu Arg Glu Gln Thr Lys Asp
            355                 360                 365
Ile Asn Asp Asn Ile Ile Phe Gln Ile Gln Pro Met Asn Asn Thr Tyr
        370                 375                 380
Tyr Tyr Ala Ser Gln Ile Phe Lys Ser Asn Phe Asn Gly Glu Asn Ile
385                 390                 395                 400
Ser Gly Ile Cys Ser Ile Gly Thr Tyr Arg Phe Arg Leu Gly Gly Asp
                405                 410                 415
Trp Tyr Arg His Asn Tyr Leu Val Pro Thr Val Lys Gln Gly Asn Tyr
                420                 425                 430
Ala Ser Leu Leu Glu Ser Thr Ser Thr His Trp Gly Phe Val Pro Val
            435                 440                 445
Ser Glu
    450

<210> SEQ ID NO 11
<211> LENGTH: 1374
<212> TYPE: DNA
<213> ORGANISM: Artificial Sequence
<220> FEATURE:
<223> OTHER INFORMATION: Synthetic construct based on BoNTD Hc

<400> SEQUENCE: 11
```

```
gaattcacga tgcgtttgaa ggctaaggtc aacgagtcct tcgagaacac catgccattc      60
aacatcttct cctacaccaa caactccttg ttgaaggaca tcatcaacga gtacttcaac     120
tccatcaacg actccaagat cttgtccttg cagaacaaga gaacgccttt ggtcgacacc     180
tccggttaca acgccgaggt cagagtcggt gacaacgtcc agttgaacac catctacacc     240
aacgacttca agttgtcctc ttccggtgac aagatcatcg tcaacttgaa caacaacatc     300
ttgtactccg ccatctacga gaactcctct gtctccttct ggatcaagat ctccaaggac     360
ttgaccaact cccacaacga gtacaccatc atcaactcca tcgagcagaa ctccggttgg     420
aagttgtgta tccgtaacgg taacatcgag tggatcttgc aggacgtcaa ccgtaagtac     480
aagtccttga tcttcgacta ctccgagtcc ttgtcccaca ccggttacac caacaagtgg     540
ttcttcgtca ccatcaccaa caacatcatg ggttacatga agttgtacat caacggtgag     600
ttgaagcagt cccagaagat cgaggacctg gacgaggtca agctggacaa gaccatcgtc     660
ttcggtatcg acgagaacat cgacgagaac cagatgttgt ggatccgtga cttcaacatc     720
ttctccaagg agctgtccaa cgaggacatc aacatcgtct acgagggtca gatcctgagg     780
aacgtcatca aggactactg gggtaaccca ctgaagttcg acaccgagta ctacatcatc     840
aacgacaact acatcgaccg ttacatcgcc cagagtccaa cgtcctggt cctggtccag     900 taccctgacc gttccaagct gtacaccggt aaccctatca ccatcaagtc cgtctccgac     960
aagaacccct actcccgtat cctgaacggt gacaacatca tcctgcacat gctgtacaac    1020
tcccgtaagt acatgatcat ccgtgacacc gacaccatct acgccaccca gggtggtgac    1080
tgttcccaga actgtgtcta cgccctgaag ctgcagtcca acctgggtaa ctacggtatc    1140
ggtatcttct ccatcaagaa catcgtctcc aagaacaagt actgctccca gatcttctcc    1200
tccttccgtg agaacaccat gctgctggcc gacatctaca gccttggcg tttctccttc    1260 aagaacgcct acactcctgt cgccgtcacc aactacgaga ccaagctgct gtccacctcc    1320
tccttctgga agttcatctc ccgtgaccca ggttgggtcg agtaatagga attc          1374
```

<210> SEQ ID NO 12
<211> LENGTH: 451
<212> TYPE: PRT
<213> ORGANISM: Artificial Sequence
<220> FEATURE:
<223> OTHER INFORMATION: Encoded polypeptide of a synthetic construct based on BoNTD Hc

<400> SEQUENCE: 12

```
Met Arg Leu Lys Ala Lys Val Asn Glu Ser Phe Glu Asn Thr Met Pro
 1               5                  10                  15

Phe Asn Ile Phe Ser Tyr Thr Asn Asn Ser Leu Leu Lys Asp Ile Ile
             20                  25                  30

Asn Glu Tyr Phe Asn Ser Ile Asn Asp Ser Lys Ile Leu Ser Leu Gln
         35                  40                  45

Asn Lys Lys Asn Ala Leu Val Asp Thr Ser Gly Tyr Asn Ala Glu Val
     50                  55                  60

Arg Val Gly Asp Asn Val Gln Leu Asn Thr Ile Tyr Thr Asn Asp Phe
 65                  70                  75                  80

Lys Leu Ser Ser Ser Gly Asp Lys Ile Ile Val Asn Leu Asn Asn Asn
                 85                  90                  95

Ile Leu Tyr Ser Ala Ile Tyr Glu Asn Ser Ser Val Ser Phe Trp Ile
            100                 105                 110
```

Lys Ile Ser Lys Asp Leu Thr Asn Ser His Asn Glu Tyr Thr Ile Ile
            115                 120                 125

Asn Ser Ile Glu Gln Asn Ser Gly Trp Lys Leu Cys Ile Arg Asn Gly
        130                 135                 140

Asn Ile Glu Trp Ile Leu Gln Asp Val Asn Arg Lys Tyr Lys Ser Leu
145                 150                 155                 160

Ile Phe Asp Tyr Ser Glu Ser Leu Ser His Thr Gly Tyr Thr Asn Lys
                165                 170                 175

Trp Phe Phe Val Thr Ile Thr Asn Asn Ile Met Gly Tyr Met Lys Leu
            180                 185                 190

Tyr Ile Asn Gly Glu Leu Lys Gln Ser Gln Lys Ile Glu Asp Leu Asp
        195                 200                 205

Glu Val Lys Leu Asp Lys Thr Ile Val Phe Gly Ile Asp Glu Asn Ile
210                 215                 220

Asp Glu Asn Gln Met Leu Trp Ile Arg Asp Phe Asn Ile Phe Ser Lys
225                 230                 235                 240

Glu Leu Ser Asn Glu Asp Ile Asn Ile Val Tyr Glu Gly Gln Ile Leu
                245                 250                 255

Arg Asn Val Ile Lys Asp Tyr Trp Gly Asn Pro Leu Lys Phe Asp Thr
            260                 265                 270

Glu Tyr Tyr Ile Ile Asn Asp Asn Tyr Ile Asp Arg Tyr Ile Ala Pro
        275                 280                 285

Glu Ser Asn Val Leu Val Leu Val Gln Tyr Pro Asp Arg Ser Lys Leu
        290                 295                 300

Tyr Thr Gly Asn Pro Ile Thr Ile Lys Ser Val Ser Asp Lys Asn Pro
305                 310                 315                 320

Tyr Ser Arg Ile Leu Asn Gly Asp Asn Ile Ile Leu His Met Leu Tyr
                325                 330                 335

Asn Ser Arg Lys Tyr Met Ile Ile Arg Asp Thr Asp Thr Ile Tyr Ala
            340                 345                 350

Thr Gln Gly Gly Asp Cys Ser Gln Asn Cys Val Tyr Ala Leu Lys Leu
        355                 360                 365

Gln Ser Asn Leu Gly Asn Tyr Gly Ile Gly Ile Phe Ser Ile Lys Asn
        370                 375                 380

Ile Val Ser Lys Asn Lys Tyr Cys Ser Gln Ile Phe Ser Ser Phe Arg
385                 390                 395                 400

Glu Asn Thr Met Leu Leu Ala Asp Ile Tyr Lys Pro Trp Arg Phe Ser
                405                 410                 415

Phe Lys Asn Ala Tyr Thr Pro Val Ala Val Thr Asn Tyr Glu Thr Lys
            420                 425                 430

Leu Leu Ser Thr Ser Ser Phe Trp Lys Phe Ile Ser Arg Asp Pro Gly
        435                 440                 445

Trp Val Glu
    450

<210> SEQ ID NO 13
<211> LENGTH: 1400
<212> TYPE: DNA
<213> ORGANISM: Artificial Sequence
<220> FEATURE:
<223> OTHER INFORMATION: Synthetic construct based on BoNTE Hc

<400> SEQUENCE: 13
gaattcacca tgggagagag tcagcaagaa ctaaattcta tggtaactga taccctaaat      60
aatagtattc cttttaagct tcttcttat acagatgata aaatttttaat ttcctacttc     120

-continued

```
aacaagttct tcaagagaat taagtcttct tccgttttaa acatgagata caagaatgat      180
aaatacgtcg acacttccgg ttacgactcc aatatcaaca ttaacggtga cgtgtacaag      240
tacccaacta acaaaaacca attcggtatc tacaacgaca agcttactga gctgaacatc      300
tctcaaaacg actacattat ctacgacaac aagtacaaga acttctctat ttctttctgg      360
gtcaggattc ctaactacga caacaagatc gtcaacgtta acaacgagta cactatcatc      420
aactgtatga gagacaacaa ctccggttgg aaggtctctc ttaaccacaa cgagatcatt      480
tggaccttgc aagacaacgc aggtattaac caaaagttag cattcaacta cggtaacgca      540
aacggtattt ctgactacat caacaagtgg attttcgtca ctatcactaa cgacagatta      600
ggtgactcta agctttacat taacggtaac ttaatcgacc aaaagtccat tttaaactta      660
ggtaacattc acgtttctga acatcttta ttcaagatcg ttaactgcag ttacaccaga       720
tacattggca ttagatactt caacattttc gacaaggagt tagacgagac cgagattcaa      780
actttataca gcaacgaacc taacaccaat attttgaagg acttctgggg taactacttg      840
ctttacgaca aggaatacta cttattaaac gtgttaaagc caaacaactt cattgatagg      900
agaaaggatt ctactttaag cattaacaac atcagaagca ctattctttt agctaacaga      960
ttatactctg gtatcaaggt taagatccaa agagttaaca actcttctac taacgataac     1020
cttgttagaa agaacgatca ggtctatatt aacttcgtcg ctagcaagac tcacttattc     1080
ccattatatg ctgataccgc taccaccaac aaggagaaga ccatcaagat ctcctcctct     1140
ggcaacagat taaccaagt cgtcgttatg aactccgtcg gtaacaactg taccatgaac      1200
tttaaaaata ataatggaaa taatattggg ttgttaggtt tcaaggcaga tactgtagtt     1260
gctagtactt ggtattatac ccacatgaga gatcacacca acagcaatgg atgttttgg      1320 aactttattt ctgaagaaca tggatggcaa gaaaaataat agggatccgc ggccgcacgc     1380
gtcccgggac tagtgaattc                                                 1400
```

<210> SEQ ID NO 14
<211> LENGTH: 449
<212> TYPE: PRT
<213> ORGANISM: Artificial Sequence
<220> FEATURE:
<223> OTHER INFORMATION: Encoded polypeptide of a synthetic construct based on BoNTE Hc

<400> SEQUENCE: 14

```
Met Gly Glu Ser Gln Gln Glu Leu Asn Ser Met Val Thr Asp Thr Leu
  1               5                  10                  15

Asn Asn Ser Ile Pro Phe Lys Leu Ser Ser Tyr Thr Asp Asp Lys Ile
             20                  25                  30

Leu Ile Ser Tyr Phe Asn Lys Phe Phe Lys Arg Ile Lys Ser Ser Ser
         35                  40                  45

Val Leu Asn Met Arg Tyr Lys Asn Asp Lys Tyr Val Asp Thr Ser Gly
     50                  55                  60

Tyr Asp Ser Asn Ile Asn Ile Asn Gly Asp Val Tyr Lys Tyr Pro Thr
 65                  70                  75                  80

Asn Lys Asn Gln Phe Gly Ile Tyr Asn Asp Lys Leu Thr Glu Leu Asn
                 85                  90                  95

Ile Ser Gln Asn Asp Tyr Ile Ile Tyr Asp Asn Lys Tyr Lys Asn Phe
            100                 105                 110

Ser Ile Ser Phe Trp Val Arg Ile Pro Asn Tyr Asp Asn Lys Ile Val
        115                 120                 125
```

Asn Val Asn Asn Glu Tyr Thr Ile Ile Asn Cys Met Arg Asp Asn Asn
            130                 135                 140

Ser Gly Trp Lys Val Ser Leu Asn His Asn Glu Ile Ile Trp Thr Leu
145                 150                 155                 160

Gln Asp Asn Ala Gly Ile Asn Gln Lys Leu Ala Phe Asn Tyr Gly Asn
                165                 170                 175

Ala Asn Gly Ile Ser Asp Tyr Ile Asn Lys Trp Ile Phe Val Thr Ile
            180                 185                 190

Thr Asn Asp Arg Leu Gly Asp Ser Lys Leu Tyr Ile Asn Gly Asn Leu
        195                 200                 205

Ile Asp Gln Lys Ser Ile Leu Asn Leu Gly Asn Ile His Val Ser Asp
    210                 215                 220

Asn Ile Leu Phe Lys Ile Val Asn Cys Ser Tyr Thr Arg Tyr Ile Gly
225                 230                 235                 240

Ile Arg Tyr Phe Asn Ile Phe Asp Lys Glu Leu Asp Glu Thr Glu Ile
                245                 250                 255

Gln Thr Leu Tyr Ser Asn Glu Pro Asn Thr Asn Ile Leu Lys Asp Phe
            260                 265                 270

Trp Gly Asn Tyr Leu Leu Tyr Asp Lys Glu Tyr Tyr Leu Leu Asn Val
        275                 280                 285

Leu Lys Pro Asn Asn Phe Ile Asp Arg Arg Lys Asp Ser Thr Leu Ser
    290                 295                 300

Ile Asn Asn Ile Arg Ser Thr Ile Leu Leu Ala Asn Arg Leu Tyr Ser
305                 310                 315                 320

Gly Ile Lys Val Lys Ile Gln Arg Val Asn Asn Ser Ser Thr Asn Asp
                325                 330                 335

Asn Leu Val Arg Lys Asn Asp Gln Val Tyr Ile Asn Phe Val Ala Ser
            340                 345                 350

Lys Thr His Leu Phe Pro Leu Tyr Ala Asp Thr Ala Thr Thr Asn Lys
        355                 360                 365

Glu Lys Thr Ile Lys Ile Ser Ser Ser Gly Asn Arg Phe Asn Gln Val
    370                 375                 380

Val Val Met Asn Ser Val Gly Asn Asn Cys Thr Met Asn Phe Lys Asn
385                 390                 395                 400

Asn Asn Gly Asn Asn Ile Gly Leu Leu Gly Phe Lys Ala Asp Thr Val
                405                 410                 415

Val Ala Ser Thr Trp Tyr Tyr Thr His Met Arg Asp His Thr Asn Ser
            420                 425                 430

Asn Gly Cys Phe Trp Asn Phe Ile Ser Glu Glu His Gly Trp Gln Glu
        435                 440                 445

Lys

<210> SEQ ID NO 15
<211> LENGTH: 1317
<212> TYPE: DNA
<213> ORGANISM: Artificial Sequence
<220> FEATURE:
<223> OTHER INFORMATION: Synthetic construct based on BoNTF Hc

<400> SEQUENCE: 15
gaattcacga tgtcctacac caacgacaag atcctgatct tgtacttcaa caagctgtac    60
aagaagatca aggacaactc catcttggac atgagatacg aaaacaataa gttcatcgac   120
atctccggtt acggttccaa catctccatc aacggtgacg tctacatcta ctccaccaat   180

-continued

```
agaaaccagt tcggaatcta ctcctccaag ccttccgagg tcaacatcgc tcagaacaac      240
gacatcatct acaacggaag ataccagaac ttctccatct ccttctgggt ccgtatccca      300
aagtacttca acaaggtcaa cctgaataac gagtacacca tcatcgactg catccgtaac      360
aataactccg gatggaagat ctcccctgaac tacaacaaga tcatctggac cctgcaggac     420
accgccggta acaatcagaa gttggtcttc aactacaccc agatgatctc catctccgac      480
tacatcaaca agtggatctt cgtcaccatc accaataacc gtttgggaaa ctccagaatc      540
tacatcaacg gtaacttgat cgacgagaag tccatctcca acttgggtga catccacgtc      600
tccgacaaca ttttgttcaa gatcgtcggt tgtaacgaca cccgttacgt cgggatccgt      660
tacttcaaag tcttcgacac tgagttgggt aagaccgaga tcgagacctt gtactccgac      720
gagcctgacc catccatcct gaaggacttc tggggtaact acctgctgta caacaaacgt      780
tactacttgc tgaacttgtt gcgtaccgac aagtccatca cccagaactc caacttcttg      840
aacatcaacc agcagagagg tgtctaccag aagccaaaca tcttctccaa caccagattg      900
tacaccggag tcgaggtcat tatcagaaag aacggatcta ctgatatttc caacaccgat      960
aacttcgtca gaaagaacga tctggcttac atcaacgttg tcgacagaga tgtcgaatac     1020
cgtctgtacg ccgatatctc tatcgccaaa cctgaaaaga tcatcaagct gatccgtacc     1080
tctaactcta caactctct gggacaaat atcgtcatgg actccatcgg taataactgt       1140
accatgaact tccagaacaa caacggtgga acatcggtt tgttgggttt ccactccaac      1200
aacttggtcg cttcctcctg gtactacaac aacatccgta gaacacctc ctccaacggt      1260 tgcttctggt ccttcatctc caaggagcac ggttggcagg agaactaata ggaattc        1317
```

<210> SEQ ID NO 16
<211> LENGTH: 432
<212> TYPE: PRT
<213> ORGANISM: Artificial Sequence
<220> FEATURE:
<223> OTHER INFORMATION: Encoded polypeptide of a synthetic construct based on BoNTF Hc

<400> SEQUENCE: 16

```
Met Ser Tyr Thr Asn Asp Lys Ile Leu Ile Leu Tyr Phe Asn Lys Leu
 1               5                  10                  15

Tyr Lys Lys Ile Lys Asp Asn Ser Ile Leu Asp Met Arg Tyr Glu Asn
            20                  25                  30

Asn Lys Phe Ile Asp Ile Ser Gly Tyr Gly Ser Asn Ile Ser Ile Asn
        35                  40                  45

Gly Asp Val Tyr Ile Tyr Ser Thr Asn Arg Asn Gln Phe Gly Ile Tyr
    50                  55                  60

Ser Ser Lys Pro Ser Glu Val Asn Ile Ala Gln Asn Asn Asp Ile Ile
65                  70                  75                  80

Tyr Asn Gly Arg Tyr Gln Asn Phe Ser Ile Ser Phe Trp Val Arg Ile
                85                  90                  95

Pro Lys Tyr Phe Asn Lys Val Asn Leu Asn Asn Glu Tyr Thr Ile Ile
            100                 105                 110

Asp Cys Ile Arg Asn Asn Asn Ser Gly Trp Lys Ile Ser Leu Asn Tyr
        115                 120                 125

Asn Lys Ile Ile Trp Thr Leu Gln Asp Thr Ala Gly Asn Asn Gln Lys
    130                 135                 140

Leu Val Phe Asn Tyr Thr Gln Met Ile Ser Ile Ser Asp Tyr Ile Asn
145                 150                 155                 160
```

```
Lys Trp Ile Phe Val Thr Ile Thr Asn Asn Arg Leu Gly Asn Ser Arg
                165                 170                 175
Ile Tyr Ile Asn Gly Asn Leu Ile Asp Glu Lys Ser Ile Ser Asn Leu
            180                 185                 190
Gly Asp Ile His Val Ser Asp Asn Ile Leu Phe Lys Ile Val Gly Cys
        195                 200                 205
Asn Asp Thr Arg Tyr Val Gly Ile Arg Tyr Phe Lys Val Phe Asp Thr
    210                 215                 220
Glu Leu Gly Lys Thr Glu Ile Glu Thr Leu Tyr Ser Asp Glu Pro Asp
225                 230                 235                 240
Pro Ser Ile Leu Lys Asp Phe Trp Gly Asn Tyr Leu Leu Tyr Asn Lys
                245                 250                 255
Arg Tyr Tyr Leu Leu Asn Leu Leu Arg Thr Asp Lys Ser Ile Thr Gln
            260                 265                 270
Asn Ser Asn Phe Leu Asn Ile Asn Gln Gln Arg Gly Val Tyr Gln Lys
        275                 280                 285
Pro Asn Ile Phe Ser Asn Thr Arg Leu Tyr Thr Gly Val Glu Val Ile
    290                 295                 300
Ile Arg Lys Asn Gly Ser Thr Asp Ile Ser Asn Thr Asp Asn Phe Val
305                 310                 315                 320
Arg Lys Asn Asp Leu Ala Tyr Ile Asn Val Val Asp Arg Asp Val Glu
                325                 330                 335
Tyr Arg Leu Tyr Ala Asp Ile Ser Ile Ala Lys Pro Glu Lys Ile Ile
            340                 345                 350
Lys Leu Ile Arg Thr Ser Asn Ser Asn Asn Ser Leu Gly Gln Ile Ile
        355                 360                 365
Val Met Asp Ser Ile Gly Asn Asn Cys Thr Met Asn Phe Gln Asn Asn
    370                 375                 380
Asn Gly Gly Asn Ile Gly Leu Leu Gly Phe His Ser Asn Asn Leu Val
385                 390                 395                 400
Ala Ser Ser Trp Tyr Tyr Asn Asn Ile Arg Lys Asn Thr Ser Ser Asn
                405                 410                 415
Gly Cys Phe Trp Ser Phe Ile Ser Lys Glu His Gly Trp Gln Glu Asn
            420                 425                 430

<210> SEQ ID NO 17
<211> LENGTH: 1368
<212> TYPE: DNA
<213> ORGANISM: Artificial Sequence
<220> FEATURE:
<223> OTHER INFORMATION: Synthetic construct based on BoNTG Hc

<400> SEQUENCE: 17
gaattcacga tgaaggacac catcctgatc caggtcttca caactacat ctccaacatc      60 tcctccaacg ccatcctgtc cctgtcctac cgtggtggtc gtctgatcga ctcctccggt     120
tacggagcca ccatgaacgt cggttccgac gtcatcttca cgacatcgg taacggtcag     180 ttcaagctga caactccga gaactccaac atcaccgccc accagtccaa gttcgtcgtc     240
tacgactcca tgttcgacaa cttctccatc aacttctggg tccgtacccc aaagtacaac     300
aacaacgaca tccagaccta cctgcagaac gagtacacca tcatctcctg tatcaagaac     360
gactccggtt ggaaggtctc catcaaggga accgtatca tctggaccct gatcgacgtc     420
aacgccaagt ccagtccat cttcttcgag tactccatca aggacaacat ctccgactac     480
atcaacaagt ggttctccat caccatcacc aacgaccgtc tgggtaacgc caacatctac     540
```

-continued

```
atcaacggtt ccctgaagaa gtccgagaag atcctgaacc tggaccgtat caactcctcc    600
aacgacatcg acttcaagct gatcaactgt accgacacca ccaagttcgt ctggatcaag    660
gacttcaaca tcttcggtcg tgagctgaac gccaccgagg tctcctccct gtactggatc    720
cagtcctcca ccaacaccct gaaggacttc tggggaaacc cactgcgtta cgacacccag    780
tactacctgt tcaaccaggg tatgcagaac atctacatca agtacttctc caaggcctcc    840
atgggtgaga ccgcccctcg taccaacttc aacaacgccg ccatcaacta ccagaacctg    900
tacctgggtc tgcgtttcat catcaagaag gcctccaact cccgtaacat caacaacgac    960
aacatcgtcc gtgagggtga ctacatctac ctgaacatcg acaacatctc cgacgagtcc    1020
taccgtgtct acgtcctggt caactccaag gagatccaga cccagctgtt cctggcccca    1080
atcaacgacg accctacctt ctacgacgtc ctgcagatca agaagtacta cgagaagacc    1140
acctacaact gtcagatcct gtgcgagaag gacaccaaga ccttcggact gttcggtatc    1200
ggtaagttcg tcaaggacta cggttacgtc tgggacacct acgacaacta cttctgtatc    1260
tcccagtggt acctgcgtcg tatctccgag aacatcaaca agctgcgtct gggatgtaac    1320
tggcagttca tcccagtcga cgagggttgg accgagtaat aggaattc    1368
```

<210> SEQ ID NO 18
<211> LENGTH: 449
<212> TYPE: PRT
<213> ORGANISM: Artificial Sequence
<220> FEATURE:
<223> OTHER INFORMATION: Encoded polypeptide of a synthetic construct based on BoNTG Hc

<400> SEQUENCE: 18

```
Met Lys Asp Thr Ile Leu Ile Gln Val Phe Asn Asn Tyr Ile Ser Asn
  1               5                  10                  15

Ile Ser Ser Asn Ala Ile Leu Ser Leu Ser Tyr Arg Gly Gly Arg Leu
             20                  25                  30

Ile Asp Ser Ser Gly Tyr Gly Ala Thr Met Asn Val Gly Ser Asp Val
         35                  40                  45

Ile Phe Asn Asp Ile Gly Asn Gly Gln Phe Lys Leu Asn Asn Ser Glu
     50                  55                  60

Asn Ser Asn Ile Thr Ala His Gln Ser Lys Phe Val Val Tyr Asp Ser
 65                  70                  75                  80

Met Phe Asp Asn Phe Ser Ile Asn Phe Trp Val Arg Thr Pro Lys Tyr
                 85                  90                  95

Asn Asn Asn Asp Ile Gln Thr Tyr Leu Gln Asn Glu Tyr Thr Ile Ile
            100                 105                 110

Ser Cys Ile Lys Asn Asp Ser Gly Trp Lys Val Ser Ile Lys Gly Asn
        115                 120                 125

Arg Ile Ile Trp Thr Leu Ile Asp Val Asn Ala Lys Ser Lys Ser Ile
    130                 135                 140

Phe Phe Glu Tyr Ser Ile Lys Asp Asn Ile Ser Asp Tyr Ile Asn Lys
145                 150                 155                 160

Trp Phe Ser Ile Thr Ile Thr Asn Asp Arg Leu Gly Asn Ala Asn Ile
                165                 170                 175

Tyr Ile Asn Gly Ser Leu Lys Lys Ser Glu Lys Ile Leu Asn Leu Asp
            180                 185                 190

Arg Ile Asn Ser Ser Asn Asp Ile Asp Phe Lys Leu Ile Asn Cys Thr
        195                 200                 205

Asp Thr Thr Lys Phe Val Trp Ile Lys Asp Phe Asn Ile Phe Gly Arg
```

```
            210                 215                 220
Glu Leu Asn Ala Thr Glu Val Ser Ser Leu Tyr Trp Ile Gln Ser Ser
225                 230                 235                 240

Thr Asn Thr Leu Lys Asp Phe Trp Gly Asn Pro Leu Arg Tyr Asp Thr
                245                 250                 255

Gln Tyr Tyr Leu Phe Asn Gln Gly Met Gln Asn Ile Tyr Ile Lys Tyr
            260                 265                 270

Phe Ser Lys Ala Ser Met Gly Glu Thr Ala Pro Arg Thr Asn Phe Asn
            275                 280                 285

Asn Ala Ala Ile Asn Tyr Gln Asn Leu Tyr Leu Gly Leu Arg Phe Ile
            290                 295                 300

Ile Lys Lys Ala Ser Asn Ser Arg Asn Ile Asn Asn Asp Asn Ile Val
305                 310                 315                 320

Arg Glu Gly Asp Tyr Ile Tyr Leu Asn Ile Asp Asn Ile Ser Asp Glu
                325                 330                 335

Ser Tyr Arg Val Tyr Val Leu Val Asn Ser Lys Glu Ile Gln Thr Gln
                340                 345                 350

Leu Phe Leu Ala Pro Ile Asn Asp Asp Pro Thr Phe Tyr Asp Val Leu
            355                 360                 365

Gln Ile Lys Lys Tyr Tyr Glu Lys Thr Thr Tyr Asn Cys Gln Ile Leu
            370                 375                 380

Cys Glu Lys Asp Thr Lys Thr Phe Gly Leu Phe Gly Ile Gly Lys Phe
385                 390                 395                 400

Val Lys Asp Tyr Gly Tyr Val Trp Asp Thr Tyr Asp Asn Tyr Phe Cys
                405                 410                 415

Ile Ser Gln Trp Tyr Leu Arg Arg Ile Ser Glu Asn Ile Asn Lys Leu
                420                 425                 430

Arg Leu Gly Cys Asn Trp Gln Phe Ile Pro Val Asp Glu Gly Trp Thr
            435                 440                 445

Glu

<210> SEQ ID NO 19
<211> LENGTH: 1242
<212> TYPE: DNA
<213> ORGANISM: Artificial Sequence
<220> FEATURE:
<223> OTHER INFORMATION: Synthetic construct based on BoNTA Hn

<400> SEQUENCE: 19
atggctctga cgacctgtg catcaaagtt aacaactggg acctgttctt ctccccgtct     60
gaagacaact tcactaacga cctgaacaaa ggcgaagaaa tcacctccga cactaacatc    120
gaagctgcta agaaaacat ctctctggac ctgatccagc agtactacct gactttcaac    180
ttcgacaacg aaccggaaaa catctccatc gaaaacctgt cttccgacat catcggtcag    240
ctggaactga tgccgaacat cgaacgcttc ccgaacggca gaaatacga actggacaaa    300 tacaccatgt ccactaccct gcgtgctcag gaattcgaac acggtaaatc tcgtatcgct    360
ctgactaact ccgttaacga agctctgctg aacccgtctc gcgtttacac cttcttctct    420
tccgactacg ttaagaaagt taacaaagct actgaagctg ctatgttcct gggttgggtt    480
gaacagctgg tttacgactt caccgacgaa acttctgaag tttccaccac tgacaaaatc    540
gctgacatca ctatcatcat cccgtacatc ggcccggctc tgaacatcgg taacatgctg    600
tacaaagacg acttcgttgg tgctctgatc ttctctggcg ctgttatcct gctggaattc    660
atcccggaaa tcgctatccc ggttctgggt accttcgctc tggtttccta tcgctaac     720
```

-continued

```
aaagttctga ctgttcagac catcgacaac gctctgtcta aacgtaacga aaaatgggac    780
gaagtttaca atacatcgt tactaactgg ctggctaaag ttaacactca gatcgacctg    840
atccgtaaga agatgaaaga agctctggaa accaggctg aagctactaa agctatcatc    900
aactaccagt acaaccagta caccgaagaa gaaaagaaca acatcaactt caacatcgat    960
gacctgtcct ctaaactgaa cgaatccatc aacaaagcta tgatcaacat caacaaattc   1020
ctgaaccagt gctctgtttc ctacctgatg aactctatga tcccgtacgg cgttaaacgc   1080
ctggaagact cgacgcttc cctgaaagac gctctgctga aatacatccg tgacaactac   1140
ggtactctga tcggccaggt tgaccgtctg aaagacaagg ttaacaacac cctgtctact   1200
gacatcccgt ccagctgtc caaatacgtt gacaaccagt aa                      1242
```

<210> SEQ ID NO 20
<211> LENGTH: 413
<212> TYPE: PRT
<213> ORGANISM: Artificial Sequence
<220> FEATURE:
<223> OTHER INFORMATION: Encoded polypeptide of a synthetic construct based on BoNTA Hn

<400> SEQUENCE: 20

```
Met Ala Leu Asn Asp Leu Cys Ile Lys Val Asn Asn Trp Asp Leu Phe
  1               5                  10                  15

Phe Ser Pro Ser Glu Asp Asn Phe Thr Asn Asp Leu Asn Lys Gly Glu
             20                  25                  30

Glu Ile Thr Ser Asp Thr Asn Ile Glu Ala Ala Glu Glu Asn Ile Ser
         35                  40                  45

Leu Asp Leu Ile Gln Gln Tyr Tyr Leu Thr Phe Asn Phe Asp Asn Glu
     50                  55                  60

Pro Glu Asn Ile Ser Ile Glu Asn Leu Ser Ser Asp Ile Ile Gly Gln
 65                  70                  75                  80

Leu Glu Leu Met Pro Asn Ile Glu Arg Phe Pro Asn Gly Lys Lys Tyr
                 85                  90                  95

Glu Leu Asp Lys Tyr Thr Met Phe His Tyr Leu Arg Ala Gln Glu Phe
            100                 105                 110

Glu His Gly Lys Ser Arg Ile Ala Leu Thr Asn Ser Val Asn Glu Ala
        115                 120                 125

Leu Leu Asn Pro Ser Arg Val Tyr Thr Phe Phe Ser Ser Asp Tyr Val
    130                 135                 140

Lys Lys Val Asn Lys Ala Thr Glu Ala Ala Met Phe Leu Gly Trp Val
145                 150                 155                 160

Glu Gln Leu Val Tyr Asp Phe Thr Asp Glu Thr Ser Glu Val Ser Thr
                165                 170                 175

Thr Asp Lys Ile Ala Asp Ile Thr Ile Ile Pro Tyr Ile Gly Pro
            180                 185                 190

Ala Leu Asn Ile Gly Asn Met Leu Tyr Lys Asp Asp Phe Val Gly Ala
        195                 200                 205

Leu Ile Phe Ser Gly Ala Val Ile Leu Leu Glu Phe Ile Pro Glu Ile
    210                 215                 220

Ala Ile Pro Val Leu Gly Thr Phe Ala Leu Val Ser Tyr Ile Ala Asn
225                 230                 235                 240

Lys Val Leu Thr Val Gln Thr Ile Asp Asn Ala Leu Ser Lys Arg Asn
                245                 250                 255

Glu Lys Trp Asp Glu Val Tyr Lys Tyr Ile Val Thr Asn Trp Leu Ala
```

-continued

```
                     260                 265                 270
Lys Val Asn Thr Gln Ile Asp Leu Ile Arg Lys Met Lys Glu Ala
                275                 280                 285
Leu Glu Asn Gln Ala Glu Ala Thr Lys Ala Ile Ile Asn Tyr Gln Tyr
            290                 295                 300
Asn Gln Tyr Thr Glu Glu Lys Asn Asn Ile Asn Phe Asn Ile Asp
305                 310                 315                 320
Asp Leu Ser Ser Lys Leu Asn Glu Ser Ile Asn Lys Ala Met Ile Asn
                325                 330                 335
Ile Asn Lys Phe Leu Asn Gln Cys Ser Val Ser Tyr Leu Met Asn Ser
            340                 345                 350
Met Ile Pro Tyr Gly Val Lys Arg Leu Glu Asp Phe Asp Ala Ser Leu
                355                 360                 365
Lys Asp Ala Leu Leu Lys Tyr Ile Arg Asp Asn Tyr Gly Thr Leu Ile
            370                 375                 380
Gly Gln Val Asp Arg Leu Lys Asp Lys Val Asn Asn Thr Leu Ser Thr
385                 390                 395                 400
Asp Ile Pro Phe Gln Leu Ser Lys Tyr Val Asp Asn Gln
                405                 410
```

<210> SEQ ID NO 21
<211> LENGTH: 1242
<212> TYPE: DNA
<213> ORGANISM: Artificial Sequence
<220> FEATURE:
<223> OTHER INFORMATION: Synthetic construct based on BoNTB Hn

<400> SEQUENCE: 21

| | | |
|---|---|---|
| atggctccag gaatctgtat cgacgtcgac aacgaggact tgttcttcat cgctgacaag | 60 |
| aactccttct ccgacgactt gtccaagaac gagagaatcg agtacaacac ccagtccaac | 120 |
| tacatcgaga cgacttccc aatcaacgag ttgatcttgg acaccgactt gatctccaag | 180 |
| atcgagttgc atccgagaa caccgagtcc ttgactgact caacgtcga cgtcccagtc | 240 |
| tacgagaagc aaccagctat caagaagatt ttcaccgacg agaacaccat cttccaatac | 300 |
| ctgtactctc agaccttccc tttggacatc agagacatct ccttgacctc ttccttcgac | 360 |
| gacgccctgc tgttctccaa caaggtctac tccttcttct ccatggacta catcaagact | 420 |
| gctaacaagg tcgtcgaggc cggtttgttc gctggttggg tcaagcagat cgtcaacgat | 480 |
| ttcgtcatcg aggctaacaa gtccaacacc atggacaaga ttgccgacat ctccttgatt | 540 |
| gtcccataca tcggtttggc cttgaacgtc ggtaacgaga ccgccaaggg taacttcgag | 600 |
| aacgctttcg agatcgctgg tgcctccatc ttgttggagt tcatcccaga gttgttgatc | 660 |
| ccagtcgtcg gtgccttctt gttggagtcc tacatcgaca caagaacaa gatcatcaag | 720 |
| accatcgaca cgctttgac caagagaaac gagaagtggt ccgacatgta cggtttgatc | 780 |
| gtcgcccaat ggttgtccac cgtcaacacc caattctaca ccatcaagga gggtatgtac | 840 |
| aaggccttga actaccaggc ccaagctttg gaggagatca tcaagtacag atacaacatc | 900 |
| tactccgaga aggagaagtc caacattaac atcgacttca cgacatcaa ctccaagctg | 960 |
| aacgagggta ttaaccaggc catcgacaac atcaacaact catcaacgg ttgttccgtc | 1020 |
| tcctacttga tgaagaagat gattccattg gccgtcgaga agttgttgga cttcgacaac | 1080 |
| accctgaaga gaacttgtt gaactacatc gacgagaaca gttgtactt gatcggttcc | 1140 |
| gctgagtacg agaagtccaa ggtcaacaag tacttgaaga ccatcatgcc attcgacttg | 1200 | tccatctaca ccaacgacac catcttgatc gagatgttct aa        1242

<210> SEQ ID NO 22
<211> LENGTH: 413
<212> TYPE: PRT
<213> ORGANISM: Artificial Sequence
<220> FEATURE:
<223> OTHER INFORMATION: Encoded polypeptide of a synthetic construct based on BoNTB Hn

<400> SEQUENCE: 22

```
Met Ala Pro Gly Ile Cys Ile Asp Val Asp Asn Glu Asp Leu Phe Phe
  1               5                  10                  15

Ile Ala Asp Lys Asn Ser Phe Ser Asp Leu Ser Lys Asn Glu Arg
             20                  25                  30

Ile Glu Tyr Asn Thr Gln Ser Asn Tyr Ile Glu Asn Asp Phe Pro Ile
         35                  40                  45

Asn Glu Leu Ile Leu Asp Thr Asp Leu Ile Ser Lys Ile Glu Leu Pro
 50                  55                  60

Ser Glu Asn Thr Glu Ser Leu Thr Asp Phe Asn Val Asp Val Pro Val
 65                  70                  75                  80

Tyr Glu Lys Gln Pro Ala Ile Lys Lys Ile Phe Thr Asp Glu Asn Thr
                 85                  90                  95

Ile Phe Gln Tyr Leu Tyr Ser Gln Thr Phe Pro Leu Asp Ile Arg Asp
            100                 105                 110

Ile Ser Leu Thr Ser Ser Phe Asp Asp Ala Leu Leu Phe Ser Asn Lys
        115                 120                 125

Val Tyr Ser Phe Phe Ser Met Asp Tyr Ile Lys Thr Ala Asn Lys Val
130                 135                 140

Val Glu Ala Gly Leu Phe Ala Gly Trp Val Lys Gln Ile Val Asn Asp
145                 150                 155                 160

Phe Val Ile Glu Ala Asn Lys Ser Asn Thr Met Asp Lys Ile Ala Asp
                165                 170                 175

Ile Ser Leu Ile Val Pro Tyr Ile Gly Leu Ala Leu Asn Val Gly Asn
            180                 185                 190

Glu Thr Ala Lys Gly Asn Phe Glu Asn Ala Phe Glu Ile Ala Gly Ala
        195                 200                 205

Ser Ile Leu Leu Glu Phe Ile Pro Glu Leu Leu Ile Pro Val Val Gly
    210                 215                 220

Ala Phe Leu Leu Glu Ser Tyr Ile Asp Asn Lys Asn Lys Ile Ile Lys
225                 230                 235                 240

Thr Ile Asp Asn Ala Leu Thr Lys Arg Asn Glu Lys Trp Ser Asp Met
                245                 250                 255

Tyr Gly Leu Ile Val Ala Gln Trp Leu Ser Thr Val Asn Thr Gln Phe
            260                 265                 270

Tyr Thr Ile Lys Glu Gly Met Tyr Lys Ala Leu Asn Tyr Gln Ala Gln
        275                 280                 285

Ala Leu Glu Glu Ile Ile Lys Tyr Arg Tyr Asn Ile Tyr Ser Glu Lys
    290                 295                 300

Glu Lys Ser Asn Ile Asn Ile Asp Phe Asn Asp Ile Asn Ser Lys Leu
305                 310                 315                 320

Asn Glu Gly Ile Asn Gln Ala Ile Asp Asn Ile Asn Asn Phe Ile Asn
                325                 330                 335

Gly Cys Ser Val Ser Tyr Leu Met Lys Lys Met Ile Pro Leu Ala Val
            340                 345                 350
```

```
Glu Lys Leu Leu Asp Phe Asp Asn Thr Leu Lys Lys Asn Leu Leu Asn
            355                 360                 365

Tyr Ile Asp Glu Asn Lys Leu Tyr Leu Ile Gly Ser Ala Glu Tyr Glu
        370                 375                 380

Lys Ser Lys Val Asn Lys Tyr Leu Lys Thr Ile Met Pro Phe Asp Leu
385                 390                 395                 400

Ser Ile Tyr Thr Asn Asp Thr Ile Leu Ile Glu Met Phe
                405                 410
```

<210> SEQ ID NO 23
<211> LENGTH: 1200
<212> TYPE: DNA
<213> ORGANISM: Artificial Sequence
<220> FEATURE:
<223> OTHER INFORMATION: Synthetic construct based on BoNTC1 Hn

<400> SEQUENCE: 23

```
atgtccctgt acaacaagac ccttgactgt agagagctgc tggtgaagaa cactgacctg      60
ccattcatcg gtgacatcag tgacgtgaag actgacatct tcctgcgtaa ggacatcaac     120
gaggagactg aggtgatcta ctacccagac aacgtgtcag tagaccaagt gatcctcagt     180
aagaacacct ccgagcatgg acaactagac ctgctctacc ctagtatcga cagtgagagt     240
gagatcctgc caggggagaa tcaagtcttc tacgacaacc gtacccagaa cgtggactac     300
ctgaactcct actactacct agagtctcag aagctgagtg acaacgtgga ggacttcact     360
ttcacgcgtt caatcgagga ggctctggac aacagtgcaa aggtgtacac ttacttccct     420
accctggcta acaaggtgaa tgccggtgtg caaggtggtc tgttcctgat gtgggcaaac     480
gacgtggttg aggacttcac taccaacatc ctgcgtaagg acacactgga caagatctca     540
gatgtgtcag ctatcatccc ctacatcgga cccgcactga acatctccaa ctctgtgcgt     600
cgtggaaact tcactgaggc attcgcagtc actggtgtca ccatcctgct ggaggcattc     660
cctgagttca caatccctgc tctgggtgca ttcgtgatct acagtaaggt ccaggagcga     720
aacgagatca tcaagaccat cgacaactgt ctggagcaga ggatcaagag atggaaggac     780
tcctacgagt ggatgatggg aacgtggttg tccaggatca tcacccagtt caacaacatc     840
tcctaccaga tgtacgactc cctgaactac caggcaggtg caatcaaggc taagatcgac     900
ctggagtaca agaagtactc cggaagcgac aaggagaaca tcaagagcca ggttgagaac     960
ctgaagaaca gtctggacgt caagatctcg gaggcaatga caacatcaa caagttcatc    1020
cgagagtgct ccgtcaccta cctgttcaag aacatgctgc taaggtcat cgacgagctg    1080
aacgagttcg accgaaacac caaggcaaag ctgatcaacc tgatcgactc ccataacatc    1140
atcctggtcg gtgaggtcga caagctgaag gcaaaggtaa acaacagctt ccagaactaa    1200
```

<210> SEQ ID NO 24
<211> LENGTH: 399
<212> TYPE: PRT
<213> ORGANISM: Artificial Sequence
<220> FEATURE:
<223> OTHER INFORMATION: Encoded polypeptide of a synthetic construct
      based on BoNTC Hn

<400> SEQUENCE: 24

```
Met Ser Leu Tyr Asn Lys Thr Leu Asp Cys Arg Glu Leu Leu Val Lys
 1               5                  10                  15

Asn Thr Asp Leu Pro Phe Ile Gly Asp Ile Ser Asp Val Lys Thr Asp
            20                  25                  30
```

Ile Phe Leu Arg Lys Asp Ile Asn Glu Glu Thr Glu Val Ile Tyr Tyr
                35                  40                  45

Pro Asp Asn Val Ser Val Asp Gln Val Ile Leu Ser Lys Asn Thr Ser
     50                  55                  60

Glu His Gly Gln Leu Asp Leu Leu Tyr Pro Ser Ile Asp Ser Glu Ser
 65                  70                  75                  80

Glu Ile Leu Pro Gly Glu Asn Gln Val Phe Tyr Asp Asn Arg Thr Gln
                 85                  90                  95

Asn Val Asp Tyr Leu Asn Ser Tyr Tyr Tyr Leu Glu Ser Gln Lys Leu
                100                 105                 110

Ser Asp Asn Val Glu Asp Phe Thr Phe Thr Arg Ser Ile Glu Glu Ala
            115                 120                 125

Leu Asp Asn Ser Ala Lys Val Tyr Thr Tyr Phe Pro Thr Leu Ala Asn
            130                 135                 140

Lys Val Asn Ala Gly Val Gln Gly Gly Leu Phe Leu Met Trp Ala Asn
145                 150                 155                 160

Asp Val Val Glu Asp Phe Thr Thr Asn Ile Leu Arg Lys Asp Thr Leu
                165                 170                 175

Asp Lys Ile Ser Asp Val Ser Ala Ile Ile Pro Tyr Ile Gly Pro Ala
            180                 185                 190

Leu Asn Ile Ser Asn Ser Val Arg Arg Gly Asn Phe Thr Glu Ala Phe
            195                 200                 205

Ala Val Thr Gly Val Thr Ile Leu Leu Glu Ala Phe Pro Glu Phe Thr
            210                 215                 220

Ile Pro Ala Leu Gly Ala Phe Val Ile Tyr Ser Lys Val Gln Glu Arg
225                 230                 235                 240

Asn Glu Ile Ile Lys Thr Ile Asp Asn Cys Leu Glu Gln Arg Ile Lys
                245                 250                 255

Arg Trp Lys Asp Ser Tyr Glu Trp Met Met Gly Thr Trp Leu Ser Arg
            260                 265                 270

Ile Ile Thr Gln Phe Asn Asn Ile Ser Tyr Gln Met Tyr Asp Ser Leu
            275                 280                 285

Asn Tyr Gln Ala Gly Ala Ile Lys Ala Lys Ile Asp Leu Glu Tyr Lys
        290                 295                 300

Lys Tyr Ser Gly Ser Asp Lys Glu Asn Ile Lys Ser Gln Val Glu Asn
305                 310                 315                 320

Leu Lys Asn Ser Leu Asp Val Lys Ile Ser Glu Ala Met Asn Asn Ile
                325                 330                 335

Asn Lys Phe Ile Arg Glu Cys Ser Val Thr Tyr Leu Phe Lys Asn Met
            340                 345                 350

Leu Pro Lys Val Ile Asp Glu Leu Asn Glu Phe Asp Arg Asn Thr Lys
            355                 360                 365

Ala Lys Leu Ile Asn Leu Ile Asp Ser His Asn Ile Ile Leu Val Gly
            370                 375                 380

Glu Val Asp Lys Leu Lys Ala Lys Val Asn Asn Ser Phe Gln Asn
385                 390                 395

<210> SEQ ID NO 25
<211> LENGTH: 1161
<212> TYPE: DNA
<213> ORGANISM: Artificial Sequence
<220> FEATURE:
<223> OTHER INFORMATION: Synthetic construct based on BoNTD Hn

<400> SEQUENCE: 25

-continued

```
atggccaact cccgtgacga ctccacctgc atcaaggtca agaacaacag actgccatac      60
gttgccgaca aggactccat ctcccaggag atcttcgaga caagatcat caccgacgag      120 accaacgttc aaaactactc cgacaagttc tctttggacg agtccatcct ggacggtcag     180
gtcccaatca acccagagat cgtcgaccca ctgttgccaa cgtcaacat ggagccattg      240 aacttgccag gtgaggagat cgtcttctac gacgacatca ccaagtacgt cgactacttg     300
aactcctact actacttgga gtctcaaaag ttgtctaaca acgtcgagaa catcaccttg     360
accacctccg tcgaggaggc cttgggttac tctaacaaga tctacacctt cctgccatcc    420
ttggctgaga aggttaacaa gggtgttcaa gctggtttgt tcctgaactg ggccaacgag     480
gtcgtcgagg acttcaccac caacatcatg aagaaggaca ccctggacaa gatctccgac    540
gtctccgtca tcatcccata catcggtcca gccttgaaca tcggtaactc cgccctgaga    600
ggtaacttca accaggcctt cgccaccgcc ggtgtcgcct tcctgctgga gggtttccca    660
gagttcacca tcccagccct gggtgtcttc accttctact cctccatcca ggagagagag    720
aagatcatca gaccatcga gaactgcttg gagcagagag tcaagagatg aaggactcc     780 taccagtgga tggtttccaa ctggctgtcc agaatcacca cccaattcaa ccacatcaac     840
taccagatgt acgactccct gtcctaccag gccgacgcca tcaaggccaa gatcgacctg     900
gagtacaaga gtactccgg ttccgacaag gagaacatca gtcccaggt cgagaacctg     960 aagaactcct ggacgtcaa gatctccgag gccatgaaca acatcaacaa gttcatccgt    1020
gagtgttccg tcacctacct gttcaagaac atgctgccaa aggtcatcga cgagctgaac    1080
aagttcgacc tgagaaccaa gaccgagctg atcaacctga tcgactccca caacatcatc    1140
ctggttggtg aggttgacta a                                              1161
```

<210> SEQ ID NO 26
<211> LENGTH: 386
<212> TYPE: PRT
<213> ORGANISM: Artificial Sequence
<220> FEATURE:
<223> OTHER INFORMATION: Encoded polypeptide of a synthetic construct
      based on BoNTD Hn

<400> SEQUENCE: 26

```
Met Ala Asn Ser Arg Asp Asp Ser Thr Cys Ile Lys Val Lys Asn Asn
 1               5                  10                  15

Arg Leu Pro Tyr Val Ala Asp Lys Asp Ser Ile Ser Gln Glu Ile Phe
            20                  25                  30

Glu Asn Lys Ile Ile Thr Asp Glu Thr Asn Val Gln Asn Tyr Ser Asp
        35                  40                  45

Lys Phe Ser Leu Asp Glu Ser Ile Leu Asp Gly Gln Val Pro Ile Asn
    50                  55                  60

Pro Glu Ile Val Asp Pro Leu Leu Pro Asn Val Asn Met Glu Pro Leu
65                  70                  75                  80

Asn Leu Pro Gly Glu Glu Ile Val Phe Tyr Asp Asp Ile Thr Lys Tyr
                85                  90                  95

Val Asp Tyr Leu Asn Ser Tyr Tyr Tyr Leu Glu Ser Gln Lys Leu Ser
            100                 105                 110

Asn Asn Val Glu Asn Ile Thr Leu Thr Thr Ser Val Glu Glu Ala Leu
        115                 120                 125

Gly Tyr Ser Asn Lys Ile Tyr Thr Phe Leu Pro Ser Leu Ala Glu Lys
    130                 135                 140

Val Asn Lys Gly Val Gln Ala Gly Leu Phe Leu Asn Trp Ala Asn Glu
```

```
                145                 150                 155                 160
Val Val Glu Asp Phe Thr Thr Asn Ile Met Lys Lys Asp Thr Leu Asp
                    165                 170                 175

Lys Ile Ser Asp Val Ser Val Ile Ile Pro Tyr Ile Gly Pro Ala Leu
                180                 185                 190

Asn Ile Gly Asn Ser Ala Leu Arg Gly Asn Phe Asn Gln Ala Phe Ala
            195                 200                 205

Thr Ala Gly Val Ala Phe Leu Leu Glu Gly Phe Pro Glu Phe Thr Ile
        210                 215                 220

Pro Ala Leu Gly Val Phe Thr Phe Tyr Ser Ser Ile Gln Glu Arg Glu
225                 230                 235                 240

Lys Ile Ile Lys Thr Ile Glu Asn Cys Leu Glu Gln Arg Val Lys Arg
                245                 250                 255

Trp Lys Asp Ser Tyr Gln Trp Met Val Ser Asn Trp Leu Ser Arg Ile
                260                 265                 270

Thr Thr Gln Phe Asn His Ile Asn Tyr Gln Met Tyr Asp Ser Leu Ser
                275                 280                 285

Tyr Gln Ala Asp Ala Ile Lys Ala Lys Ile Asp Leu Glu Tyr Lys Lys
            290                 295                 300

Tyr Ser Gly Ser Asp Lys Glu Asn Ile Lys Ser Gln Val Glu Asn Leu
305                 310                 315                 320

Lys Asn Ser Leu Asp Val Lys Ile Ser Glu Ala Met Asn Asn Ile Asn
                325                 330                 335

Lys Phe Ile Arg Glu Cys Ser Val Thr Tyr Leu Phe Lys Asn Met Leu
                340                 345                 350

Pro Lys Val Ile Asp Glu Leu Asn Lys Phe Asp Leu Arg Thr Lys Thr
            355                 360                 365

Glu Leu Ile Asn Leu Ile Asp Ser His Asn Ile Ile Leu Val Gly Glu
        370                 375                 380

Val Asp
385

<210> SEQ ID NO 27
<211> LENGTH: 1149
<212> TYPE: DNA
<213> ORGANISM: Artificial Sequence
<220> FEATURE:
<223> OTHER INFORMATION: Synthetic construct based on BoNTE Hn

<400> SEQUENCE: 27
atgtccatct gcatcgagat caacaacggt gagctgttct tcgtggcttc cgagaacagt      60
tacaacgatg acaacatcaa cactcctaag gagattgacg acaccgtcac ttctaacaac     120
aactacgaaa acgacctgga ccaggtcatc ctaaacttca actccgagtc cgcccctggt     180
ctgtccgacg agaagctgaa cctgaccatc cagaacgacg cttacatccc aaagtacgac     240
tccaacggta catccgatat cgagcagcat gacgttaacg agcttaacgt cttcttctac     300
ttagacgctc agaaggtgcc cgagggtgag aacaacgtca atctcacctc ttcaattgac     360
acagccttgt tggagcagcc taagatctac accttcttct cctccgagtt catcaacaac     420
gtcaacaagc tgtgcaggc cgcattgttc gtaagctgga ttcagcaggt gttagtagac     480
ttcactactg aggctaacca gaagtccact gttgacaaga tcgctgacat ctccatcgtc     540
gtcccataca tcggtctggc tctgaacatc ggcaacgagg cacagaaggg caacttcaag     600
gatgcccttg agttgttggg tgccggtatt ttgttggagt cgaacccgga gctgctgatc     660
```

-continued

```
cctaccatcc tggtcttcac gatcaagtcc ttcctgggtt cctccgacaa caagaacaag    720
gtcattaagg ccatcaacaa cgccctgaag gagcgtgacg agaagtggaa ggaagtctat    780
tccttcatcg tctcgaactg gatgaccaag atcaacaccc agttcaacaa gcgaaaggag    840
cagatgtacc aggctctgca gaaccaggtc aacgccatca agaccatcat cgagtccaag    900
tacaactcct acaccctgga ggagaagaac gagcttacca acaagtacga tatcaagcag    960
atcgagaacg agctgaacca gaaggtctcc atcgccatga caacatcga caggttcctg   1020 accgagtcct ccatctccta cctgatgaag ctcatcaacg aggtcaagat caacaagctg   1080
cgagagtacg acgagaatgt caagacgtac ctgctgaact acatcatcca gcacggatcc   1140
atcctgtaa                                                           1149
```

```
<210> SEQ ID NO 28
<211> LENGTH: 382
<212> TYPE: PRT
<213> ORGANISM: Artificial Sequence
<220> FEATURE:
<223> OTHER INFORMATION: Encoded polypeptide of a synthetic construct
      based on BoNTE Hn

<400> SEQUENCE: 28
```

Met Ser Ile Cys Ile Glu Ile Asn Asn Gly Glu Leu Phe Phe Val Ala
1               5                   10                  15

Ser Glu Asn Ser Tyr Asn Asp Asp Ile Asn Thr Pro Lys Glu Ile
            20                  25                  30

Asp Asp Thr Val Thr Ser Asn Asn Asn Tyr Glu Asn Asp Leu Asp Gln
        35                  40                  45

Val Ile Leu Asn Phe Asn Ser Glu Ser Ala Pro Gly Leu Ser Asp Glu
    50                  55                  60

Lys Leu Asn Leu Thr Ile Gln Asn Asp Ala Tyr Ile Pro Lys Tyr Asp
65                  70                  75                  80

Ser Asn Gly Thr Ser Asp Ile Glu Gln His Asp Val Asn Glu Leu Asn
                85                  90                  95

Val Phe Phe Tyr Leu Asp Ala Gln Lys Val Pro Glu Gly Glu Asn Asn
            100                 105                 110

Val Asn Leu Thr Ser Ser Ile Asp Thr Ala Leu Leu Glu Gln Pro Lys
        115                 120                 125

Ile Tyr Thr Phe Phe Ser Ser Glu Phe Ile Asn Asn Val Asn Lys Pro
    130                 135                 140

Val Gln Ala Ala Leu Phe Val Ser Trp Ile Gln Gln Val Leu Val Asp
145                 150                 155                 160

Phe Thr Thr Glu Ala Asn Gln Lys Ser Thr Val Asp Lys Ile Ala Asp
                165                 170                 175

Ile Ser Ile Val Val Pro Tyr Ile Gly Leu Ala Leu Asn Ile Gly Asn
            180                 185                 190

Glu Ala Gln Lys Gly Asn Phe Lys Asp Ala Leu Glu Leu Leu Gly Ala
        195                 200                 205

Gly Ile Leu Leu Glu Phe Glu Pro Glu Leu Leu Ile Pro Thr Ile Leu
    210                 215                 220

Val Phe Thr Ile Lys Ser Phe Leu Gly Ser Ser Asp Asn Lys Asn Lys
225                 230                 235                 240

Val Ile Lys Ala Ile Asn Asn Ala Leu Lys Glu Arg Asp Glu Lys Trp
                245                 250                 255

Lys Glu Val Tyr Ser Phe Ile Val Ser Asn Trp Met Thr Lys Ile Asn
            260                 265                 270

```
Thr Gln Phe Asn Lys Arg Lys Glu Gln Met Tyr Gln Ala Leu Gln Asn
            275                 280                 285

Gln Val Asn Ala Ile Lys Thr Ile Ile Glu Ser Lys Tyr Asn Ser Tyr
        290                 295                 300

Thr Leu Glu Glu Lys Asn Glu Leu Thr Asn Lys Tyr Asp Ile Lys Gln
305                 310                 315                 320

Ile Glu Asn Glu Leu Asn Gln Lys Val Ser Ile Ala Met Asn Asn Ile
                325                 330                 335

Asp Arg Phe Leu Thr Glu Ser Ser Ile Ser Tyr Leu Met Lys Leu Ile
            340                 345                 350

Asn Glu Val Lys Ile Asn Lys Leu Arg Glu Tyr Asp Glu Asn Val Lys
        355                 360                 365

Thr Tyr Leu Leu Asn Tyr Ile Ile Gln His Gly Ser Ile Leu
370                 375                 380

<210> SEQ ID NO 29
<211> LENGTH: 1227
<212> TYPE: DNA
<213> ORGANISM: Artificial Sequence
<220> FEATURE:
<223> OTHER INFORMATION: Synthetic construct based on BoNTF Hn

<400> SEQUENCE: 29 atggcccccac cacgtctgtg tattagagtc aacaactcag aattattctt tgtcgcttcc     60
gagtcaagct acaacgagaa cgatattaac acacctaaag agattgacga tactaccaac    120
ctaaacaaca actaccggaa caacttggat gaggttattt tggattacaa ctcacagacc    180
atccctcaaa tttccaaccg taccttaaac actcttgtcc aagacaactc ctacgttcca    240
agatacgatt ctaacggtac tcagagatc gaggagtatg atgttgttga ctttaacgtc    300
tttttctatt tgcatgccca gaaggtgcca gaaggtgaaa ccaacatctc attgacttct    360
tccattgata ccgccttgtt ggaagagtcc aaggatatct tctttcttc ggagtttatc    420
gatactatca caagcctgt caacgccgct ctgttcattg attggattag caaggtcatc    480
agagatttta ccactgaagc tactcaaaag tccactgttg ataagattgc tgacatctct    540
ttgattgtcc cctatgtcgg tcttgctttg aacatcatta ttgaggcaga aaagggtaac    600
tttgaggagg cttttgaatt gttgggagtt ggtatttgt tggagtttgt tccagaactt    660
accattcctg tcattttagt ttttacgatc aagtcctaca tcgattcata cgagaacaag    720
aataaagcaa ttaaagctat taacaactcc ttgatcgaaa gagaggctaa gtggaaggaa    780
atctactcat ggattgtatc aaactggctt actagaatta acactcaatt taacaagaga    840
aaggagcaaa tgtaccaggc tctgcaaaac caagtcgatg ctatcaagac tgcaattgaa    900
tacaagtaca acaactatac ttccgatgag aagaacagac ttgaatctga atacaatatc    960
aacaacattg aagaagagtt gaacaagaaa gtttctttgg ctatgaagaa tatcgaaaga   1020
tttatgaccg aatcctctat ctcttacttg atgaagttga tcaatgaggc caaggttggt   1080
aagttgaaga agtacgataa ccacgttaag agcgatctgc tgaactacat tctcgaccac   1140
agatcaatcc tgggagagca gacaaacgag ctgagtgatt tggttacttc cactttgaac   1200
tcctccattc catttgagct ttcttaa                                        1227

<210> SEQ ID NO 30
<211> LENGTH: 408
<212> TYPE: PRT
<213> ORGANISM: Artificial Sequence
```

```
<220> FEATURE:
<223> OTHER INFORMATION: Encoded polypeptide of a synthetic construct
      based on BoNTF Hn

<400> SEQUENCE: 30

Met Ala Pro Pro Arg Leu Cys Ile Arg Val Asn Asn Ser Glu Leu Phe
 1               5                  10                  15

Phe Val Ala Ser Glu Ser Ser Tyr Asn Glu Asn Asp Ile Asn Thr Pro
             20                  25                  30

Lys Glu Ile Asp Asp Thr Thr Asn Leu Asn Asn Asn Tyr Arg Asn Asn
         35                  40                  45

Leu Asp Glu Val Ile Leu Asp Tyr Asn Ser Gln Thr Ile Pro Gln Ile
 50                  55                  60

Ser Asn Arg Thr Leu Asn Thr Leu Val Gln Asp Asn Ser Tyr Val Pro
 65                  70                  75                  80

Arg Tyr Asp Ser Asn Gly Thr Ser Glu Ile Glu Glu Tyr Asp Val Val
                 85                  90                  95

Asp Phe Asn Val Phe Phe Tyr Leu His Ala Gln Lys Val Pro Glu Gly
            100                 105                 110

Glu Thr Asn Ile Ser Leu Thr Ser Ser Ile Asp Thr Ala Leu Leu Glu
            115                 120                 125

Glu Ser Lys Asp Ile Phe Phe Ser Ser Glu Phe Ile Asp Thr Ile Asn
130                 135                 140

Lys Pro Val Asn Ala Ala Leu Phe Ile Asp Trp Ile Ser Lys Val Ile
145                 150                 155                 160

Arg Asp Phe Thr Thr Glu Ala Thr Gln Lys Ser Thr Val Asp Lys Ile
                165                 170                 175

Ala Asp Ile Ser Leu Ile Val Pro Tyr Val Gly Leu Ala Leu Asn Ile
            180                 185                 190

Ile Ile Glu Ala Glu Lys Gly Asn Phe Glu Glu Ala Phe Glu Leu Leu
            195                 200                 205

Gly Val Gly Ile Leu Leu Glu Phe Val Pro Glu Leu Thr Ile Pro Val
210                 215                 220

Ile Leu Val Phe Thr Ile Lys Ser Tyr Ile Asp Ser Tyr Glu Asn Lys
225                 230                 235                 240

Asn Lys Ala Ile Lys Ala Ile Asn Asn Ser Leu Ile Glu Arg Glu Ala
                245                 250                 255

Lys Trp Lys Glu Ile Tyr Ser Trp Ile Val Ser Asn Trp Leu Thr Arg
            260                 265                 270

Ile Asn Thr Gln Phe Asn Lys Arg Lys Glu Gln Met Tyr Gln Ala Leu
            275                 280                 285

Gln Asn Gln Val Asp Ala Ile Lys Thr Ala Ile Glu Tyr Lys Tyr Asn
290                 295                 300

Asn Tyr Thr Ser Asp Glu Lys Asn Arg Leu Glu Ser Glu Tyr Asn Ile
305                 310                 315                 320

Asn Asn Ile Glu Glu Glu Leu Asn Lys Lys Val Ser Leu Ala Met Lys
                325                 330                 335

Asn Ile Glu Arg Phe Met Thr Glu Ser Ser Ile Ser Tyr Leu Met Lys
            340                 345                 350

Leu Ile Asn Glu Ala Lys Val Gly Lys Leu Lys Lys Tyr Asp Asn His
            355                 360                 365

Val Lys Ser Asp Leu Leu Asn Tyr Ile Leu Asp His Arg Ser Ile Leu
370                 375                 380

Gly Glu Gln Thr Asn Glu Leu Ser Asp Leu Val Thr Ser Thr Leu Asn
```

```
385             390             395             400
Ser Ser Ile Pro Phe Glu Leu Ser
                405

<210> SEQ ID NO 31
<211> LENGTH: 1233
<212> TYPE: DNA
<213> ORGANISM: Artificial Sequence
<220> FEATURE:
<223> OTHER INFORMATION: Synthetic construct based on BoNTG Hn

<400> SEQUENCE: 31
atggccaaaa ataccggtaa atctgaacag tgtattattg ttaataatga ggatttattt      60
ttcatagcta ataagatag tttttcaaaa gatttagcta agcagaaaac tatagcatat     120
aatacacaaa ataatactat agaaaataat ttttctatag atcagttgat tttagataat     180
gatttaagca gtggcataga cttaccaaat gaaaacacag aaccatttac aaattttgac     240
gacatagata tccctgtgta tattaaacaa tctgctttaa aaaaaatttt tgtggatgga     300
gatagccttt ttgaatattt acatgctcaa acatttcctt ctaatataga aaatctacaa     360
ctaacgaatt cattaaatga tgctttaaga aataataata aagtctatac tttttttttct     420 acaaaccttg ttgaaaaagc taatacagtt gtaggtgctt cacttttttgt aaactgggta     480 aaaggagtaa tagatgattt tacatctgaa tccacacaaa aaagtactat agataaagtt     540
tcagatgtat ccataattat tccctatata ggacctgctt tgaatgtagg aaatgaaaca     600
gctaaagaaa attttaaaaa tgcttttgaa ataggtggag ccgctatctt aatggagttt     660
attccagaac ttattgtacc tatagttgga ttttttacat agaatcata tgtaggaaat     720 aaagggcata ttattatgac gatatccaat gctttaaaga aagggatca aaaatggaca     780 gatatgtatg gtttgatagt atcgcagtgg ctctcaacgg ttaatactca attttataca     840
ataaaagaaa gaatgtacaa tgctttaaat aatcaatcac aagcaataga aaaaataata     900
gaagatcaat ataatagata tagtgaagaa gataaaatga atattaacat tgattttaat     960
gatatagatt ttaaacttaa tcaaagtata aatttagcaa taaacaatat agatgatttt    1020
ataaaccaat gttctatatc atatctaatg aatagaatga ttccattagc tgtaaaaaag    1080
ttaaaagact ttgatgataa tcttaagaga gatttattgg agtatataga tacaaatgaa    1140
ctatatttac ttgatgaagt aaatattcta aaatcaaaag taaatagaca cctaaaagac    1200
agtataccat ttgatctttc actatatacc taa                                 1233

<210> SEQ ID NO 32
<211> LENGTH: 410
<212> TYPE: PRT
<213> ORGANISM: Artificial Sequence
<220> FEATURE:
<223> OTHER INFORMATION: Encoded polypeptide of a synthetic construct
      based on BoNTG Hn

<400> SEQUENCE: 32

Met Ala Lys Asn Thr Gly Lys Ser Glu Gln Cys Ile Ile Val Asn Asn
 1               5                  10                  15

Glu Asp Leu Phe Phe Ile Ala Asn Lys Asp Ser Phe Ser Lys Asp Leu
            20                  25                  30

Ala Lys Ala Glu Thr Ile Ala Tyr Asn Thr Gln Asn Asn Thr Ile Glu
        35                  40                  45

Asn Asn Phe Ser Ile Asp Gln Leu Ile Leu Asp Asn Asp Leu Ser Ser
    50                  55                  60
```

-continued

```
Gly Ile Asp Leu Pro Asn Glu Asn Thr Glu Pro Phe Thr Asn Phe Asp
65                  70                  75                  80

Asp Ile Asp Ile Pro Val Tyr Ile Lys Gln Ser Ala Leu Lys Lys Ile
                85                  90                  95

Phe Val Asp Gly Asp Ser Leu Phe Glu Tyr Leu His Ala Gln Thr Phe
            100                 105                 110

Pro Ser Asn Ile Glu Asn Leu Gln Leu Thr Asn Ser Leu Asn Asp Ala
        115                 120                 125

Leu Arg Asn Asn Asn Lys Val Tyr Thr Phe Phe Ser Thr Asn Leu Val
    130                 135                 140

Glu Lys Ala Asn Thr Val Val Gly Ala Ser Leu Phe Val Asn Trp Val
145                 150                 155                 160

Lys Gly Val Ile Asp Asp Phe Thr Ser Glu Ser Thr Gln Lys Ser Thr
                165                 170                 175

Ile Asp Lys Val Ser Asp Val Ser Ile Ile Ile Pro Tyr Ile Gly Pro
            180                 185                 190

Ala Leu Asn Val Gly Asn Glu Thr Ala Lys Glu Asn Phe Lys Asn Ala
        195                 200                 205

Phe Glu Ile Gly Gly Ala Ala Ile Leu Met Glu Phe Ile Pro Glu Leu
    210                 215                 220

Ile Val Pro Ile Val Gly Phe Phe Thr Leu Glu Ser Tyr Val Gly Asn
225                 230                 235                 240

Lys Gly His Ile Ile Met Thr Ile Ser Asn Ala Leu Lys Lys Arg Asp
                245                 250                 255

Gln Lys Trp Thr Asp Met Tyr Gly Leu Ile Val Ser Gln Trp Leu Ser
            260                 265                 270

Thr Val Asn Thr Gln Phe Tyr Thr Ile Lys Glu Arg Met Tyr Asn Ala
        275                 280                 285

Leu Asn Asn Gln Ser Gln Ala Ile Glu Lys Ile Ile Glu Asp Gln Tyr
    290                 295                 300

Asn Arg Tyr Ser Glu Glu Asp Lys Met Asn Ile Asn Ile Asp Phe Asn
305                 310                 315                 320

Asp Ile Asp Phe Lys Leu Asn Gln Ser Ile Asn Leu Ala Ile Asn Asn
                325                 330                 335

Ile Asp Asp Phe Ile Asn Gln Cys Ser Ile Ser Tyr Leu Met Asn Arg
            340                 345                 350

Met Ile Pro Leu Ala Val Lys Lys Leu Lys Asp Phe Asp Asp Asn Leu
        355                 360                 365

Lys Arg Asp Leu Leu Glu Tyr Ile Asp Thr Asn Glu Leu Tyr Leu Leu
    370                 375                 380

Asp Glu Val Asn Ile Leu Lys Ser Lys Val Asn Arg His Leu Lys Asp
385                 390                 395                 400

Ser Ile Pro Phe Asp Leu Ser Leu Tyr Thr
                405                 410
```

<210> SEQ ID NO 33
<211> LENGTH: 1314
<212> TYPE: DNA
<213> ORGANISM: Artificial Sequence
<220> FEATURE:
<223> OTHER INFORMATION: Synthetic construct based on BoNTF Hc

<400> SEQUENCE: 33

```
gaattcacga tgtcttacac taacgacaaa atcctgatcc tgtacttcaa caaactgtac     60
```

```
aaaaaaatca aagacaactc tatcctggac atgcgttacg aaaacaacaa attcatcgac    120
atctctggct atggttctaa catctctatc aacggtgacg tctacatcta ctctactaac    180
cgcaaccagt tcggtatcta ctcttctaaa ccgtctgaag taaacatcgc tcagaacaac    240
gacatcatct acaacggtcg ttaccagaac ttctctatct ctttctgggt tcgtatcccg    300
aaatacttca acaaagttaa cctgaacaac gaatacacta tcatcgactg catccgtaac    360
aacaactctg gttggaaaat ctctctgaac tacaacaaaa tcatctggac tctgcaggac    420
actgctggta caaccagaa actggttttc aactacactc agatgatctc tatctctgac    480
tacattaata aatggatctt cgttactatc actaacaacc gtctgggtaa ctctcgtatc    540
tacatcaacg gtaacctgat cgatgaaaaa tctatctcta acctgggtga catccacgtt    600
tctgacaaca tcctgttcaa aatcgttggt tgcaacgaca cgcgttacgt tggtatccgt    660
tacttcaaag ttttcgacac tgaactgggt aaaactgaaa tcgaaactct gtactctgac    720
gaaccggacc cgtctatcct gaaagacttc tggggtaact acctgctgta caacaaacgt    780
tactacctgc tgaacctgct ccggactgac aaatctatca ctcagaactc taacttcctg    840
aacatcaacc agcagcgtgg tgtttatcag aaacctaata tcttctctaa cactcgtctg    900
tacactggtg ttgaagttat catccgtaaa aacggttcta ctgacatctc taacactgac    960
aacttcgtac gtaaaaacga cctggcttac atcaacgttg ttgaccgtga cgttgaatac   1020
cgtctgtacg ctgacatctc tatcgctaaa ccggaaaaaa tcatcaaact gatccgtact   1080
tctaactcta caactctct gggtcagatc atcgttatgg actcgatcgg taacaactgc   1140
actatgaact tccagaacaa caacggtggt aacatcggtc tgctgggttt ccactctaac   1200
aacctggttg cttcttcatg gtactacaac aacatccgta aaacacttc ttctaacggt    1260 tgcttctggt ctttcatctc taaagaacac ggttggcagg aaaactaaga attc          1314
```

<210> SEQ ID NO 34
<211> LENGTH: 432
<212> TYPE: PRT
<213> ORGANISM: Artificial Sequence
<220> FEATURE:
<223> OTHER INFORMATION: Encoded polypeptide of a synthetic construct based on BoNTF Hc

<400> SEQUENCE: 34

```
Met Ser Tyr Thr Asn Asp Lys Ile Leu Ile Leu Tyr Phe Asn Lys Leu
 1               5                  10                  15

Tyr Lys Lys Ile Lys Asp Asn Ser Ile Leu Asp Met Arg Tyr Glu Asn
            20                  25                  30

Asn Lys Phe Ile Asp Ile Ser Gly Tyr Gly Ser Asn Ile Ser Ile Asn
        35                  40                  45

Gly Asp Val Tyr Ile Tyr Ser Thr Asn Arg Asn Gln Phe Gly Ile Tyr
    50                  55                  60

Ser Ser Lys Pro Ser Glu Val Asn Ile Ala Gln Asn Asn Asp Ile Ile
65                  70                  75                  80

Tyr Asn Gly Arg Tyr Gln Asn Phe Ser Ile Ser Phe Trp Val Arg Ile
                85                  90                  95

Pro Lys Tyr Phe Asn Lys Val Asn Leu Asn Asn Glu Tyr Thr Ile Ile
            100                 105                 110

Asp Cys Ile Arg Asn Asn Asn Ser Gly Trp Lys Ile Ser Leu Asn Tyr
        115                 120                 125

Asn Lys Ile Ile Trp Thr Leu Gln Asp Thr Ala Gly Asn Asn Gln Lys
    130                 135                 140
```

Leu Val Phe Asn Tyr Thr Gln Met Ile Ser Ile Ser Asp Tyr Ile Asn
145                 150                 155                 160

Lys Trp Ile Phe Val Thr Ile Thr Asn Asn Arg Leu Gly Asn Ser Arg
                165                 170                 175

Ile Tyr Ile Asn Gly Asn Leu Ile Asp Glu Lys Ser Ile Ser Asn Leu
            180                 185                 190

Gly Asp Ile His Val Ser Asp Asn Ile Leu Phe Lys Ile Val Gly Cys
            195                 200                 205

Asn Asp Thr Arg Tyr Val Gly Ile Arg Tyr Phe Lys Val Phe Asp Thr
        210                 215                 220

Glu Leu Gly Lys Thr Glu Ile Glu Thr Leu Tyr Ser Asp Glu Pro Asp
225                 230                 235                 240

Pro Ser Ile Leu Lys Asp Phe Trp Gly Asn Tyr Leu Leu Tyr Asn Lys
                245                 250                 255

Arg Tyr Tyr Leu Leu Asn Leu Leu Arg Thr Asp Lys Ser Ile Thr Gln
            260                 265                 270

Asn Ser Asn Phe Leu Asn Ile Asn Gln Gln Arg Gly Val Tyr Gln Lys
        275                 280                 285

Pro Asn Ile Phe Ser Asn Thr Arg Leu Tyr Thr Gly Val Glu Val Ile
290                 295                 300

Ile Arg Lys Asn Gly Ser Thr Asp Ile Ser Asn Thr Asp Asn Phe Val
305                 310                 315                 320

Arg Lys Asn Asp Leu Ala Tyr Ile Asn Val Val Asp Arg Asp Val Glu
                325                 330                 335

Tyr Arg Leu Tyr Ala Asp Ile Ser Ile Ala Lys Pro Glu Lys Ile Ile
            340                 345                 350

Lys Leu Ile Arg Thr Ser Asn Ser Asn Asn Ser Leu Gly Gln Ile Ile
        355                 360                 365

Val Met Asp Ser Ile Gly Asn Asn Cys Thr Met Asn Phe Gln Asn Asn
    370                 375                 380

Asn Gly Gly Asn Ile Gly Leu Leu Gly Phe His Ser Asn Asn Leu Val
385                 390                 395                 400

Ala Ser Ser Trp Tyr Tyr Asn Asn Ile Arg Lys Asn Thr Ser Ser Asn
                405                 410                 415

Gly Cys Phe Trp Ser Phe Ile Ser Lys Glu His Gly Trp Gln Glu Asn
            420                 425                 430

<210> SEQ ID NO 35
<211> LENGTH: 1278
<212> TYPE: DNA
<213> ORGANISM: Artificial Sequence
<220> FEATURE:
<223> OTHER INFORMATION: Synthetic construct based on BoNTE Hc

<400> SEQUENCE: 35
ttcgaaacga tgattttaat ttcctacttc aacaagttct tcaagagaat taagtcttct      60
tccgttttaa acatgagata caagaatgat aaatacgtcg acacttccgg ttacgactcc    120
aatatcaaca ttaacggtga cgtgtacaag tacccaacta caaaaaacca attcggtatc    180
tacaacgaca agcttactga gctgaacatc tctcaaaacg actacattat ctacgacaac    240
aagtacaata acttctctat ttctttctgg gtcagaattc ctaactacga taacaagatc    300
gtcaacgtta acaacgagta cactatcatc aactgtatga gagacaacaa ctccggttgg    360
aaggtctctc ttaaccacaa cgagatgatt tggaccttgc aagacaacgc aggtattaac    420

```
caaaagttag cattcaacta cggtaacgca aacggtattt ctgactacat caacaagtgg    480 atttcgtca ctatcactaa cgacagatta ggggactcta agctttacat taacggtaac    540
ttaatcgacc aaaagtccat tttaaactta ggtaacattc acgtttctga caacatctta    600
ttcaagatcg ttaactgcag ttacaacaga tacattggca ttagatactt caacattttc    660
gacaaggagt tagacgagac cgagattcaa actttataca gcaacgaacc taacaccaat    720 atttgaagg acttctgggg taactacttg ctttacgaca aggaatacta cttattaaac    780
gtgttaaagc caaacaactt cattgatagg agaaaggatt ctactttaag cattaacaac    840
atcagaagca ctattctttt agctaacaga ttatactctg gtatcaaggt taagatccaa    900
agagttaaca actcttctac taacgataac cttgttagaa agaacgatca ggtctatatt    960
aacttcgtcg ctagcaagac tcacttattc ccattatatg ctgataacgc taccaccaac    1020
aaggagaaga ccatcaagat ctcctcctct ggcaacagat taaccaagt cgtcgttatg    1080 aactccgtcg gtaacaactg taccatgaac tttaaaaata ataatggaaa taatattggg    1140
tgtttaggtt tcaaggcaga tactgtagtt gctagtactt ggtattatac ccacatgaga    1200
gatcacacca acagcaatgg atgttttttgg aactttatttt ctgaagaaca tggatggcaa    1260
gaaaaataat agggatcc                                                  1278
```

<210> SEQ ID NO 36
<211> LENGTH: 419
<212> TYPE: PRT
<213> ORGANISM: Artificial Sequence
<220> FEATURE:
<223> OTHER INFORMATION: Encoded polypeptide of a synthetic construct based on BoNTE Hc

<400> SEQUENCE: 36

```
Met Ile Leu Ile Ser Tyr Phe Asn Lys Phe Phe Lys Arg Ile Lys Ser
 1               5                  10                  15

Ser Ser Val Leu Asn Met Arg Tyr Lys Asn Asp Lys Tyr Val Asp Thr
            20                  25                  30

Ser Gly Tyr Asp Ser Asn Ile Asn Ile Asn Gly Asp Val Tyr Lys Tyr
        35                  40                  45

Pro Thr Asn Lys Asn Gln Phe Gly Ile Tyr Asn Asp Lys Leu Thr Glu
    50                  55                  60

Leu Asn Ile Ser Gln Asn Asp Tyr Ile Ile Tyr Asp Asn Lys Tyr Lys
65                  70                  75                  80

Asn Phe Ser Ile Ser Phe Trp Val Arg Ile Pro Asn Tyr Asp Asn Lys
                85                  90                  95

Ile Val Asn Val Asn Asn Glu Tyr Thr Ile Ile Asn Cys Met Arg Asp
            100                 105                 110

Asn Asn Ser Gly Trp Lys Val Ser Leu Asn His Asn Glu Ile Ile Trp
        115                 120                 125

Thr Leu Gln Asp Asn Ala Gly Ile Asn Gln Lys Leu Ala Phe Asn Tyr
    130                 135                 140

Gly Asn Ala Asn Gly Ile Ser Asp Tyr Ile Asn Lys Trp Ile Phe Val
145                 150                 155                 160

Thr Ile Thr Asn Asp Arg Leu Gly Asp Ser Lys Leu Tyr Ile Asn Gly
                165                 170                 175

Asn Leu Ile Asp Gln Lys Ser Ile Leu Asn Leu Gly Asn Ile His Val
            180                 185                 190

Ser Asp Asn Ile Leu Phe Lys Ile Val Asn Cys Ser Tyr Thr Arg Tyr
        195                 200                 205
```

```
Ile Gly Ile Arg Tyr Phe Asn Ile Phe Asp Lys Glu Leu Asp Glu Thr
    210                 215                 220
Glu Ile Gln Thr Leu Tyr Ser Asn Glu Pro Asn Thr Asn Ile Leu Lys
225                 230                 235                 240
Asp Phe Trp Gly Asn Tyr Leu Leu Tyr Asp Lys Glu Tyr Tyr Leu Leu
                245                 250                 255
Asn Val Leu Lys Pro Asn Asn Phe Ile Asp Arg Arg Lys Asp Ser Thr
                260                 265                 270
Leu Ser Ile Asn Asn Ile Arg Ser Thr Ile Leu Leu Ala Asn Arg Leu
            275                 280                 285
Tyr Ser Gly Ile Lys Val Lys Ile Gln Arg Val Asn Asn Ser Ser Thr
290                 295                 300
Asn Asp Asn Leu Val Arg Lys Asn Asp Gln Val Tyr Ile Asn Phe Val
305                 310                 315                 320
Ala Ser Lys Thr His Leu Phe Pro Leu Tyr Ala Asp Thr Ala Thr Thr
                325                 330                 335
Asn Lys Glu Lys Thr Ile Lys Ile Ser Ser Ser Gly Asn Arg Phe Asn
                340                 345                 350
Gln Val Val Val Met Asn Ser Val Gly Asn Asn Cys Thr Met Asn Phe
            355                 360                 365
Lys Asn Asn Asn Gly Asn Asn Ile Gly Leu Leu Gly Phe Lys Ala Asp
370                 375                 380
Thr Val Val Ala Ser Thr Trp Tyr Tyr Thr His Met Arg Asp His Thr
385                 390                 395                 400
Asn Ser Asn Gly Cys Phe Trp Asn Phe Ile Ser Glu Glu His Gly Trp
                405                 410                 415
Gln Glu Lys

<210> SEQ ID NO 37
<211> LENGTH: 1338
<212> TYPE: DNA
<213> ORGANISM: Artificial Sequence
<220> FEATURE:
<223> OTHER INFORMATION: Synthetic construct based on BoNTA Hc

<400> SEQUENCE: 37
ctcgagccat ggctcgtctg ctgtctacct tcactgaata catcaagaac atcatcaata      60
cctccatcct gaacctgcgc tacgaatcca atcacctgat cgacctgtct cgctacgctt     120
ccaaaatcaa catcggttct aaagttaact tcgatccgat cgacaagaat cagatccagc     180
tgttcaatct ggaatcttcc aaaatcgaag ttatcctgaa gaatgctatc gtatacaact     240
ctatgtacga aaacttctcc acctccttct ggatccgtat cccgaaatac ttcaactcca     300
tctctctgaa caatgaatac accatcatca actgcatgga aaacaattct ggttggaaag     360
tatctctgaa ctacggtgaa atcatctgga ctctgcagga cactcaggaa atcaaacagc     420
gtgttgtatt caaatactct cagatgatca acatctctga ctacatcaat cgctggatct     480
tcgttaccat caccaacaat cgtctgaata actccaaaat ctacatcaac ggccgtctga     540
tcgaccagaa accgatctcc aatctgggta catccacgc ttctaataac atcatgttca     600
aactggacgg ttgtcgtgac actcaccgct acatctggat caaatacttc aatctgttcg     660
acaaagaact gaacgaaaaa gaaatcaaag acctgtacga caaccagtcc aattctggta     720
tcctgaaaga cttctggggt gactacctgc agtacgacaa accgtactac atgctgaatc     780
tgtacgatcc gaacaaatac gttgacgtca acaatgtagg tatccgcggt tacatgtacc     840
```

```
tgaaaggtcc gcgtggttct gttatgacta ccaacatcta cctgaactct tccctgtacc    900
gtggtaccaa attcatcatc aagaaatacg cgtctggtaa caaggacaat atcgttcgca    960
acaatgatcg tgtatacatc aatgttgtag ttaagaacaa agaataccgt ctggctacca   1020
atgcttctca ggctggtgta gaaaagatct tgtctgctct ggaaatcccg gacgttggta   1080
atctgtctca ggtagttgta atgaaatcca agaacgacca gggtatcact aacaaatgca   1140
aaatgaatct gcaggacaac aatggtaacg atatcggttt catcggtttc caccagttca   1200
acaatatcgc taaactggtt gcttccaact ggtacaatcg tcagatcgaa cgttcctctc   1260
gcactctggg ttgctcttgg gagttcatcc cggttgatga cggttggggt gaacgtccgc   1320
tgtaacccgg gaaagctt                                                 1338
```

<210> SEQ ID NO 38
<211> LENGTH: 415
<212> TYPE: PRT
<213> ORGANISM: Clostridium botulinum

<400> SEQUENCE: 38

```
Arg Tyr Glu Ser Asn His Leu Ile Asp Leu Ser Arg Tyr Ala Ser Lys
  1               5                  10                  15

Ile Asn Ile Gly Ser Lys Val Asn Phe Asp Pro Ile Asp Lys Asn Gln
             20                  25                  30

Ile Gln Leu Phe Asn Leu Glu Ser Ser Lys Ile Glu Val Ile Leu Lys
         35                  40                  45

Asn Ala Ile Val Tyr Asn Ser Met Tyr Glu Asn Phe Ser Thr Ser Phe
     50                  55                  60

Trp Ile Arg Ile Pro Lys Tyr Phe Asn Ser Ile Ser Leu Asn Asn Glu
 65                  70                  75                  80

Tyr Thr Ile Ile Asn Cys Met Glu Asn Asn Ser Gly Trp Lys Val Ser
                 85                  90                  95

Leu Asn Tyr Gly Glu Ile Ile Trp Thr Leu Gln Asp Thr Gln Glu Ile
            100                 105                 110

Lys Gln Arg Val Val Phe Lys Tyr Ser Gln Met Ile Asn Ile Ser Asp
        115                 120                 125

Tyr Ile Asn Arg Trp Ile Phe Val Thr Ile Thr Asn Asn Arg Leu Asn
    130                 135                 140

Asn Ser Lys Ile Tyr Ile Asn Gly Arg Leu Ile Asp Gln Lys Pro Ile
145                 150                 155                 160

Ser Asn Leu Gly Asn Ile His Ala Ser Asn Asn Ile Met Phe Lys Leu
                165                 170                 175

Asp Gly Cys Arg Asp Thr His Arg Tyr Ile Trp Ile Phe Tyr Phe Asn
            180                 185                 190

Leu Phe Asp Lys Glu Leu Asn Glu Lys Glu Ile Lys Asp Leu Tyr Asp
        195                 200                 205

Asn Gln Ser Asn Ser Gly Ile Leu Lys Asp Phe Trp Gly Asp Tyr Leu
    210                 215                 220

Gln Tyr Asp Lys Pro Tyr Tyr Met Leu Asn Leu Tyr Asp Pro Asn Lys
225                 230                 235                 240

Tyr Val Asp Val Asn Asn Val Gly Ile Arg Gly Tyr Met Tyr Leu Lys
                245                 250                 255

Gly Pro Arg Gly Ser Val Met Thr Thr Asn Ile Tyr Leu Asn Ser Ser
            260                 265                 270

Leu Tyr Arg Gly Thr Lys Phe Ile Ile Lys Lys Tyr Ala Ser Gly Asn
```

```
                    275                 280                 285
Lys Asp Asn Ile Val Arg Asn Asn Asp Arg Val Tyr Ile Asn Val Val
    290                 295                 300

Val Lys Asn Lys Glu Tyr Arg Leu Ala Thr Asn Ala Ser Gln Ala Gly
305                 310                 315                 320

Val Glu Lys Ile Leu Ser Ala Leu Glu Ile Pro Asp Val Gly Asn Leu
                325                 330                 335

Ser Gln Val Val Val Met Lys Ser Lys Asn Asp Gln Gly Ile Thr Asn
                340                 345                 350

Lys Cys Lys Met Asn Leu Gln Asp Asn Asn Gly Asn Asp Ile Gly Phe
            355                 360                 365

Ile Gly Phe His Gln Phe Asn Asn Ile Ala Lys Leu Val Ala Ser Asn
        370                 375                 380

Trp Tyr Asn Arg Gln Ile Glu Arg Ser Ser Arg Thr Leu Gly Cys Ser
385                 390                 395                 400

Trp Glu Phe Ile Pro Val Asp Asp Gly Trp Gly Glu Arg Pro Leu
                405                 410                 415

<210> SEQ ID NO 39
<211> LENGTH: 1351
<212> TYPE: DNA
<213> ORGANISM: Artificial Sequence
<220> FEATURE:
<223> OTHER INFORMATION: Synthetic construct based on BoNTB Hc

<400> SEQUENCE: 39
atggctttca acaaatacaa ttccgaaatc ctgaacaata tcatcctgaa cctgcgttac      60
aaagacaaca atctgatcga tctgtctggt tacggtgcta aagttgaagt atacgacggt     120
gttgaactga atgacaagaa ccagttcaaa ctgacctctt ccgctaactc taagatccgt     180
gttactcaga atcagaacat catcttcaac tccgtattcc tggacttctc tgtttccttc     240
tggatccgta tcccgaaata caagaacgac ggtatccaga attacatcca caatgaatac     300
accatcatca ctgcatgaa gaataactct ggttggaaga ctccatccg ggtaaccgt        360 atcatctgga ctctgatcga tatcaacggt aagaccaaat ctgtattctt cgaatacaac     420
atccgtgaag acatctctga atacatcaat cgctggttct tcgttaccat caccaataac     480
ctgaacaatg ctaaaatcta catcaacggt aaactggaat ctaataccga catcaaagac     540
atccgtgaag ttatcgctaa cggtgaaatc atcttcaaac tggacggtga catcgatcgt     600
acccagttca tctggatgaa atacttctcc atcttcaaca ccgaactgtc tcagtccaat     660
atcgaagaac ggtacaagat ccagtcttac tccgaatacc tgaaagactt ctggggtaat     720
ccgctgatgt acaacaaaga atactatatg ttcaatgctg gtaacaagaa ctcttacatc     780
aaactgaaga aagactctcc ggttggtgaa atcctgactc gttccaaata caaccagaac     840
tctaaataca tcaactaccg cgacctgtac atcggtaaa agttcatcat ccgtcgcaaa     900
tctaactctc agtccatcaa tgatgacatc gtacgtaaag aagactacat ctacctggac     960
ttcttcaacc tgaatcagga atggcgtgta tacacctaca gtacttcaa gaaagaagaa     1020 gaaaagcttt tcctggctcc gatctctgat tccgacgaac tctacaacac catccagatc    1080
aaagaatacg acgaacagcc gacctactct tgccagctgc tgttcaagaa agatgaagaa    1140
tctactgacg aaatcggtct gatcggtatc caccgtttct acgaatctgg tatcgtattc    1200
gaagaataca aagactactt ctgcatctcc aaatggtacc tgaaggaagt taacgcaaa     1260 ccgtacaacc tgaaactggg ttgcaattgg cagttcatcc cgaaagacga aggttggacc    1320
```

```
gaatagtaac ctctagagtc gaggcctgca g                                    1351
```

<210> SEQ ID NO 40
<211> LENGTH: 439
<212> TYPE: PRT
<213> ORGANISM: Clostridium botulinum

<400> SEQUENCE: 40

| | | | | | | | | | | | | | | | |
|---|---|---|---|---|---|---|---|---|---|---|---|---|---|---|---|
| Phe | Asn | Lys | Tyr | Asn | Ser | Glu | Ile | Leu | Asn | Ile | Ile | Leu | Asn | Leu | |
| 1 | | | | 5 | | | | 10 | | | | 15 | | | |
| Arg | Tyr | Lys | Asp | Asn | Leu | Ile | Asp | Leu | Ser | Gly | Tyr | Gly | Ala | Lys | |
| | | 20 | | | | 25 | | | | 30 | | | | | |
| Val | Glu | Val | Tyr | Asp | Gly | Val | Glu | Leu | Asn | Asp | Lys | Asn | Gln | Phe | Lys |
| | | 35 | | | | 40 | | | | 45 | | | | | |
| Leu | Thr | Ser | Ser | Ala | Asn | Ser | Lys | Ile | Arg | Val | Thr | Gln | Asn | Gln | Asn |
| | 50 | | | | 55 | | | | 60 | | | | | | |
| Ile | Ile | Phe | Asn | Ser | Val | Phe | Leu | Asp | Phe | Ser | Val | Ser | Phe | Trp | Ile |
| 65 | | | | 70 | | | | 75 | | | | | | | 80 |
| Arg | Ile | Pro | Lys | Tyr | Lys | Asn | Asp | Gly | Ile | Gln | Asn | Tyr | Ile | His | Asn |
| | | | 85 | | | | 90 | | | | 95 | | | | |
| Glu | Tyr | Thr | Ile | Ile | Asn | Cys | Met | Lys | Asn | Asn | Ser | Gly | Trp | Lys | Ile |
| | | 100 | | | | 105 | | | | 110 | | | | | |
| Ser | Ile | Arg | Gly | Asn | Arg | Ile | Ile | Trp | Thr | Leu | Ile | Asp | Ile | Asn | Gly |
| | 115 | | | | 120 | | | | 125 | | | | | | |
| Lys | Thr | Lys | Ser | Val | Phe | Phe | Glu | Tyr | Asn | Ile | Arg | Glu | Asp | Ile | Ser |
| 130 | | | | 135 | | | | 140 | | | | | | | |
| Glu | Tyr | Ile | Asn | Arg | Trp | Phe | Phe | Val | Thr | Ile | Thr | Asn | Asn | Leu | Asn |
| 145 | | | | 150 | | | | 155 | | | | | | | 160 |
| Asn | Ala | Lys | Ile | Tyr | Ile | Asn | Gly | Lys | Leu | Glu | Ser | Asn | Thr | Asp | Ile |
| | | | 165 | | | | 170 | | | | 175 | | | | |
| Lys | Asp | Ile | Arg | Glu | Val | Ile | Ala | Asn | Gly | Glu | Ile | Ile | Phe | Lys | Leu |
| | | | 180 | | | | 185 | | | | 190 | | | | |
| Asp | Gly | Asp | Ile | Asp | Arg | Thr | Gln | Phe | Ile | Trp | Met | Lys | Tyr | Phe | Ser |
| | | 195 | | | | 200 | | | | 205 | | | | | |
| Ile | Phe | Asn | Thr | Glu | Leu | Ser | Gln | Ser | Asn | Ile | Glu | Glu | Arg | Tyr | Lys |
| | 210 | | | | 215 | | | | 220 | | | | | | |
| Ile | Gln | Ser | Tyr | Ser | Glu | Tyr | Leu | Lys | Asp | Phe | Trp | Gly | Asn | Pro | Leu |
| 225 | | | | 230 | | | | 235 | | | | | | | 240 |
| Met | Tyr | Asn | Lys | Glu | Tyr | Tyr | Met | Phe | Asn | Ala | Gly | Asn | Lys | Asn | Ser |
| | | | 245 | | | | 250 | | | | 255 | | | | |
| Tyr | Ile | Lys | Leu | Lys | Lys | Asp | Ser | Pro | Val | Gly | Glu | Ile | Leu | Thr | Arg |
| | | 260 | | | | 265 | | | | 270 | | | | | |
| Ser | Lys | Tyr | Asn | Gln | Asn | Ser | Lys | Tyr | Ile | Asn | Tyr | Arg | Asp | Leu | Tyr |
| | 275 | | | | 280 | | | | 285 | | | | | | |
| Ile | Gly | Glu | Lys | Phe | Ile | Ile | Arg | Arg | Lys | Ser | Asn | Ser | Gln | Ser | Ile |
| | 290 | | | | 295 | | | | 300 | | | | | | |
| Asn | Asp | Asp | Ile | Val | Arg | Lys | Glu | Asp | Tyr | Ile | Tyr | Leu | Asp | Phe | Phe |
| 305 | | | | 310 | | | | 315 | | | | | | | 320 |
| Asn | Leu | Asn | Gln | Glu | Trp | Arg | Val | Tyr | Thr | Tyr | Lys | Tyr | Phe | Lys | Lys |
| | | | 325 | | | | 330 | | | | 335 | | | | |
| Glu | Glu | Glu | Lys | Leu | Phe | Leu | Ala | Pro | Ile | Ser | Asp | Ser | Asp | Glu | Phe |
| | | | 340 | | | | 345 | | | | 350 | | | | |
| Tyr | Asn | Thr | Ile | Gln | Ile | Lys | Glu | Tyr | Asp | Glu | Gln | Pro | Thr | Tyr | Ser |
| | | | 355 | | | | 360 | | | | 365 | | | | |

```
Cys Gln Leu Leu Phe Lys Lys Asp Glu Glu Ser Thr Asp Glu Ile Gly
        370                 375                 380

Leu Ile Gly Ile His Arg Phe Tyr Glu Ser Gly Ile Val Phe Glu Glu
385                 390                 395                 400

Tyr Lys Asp Tyr Phe Cys Ile Ser Lys Trp Tyr Leu Lys Glu Val Lys
                405                 410                 415

Arg Lys Pro Tyr Asn Leu Lys Leu Gly Cys Asn Trp Gln Phe Ile Pro
            420                 425                 430

Lys Asp Glu Gly Trp Thr Glu
        435

<210> SEQ ID NO 41
<211> LENGTH: 848
<212> TYPE: PRT
<213> ORGANISM: Clostridium botulinum

<400> SEQUENCE: 41

Ala Leu Asn Asp Leu Cys Ile Lys Val Asn Asn Trp Asp Leu Phe Phe
1               5                   10                  15

Ser Pro Ser Glu Asp Asn Phe Thr Asn Asp Leu Asn Lys Gly Glu Glu
            20                  25                  30

Ile Thr Ser Asp Thr Asn Ile Glu Ala Ala Glu Glu Asn Ile Ser Leu
        35                  40                  45

Asp Leu Ile Gln Gln Tyr Tyr Leu Thr Phe Asn Phe Asp Asn Glu Pro
    50                  55                  60

Glu Asn Ile Ser Ile Glu Asn Leu Ser Ser Asp Ile Ile Gly Gln Leu
65                  70                  75                  80

Glu Leu Met Pro Asn Ile Glu Arg Phe Pro Asn Gly Lys Lys Tyr Glu
                85                  90                  95

Leu Asp Lys Tyr Thr Met Phe His Tyr Leu Arg Ala Gln Glu Phe Glu
            100                 105                 110

His Gly Lys Ser Arg Ile Ala Leu Thr Asn Ser Val Asn Glu Ala Leu
        115                 120                 125

Leu Asn Pro Ser Arg Val Tyr Thr Phe Phe Ser Ser Asp Tyr Val Lys
    130                 135                 140

Lys Val Asn Lys Ala Thr Glu Ala Ala Met Phe Leu Gly Trp Val Glu
145                 150                 155                 160

Gln Leu Val Tyr Asp Phe Thr Asp Glu Thr Ser Glu Val Ser Thr Thr
                165                 170                 175

Asp Lys Ile Ala Asp Ile Thr Ile Ile Pro Tyr Ile Gly Pro Ala
            180                 185                 190

Leu Asn Ile Gly Asn Met Leu Tyr Lys Asp Asp Phe Val Gly Ala Leu
        195                 200                 205

Ile Phe Ser Gly Ala Val Ile Leu Leu Glu Phe Ile Pro Glu Ile Ala
    210                 215                 220

Ile Pro Val Leu Gly Thr Phe Ala Leu Val Ser Tyr Ile Ala Asn Lys
225                 230                 235                 240

Val Leu Thr Val Gln Thr Ile Asp Asn Ala Leu Ser Lys Arg Asn Glu
                245                 250                 255

Lys Trp Asp Glu Val Tyr Lys Tyr Ile Val Thr Asn Trp Leu Ala Lys
            260                 265                 270

Val Asn Thr Gln Ile Asp Leu Ile Arg Lys Lys Met Lys Glu Ala Leu
        275                 280                 285

Glu Asn Gln Ala Glu Ala Thr Lys Ala Ile Ile Asn Tyr Gln Tyr Asn
```

```
                290                 295                 300
Gln Tyr Thr Glu Glu Lys Asn Asn Ile Asn Phe Asn Ile Asp Asp
305                 310                 315                 320

Leu Ser Ser Lys Leu Asn Glu Ser Ile Asn Lys Ala Met Ile Asn Ile
                325                 330                 335

Asn Lys Phe Leu Asn Gln Cys Ser Val Ser Tyr Leu Met Asn Ser Met
                340                 345                 350

Ile Pro Tyr Gly Val Lys Arg Leu Glu Asp Phe Asp Ala Ser Leu Lys
                355                 360                 365

Asp Ala Leu Leu Lys Tyr Ile Tyr Asp Asn Arg Gly Thr Leu Ile Gly
370                 375                 380

Gln Val Asp Arg Leu Lys Asp Lys Val Asn Asn Thr Leu Ser Thr Asp
385                 390                 395                 400

Ile Pro Phe Gln Leu Ser Lys Tyr Val Asp Asn Gln Arg Leu Leu Ser
                405                 410                 415

Thr Phe Thr Glu Tyr Ile Lys Asn Ile Ile Asn Thr Ser Ile Leu Asn
                420                 425                 430

Leu Arg Tyr Glu Ser Asn His Leu Ile Asp Leu Ser Arg Tyr Ala Ser
                435                 440                 445

Lys Ile Asn Ile Gly Ser Lys Val Asn Phe Asp Pro Ile Asp Lys Asn
                450                 455                 460

Gln Ile Gln Leu Phe Asn Leu Glu Ser Ser Lys Ile Glu Val Ile Leu
465                 470                 475                 480

Lys Asn Ala Ile Val Tyr Asn Ser Met Tyr Glu Asn Phe Ser Thr Ser
                485                 490                 495

Phe Trp Ile Arg Ile Pro Lys Tyr Phe Asn Ser Ile Ser Leu Asn Asn
                500                 505                 510

Glu Tyr Thr Ile Ile Asn Cys Met Glu Asn Asn Ser Gly Trp Lys Val
                515                 520                 525

Ser Leu Asn Tyr Gly Glu Ile Ile Trp Thr Leu Gln Asp Thr Gln Glu
                530                 535                 540

Ile Lys Gln Arg Val Val Phe Lys Tyr Ser Gln Met Ile Asn Ile Ser
545                 550                 555                 560

Asp Tyr Ile Asn Arg Trp Ile Phe Val Thr Ile Thr Asn Asn Arg Leu
                565                 570                 575

Asn Asn Ser Lys Ile Tyr Ile Asn Gly Arg Leu Ile Asp Gln Lys Pro
                580                 585                 590

Ile Ser Asn Leu Gly Asn Ile His Ala Ser Asn Asn Ile Met Phe Lys
                595                 600                 605

Leu Asp Gly Cys Arg Asp Thr His Arg Tyr Ile Trp Ile Lys Tyr Phe
                610                 615                 620

Asn Leu Phe Asp Lys Glu Leu Asn Glu Lys Glu Ile Lys Asp Leu Tyr
625                 630                 635                 640

Asp Asn Gln Ser Asn Ser Gly Ile Leu Lys Asp Phe Trp Gly Asp Tyr
                645                 650                 655

Leu Gln Tyr Asp Lys Pro Tyr Tyr Met Leu Asn Leu Tyr Asp Pro Asn
                660                 665                 670

Lys Tyr Val Asp Val Asn Asn Val Gly Ile Arg Gly Tyr Met Tyr Leu
                675                 680                 685

Lys Gly Pro Arg Gly Ser Val Met Thr Thr Asn Ile Tyr Leu Asn Ser
                690                 695                 700

Ser Leu Tyr Arg Gly Thr Lys Phe Ile Ile Lys Lys Tyr Ala Ser Gly
705                 710                 715                 720
```

```
Asn Lys Asp Asn Ile Val Arg Asn Asp Arg Val Tyr Ile Asn Val
                725                 730                 735
Val Val Lys Asn Lys Glu Tyr Arg Leu Ala Thr Asn Ala Ser Gln Ala
                740                 745                 750
Gly Val Glu Lys Ile Leu Ser Ala Leu Glu Ile Pro Asp Val Gly Asn
                755                 760                 765
Leu Ser Gln Val Val Met Lys Ser Lys Asn Asp Gln Gly Ile Thr
        770                 775                 780
Asn Lys Cys Lys Met Asn Leu Gln Asp Asn Asn Gly Asn Asp Ile Gly
785                 790                 795                 800
Phe Ile Gly Phe His Gln Phe Asn Asn Ile Ala Lys Leu Val Ala Ser
                805                 810                 815
Asn Trp Tyr Asn Arg Gln Ile Glu Arg Ser Ser Arg Thr Leu Gly Cys
                820                 825                 830
Ser Trp Glu Phe Ile Pro Val Asp Asp Gly Trp Gly Glu Arg Pro Leu
        835                 840                 845

<210> SEQ ID NO 42
<211> LENGTH: 850
<212> TYPE: PRT
<213> ORGANISM: Clostridium botulinum

<400> SEQUENCE: 42

Ala Pro Gly Ile Cys Ile Asp Val Asp Asn Glu Asp Leu Phe Phe Ile
1               5                   10                  15
Ala Asp Lys Asn Ser Phe Ser Asp Asp Leu Ser Lys Asn Glu Arg Ile
                20                  25                  30
Glu Tyr Asn Thr Gln Ser Asn Tyr Ile Glu Asn Asp Phe Pro Ile Asn
                35                  40                  45
Glu Leu Ile Leu Asp Thr Asp Leu Ile Ser Lys Ile Glu Leu Pro Ser
        50                  55                  60
Glu Asn Thr Glu Ser Leu Thr Asp Phe Asn Val Asp Val Pro Val Tyr
65              70                  75                  80
Glu Lys Gln Pro Ala Ile Lys Lys Ile Phe Thr Asp Glu Asn Thr Ile
                85                  90                  95
Phe Gln Tyr Leu Tyr Ser Gln Thr Phe Pro Leu Asp Ile Arg Asp Ile
                100                 105                 110
Ser Leu Thr Ser Ser Phe Asp Asp Ala Leu Leu Phe Ser Asn Lys Val
        115                 120                 125
Tyr Ser Phe Phe Ser Met Asp Tyr Ile Lys Thr Ala Asn Lys Val Val
        130                 135                 140
Glu Ala Gly Leu Phe Ala Gly Trp Val Lys Gln Ile Val Asn Asp Phe
145                 150                 155                 160
Val Ile Glu Ala Asn Lys Ser Asn Thr Met Asp Lys Ile Ala Asp Ile
                165                 170                 175
Ser Leu Ile Val Pro Tyr Ile Gly Leu Ala Leu Asn Val Gly Asn Glu
        180                 185                 190
Thr Ala Lys Gly Asn Phe Glu Asn Ala Phe Glu Ile Ala Gly Ala Ser
        195                 200                 205
Ile Leu Leu Glu Phe Ile Pro Glu Leu Ile Pro Val Val Gly Ala
        210                 215                 220
Phe Leu Leu Glu Ser Tyr Ile Asp Asn Lys Asn Lys Ile Ile Lys Thr
225                 230                 235                 240
Ile Asp Asn Ala Leu Thr Lys Arg Asn Glu Lys Trp Ser Asp Met Tyr
```

-continued

```
            245                 250                 255
Gly Leu Ile Val Ala Gln Trp Leu Ser Thr Val Asn Thr Gln Phe Tyr
                260                 265                 270
Thr Ile Lys Glu Gly Met Tyr Lys Ala Leu Asn Tyr Gln Ala Gln Ala
            275                 280                 285
Leu Glu Glu Ile Ile Lys Tyr Arg Tyr Asn Ile Tyr Ser Glu Lys Glu
        290                 295                 300
Lys Ser Asn Ile Asn Ile Asp Phe Asn Asp Ile Asn Ser Lys Leu Asn
305                 310                 315                 320
Glu Gly Ile Asn Gln Ala Ile Asp Asn Ile Asn Asn Phe Ile Asn Gly
                325                 330                 335
Cys Ser Val Ser Tyr Leu Met Lys Lys Met Ile Pro Leu Ala Val Glu
            340                 345                 350
Lys Leu Leu Asp Phe Asp Asn Thr Leu Lys Lys Asn Leu Leu Asn Tyr
        355                 360                 365
Ile Asp Glu Asn Lys Leu Tyr Leu Ile Gly Ser Ala Glu Tyr Glu Lys
        370                 375                 380
Ser Lys Val Asn Lys Tyr Leu Lys Thr Ile Met Pro Phe Asp Leu Ser
385                 390                 395                 400
Ile Tyr Thr Asn Asp Thr Ile Leu Ile Glu Met Phe Asn Lys Tyr Asn
                405                 410                 415
Ser Glu Ile Leu Asn Asn Ile Ile Leu Asn Leu Arg Tyr Lys Asp Asn
                420                 425                 430
Asn Leu Ile Asp Leu Ser Gly Tyr Gly Ala Lys Val Glu Val Tyr Asp
            435                 440                 445
Gly Val Glu Leu Asn Asp Lys Asn Gln Phe Lys Leu Thr Ser Ser Ala
        450                 455                 460
Asn Ser Lys Ile Arg Val Thr Gln Asn Gln Asn Ile Ile Phe Asn Ser
465                 470                 475                 480
Val Phe Leu Asp Phe Ser Val Ser Phe Trp Ile Arg Ile Pro Lys Tyr
                485                 490                 495
Lys Asn Asp Gly Ile Gln Asn Tyr Ile His Asn Glu Tyr Thr Ile Ile
                500                 505                 510
Asn Cys Met Lys Asn Asn Ser Gly Trp Lys Ile Ser Ile Arg Gly Asn
            515                 520                 525
Arg Ile Ile Trp Thr Leu Ile Asp Ile Asn Gly Lys Thr Lys Ser Val
        530                 535                 540
Phe Phe Glu Tyr Asn Ile Arg Glu Asp Ile Ser Glu Tyr Ile Asn Arg
545                 550                 555                 560
Trp Phe Phe Val Thr Ile Thr Asn Asn Leu Asn Asn Ala Lys Ile Tyr
                565                 570                 575
Ile Asn Gly Lys Leu Glu Ser Asn Thr Asp Ile Lys Asp Ile Arg Glu
            580                 585                 590
Val Ile Ala Asn Gly Glu Ile Ile Phe Lys Leu Asp Gly Asp Ile Asp
        595                 600                 605
Arg Thr Gln Phe Ile Trp Met Lys Tyr Phe Ser Ile Phe Asn Thr Glu
    610                 615                 620
Leu Ser Gln Ser Asn Ile Glu Glu Arg Tyr Lys Ile Gln Ser Tyr Ser
625                 630                 635                 640
Glu Tyr Leu Lys Asp Phe Trp Gly Asn Pro Leu Met Tyr Asn Lys Glu
                645                 650                 655
Tyr Tyr Met Phe Asn Ala Gly Asn Lys Asn Ser Tyr Ile Lys Leu Lys
            660                 665                 670
```

-continued

Lys Asp Ser Pro Val Gly Glu Ile Leu Thr Arg Ser Lys Tyr Asn Gln
            675                 680                 685

Asn Ser Lys Tyr Ile Asn Tyr Arg Asp Leu Tyr Ile Gly Glu Lys Phe
        690                 695                 700

Ile Ile Arg Arg Lys Ser Asn Ser Gln Ser Ile Asn Asp Asp Ile Val
705                 710                 715                 720

Arg Lys Glu Asp Tyr Ile Tyr Leu Asp Phe Phe Asn Leu Asn Gln Glu
                725                 730                 735

Trp Arg Val Tyr Thr Tyr Lys Tyr Phe Lys Lys Glu Glu Lys Leu
            740                 745                 750

Phe Leu Ala Pro Ile Ser Asp Ser Asp Glu Phe Tyr Asn Thr Ile Gln
            755                 760                 765

Ile Lys Glu Tyr Asp Glu Gln Pro Thr Tyr Ser Cys Gln Leu Leu Phe
            770                 775                 780

Lys Lys Asp Glu Glu Ser Thr Asp Glu Ile Gly Leu Ile Gly Ile His
785                 790                 795                 800

Arg Phe Tyr Glu Ser Gly Ile Val Phe Glu Glu Tyr Lys Asp Tyr Phe
                805                 810                 815

Cys Ile Ser Lys Trp Tyr Leu Lys Glu Val Lys Arg Lys Pro Tyr Asn
            820                 825                 830

Leu Lys Leu Gly Cys Asn Trp Gln Phe Ile Pro Lys Asp Glu Gly Trp
            835                 840                 845

Thr Glu
    850

<210> SEQ ID NO 43
<211> LENGTH: 1296
<212> TYPE: PRT
<213> ORGANISM: Clostridium botulinum
<300> PUBLICATION INFORMATION:
<308> DATABASE ACCESSION NUMBER: X52066
<309> DATABASE ENTRY DATE: 1993-04-23

<400> SEQUENCE: 43

Met Gln Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr

-continued

```
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
            195                 200                 205
Gly Ala Gly Lys Phe Ala Thr Asp Pro Ala Val Thr Leu Ala His Glu
            210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
            245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
            275                 280                 285
Lys Phe Lys Asp Ile Ala Ser Thr Leu Asn Lys Ala Lys Ser Ile Val
            290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
            325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
            405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
            485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
            530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
            565                 570                 575
Leu Asn Pro Ser Arg Val Tyr Thr Phe Phe Ser Ser Asp Tyr Val Lys
            580                 585                 590
```

-continued

```
Lys Val Asn Lys Ala Thr Glu Ala Met Phe Leu Gly Trp Val Glu
        595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
                690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
        770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
        930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
        995                 1000                1005
```

-continued

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
                1060                1065                1070

Asn Leu Phe Asp Lys Glu Leu Asn Glu Lys Ile Lys Asp Leu Tyr
            1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295

<210> SEQ ID NO 44
<211> LENGTH: 1291
<212> TYPE: PRT
<213> ORGANISM: Clostridium botulinum
<300> PUBLICATION INFORMATION:
<308> DATABASE ACCESSION NUMBER: M81186
<309> DATABASE ENTRY DATE: 1993-04-26

<400> SEQUENCE: 44

Met Pro Val Thr Ile Asn Asn Phe Asn Tyr Asn Asp Pro Ile Asp Asn
 1               5                  10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

-continued

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

-continued

```
Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
            610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
            725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
            770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
            805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
            850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
```

-continued

```
                915                 920                 925
Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
                995                1000                1005

Asn Asn Leu Asn Asn Ala Lys Ile Tyr Ile Asn Gly Lys Leu Glu Ser
       1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
                1045                1050                1055

Lys Tyr Phe Ser Ile Phe Asn Thr Glu Leu Ser Gln Ser Asn Ile Glu
            1060                1065                1070

Glu Arg Tyr Lys Ile Gln Ser Tyr Ser Glu Tyr Leu Lys Asp Phe Trp
        1075                1080                1085

Gly Asn Pro Leu Met Tyr Asn Lys Glu Tyr Tyr Met Phe Asn Ala Gly
        1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
                1140                1145                1150

Ser Gln Ser Ile Asn Asp Asp Ile Val Arg Lys Glu Asp Tyr Ile Tyr
        1155                1160                1165

Leu Asp Phe Phe Asn Leu Asn Gln Glu Trp Arg Val Tyr Thr Tyr Lys
        1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
                1220                1225                1230

Asp Glu Ile Gly Leu Ile Gly Ile His Arg Phe Tyr Glu Ser Gly Ile
            1235                1240                1245

Val Phe Glu Glu Tyr Lys Asp Tyr Phe Cys Ile Ser Lys Trp Tyr Leu
    1250                1255                1260

Lys Glu Val Lys Arg Lys Pro Tyr Asn Leu Lys Leu Gly Cys Asn Trp
1265                1270                1275                1280

Gln Phe Ile Pro Lys Asp Glu Gly Trp Thr Glu
                1285                1290
```